(12) United States Patent
Stockdill et al.

(10) Patent No.: US 11,427,612 B2
(45) Date of Patent: Aug. 30, 2022

(54) EPIMERIZATION-FREE N TO C SOLID-PHASE PEPTIDE SYNTHESIS

(71) Applicant: Wayne State University, Detroit, MI (US)

(72) Inventors: Jennifer L. Stockdill, West Bloomfield Township, MI (US); Christine A. Arbour, Cambridge, MA (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 16/546,549

(22) Filed: Aug. 21, 2019

(65) Prior Publication Data

US 2020/0062801 A1 Feb. 27, 2020

Related U.S. Application Data

(60) Provisional application No. 62/720,668, filed on Aug. 21, 2018.

(51) Int. Cl.
| | |
|---|---|
| *C07K 1/08* | (2006.01) |
| *C07K 1/10* | (2006.01) |
| *C07K 1/04* | (2006.01) |
| *C07K 1/02* | (2006.01) |

(52) U.S. Cl.
CPC .............. *C07K 1/042* (2013.01); *C07K 1/023* (2013.01); *C07K 1/084* (2013.01); *C07K 1/10* (2013.01)

(58) Field of Classification Search
CPC ........... C07K 1/023; C07K 1/084; C07K 1/10
See application file for complete search history.

(56) References Cited

U.S. PATENT DOCUMENTS

2017/0008923 A1* 1/2017 Rocchi ..................... C07K 1/02

OTHER PUBLICATIONS

Johnson, et al., A Potent Alpha/Beta-Peptide Analogue of GLP-1 with Prolonged Action, in Vivo, Journal of the American Chemical Society, vol. 136, No. 37, 2014, pp. 12848-12851.
Johnson, et al., "A reversible protecting group for the amide bond in peptides. Use in the synthesis of 'difficult sequences'," Journal of the Chemical Society, Chemical Communications, No. 4, 1993, 369-372.
Johnson, et al., "Insights into the mechanism and catalysis of the native chemical ligation reaction," Journal of the American Chemical Society, vol. 128, No. 20, 2006, pp. 6640-6646.
Juvekar, et al., Highly Efficient Synthetic Method on Pyroacm Resin Using the Boc SPPS Protocol for C-terminal Cysteine Peptide Synthesis, Bulletin of the Korean Chemical Society, vol. 38, 2017, pp. 54-62.
Kang, et al., "Peptide amidation: Production of peptide hormones in vivo and in vitro," Angewandte Chemie International Edition English, vol. 44, No. 39, 2005, pp. 6333-6337.
Kang, et al., "The precursor of Alzheimer's disease amyloid A4 protein resembles a cell-surface receptor," Nature, vol. 325, No. 6106, 1987, pp. 733-736.

(Continued)

*Primary Examiner* — Jeffrey E. Russel
(74) *Attorney, Agent, or Firm* — Lee & Hayes, P.C.

(57) ABSTRACT

The present disclosure provides a method of solid-phase peptide synthesis from the N terminus to C terminus without detectable epimerization of the C-terminal amino acid. The method includes using derivatized amino acids comprising a diamino-aryl group.

20 Claims, 41 Drawing Sheets

Specification includes a Sequence Listing.

General strategy for N to C SPPS using N-acyl ureas.

(56) References Cited

OTHER PUBLICATIONS

Kanzian, et al., "Nucleophilic Reactivities of Primary and Secondary Amines in Acetonitrile," European Journal of Organic Chemistry, vol. 2009, No. 36, 2009, pp. 6379-6385.
Kent, "Chemical Synthesis of Peptides and Proteins," Annual Review of Biochemistry, vol. 57, 1988, pp. 957-989.
Kent, "The critical role of peptide chemistry in the life sciences," Journal of Peptide Science, vol. 21, No. 3, 2015, pp. 136-138.
Krchnak, et al., "Aggregation of resin-bound peptides during solid-phase peptide synthesis," International Journal of Peptide Research, vol. 42, No. 5, 1993, pp. 450-454.
Kretschy, et al., "Next-Generation o-Nitrobenzyl Photolabile Groups for Light-Directed Chemistry and Microarray Synthesis," Angewandte Chemie, vol. 54, No. 29, 2015, pp. 8555-8559.
Larsen and Holm, "Incomplete Fmoc deprotection in solid-phase synthesis of peptides," International Journal of Peptide Research, vol. 43, No. 1, 1994, pp. 1-9.
Lee, et al., "Indium Tri(isopropoxide)-Catalyzed Selective Meerwein-Ponndorf-Verley Reduction of Aliphatic and Aromatic Aldehydes," Journal of Organic Chemistry, vol. 77, No. 10, 2012, pp. 4821-4835.
Lelievre, et al., "Native Chemical Ligation Strategy to Overcome Side Reactions during Fmoc-Based Synthesis of C-Terminal Cysteine-Containing Peptides," Organic Letters, vol. 18, No. 5, 2016, pp. 920-923.
Li and Danishefsky, "New Chemistry with Old Functional Groups: On the Reaction of Isonitriles with Carboxylic Acids—A Route to Various Amide Types," Journal of the American Chemical Society, vol. 130, No. 16, 2008, pp. 5446-5448.
Loibl, et al., "A Type of Auxiliary for Native Chemical Peptide Ligation beyond Cysteine and Glycine Junctions," Angewandte Chemie International Edition English, vol. 54, No. 50, 2015, pp. 15055-15059.
Lukszo, et al., "3-(1-Piperidinyl)alanine formation during the preparation of C-terminal cysteine peptides with the Fmoc/t-Bu strategy," Letters in Peptide Science, vol. 3, 1996, pp. 157-166.
Mahto, et al., "A Reversible Protection Strategy To Improve Fmoc-SPPS of Peptide Thioesters by the N-Acylurea Approach," ChemBioChem, vol. 12, No. 16, 2011, pp. 2488-2494.
Marinzi, et al., "An o-nitrobenzyl scaffold for peptide ligation: synthesis and applications," Bioorganic & Medicinal Chemistry, vol. 12, No. 10, 2004, pp. 2749-2757.
Martinez-Padron, et al., "Modulation of Aplysia Californica Siphon Sensory Neurons by Conopressin G," The Journal of Experimental Biology, vol. 171, No. 1, 1992, pp. 79-105.
Maslennikov, et al., "NMR spatial structure of alpha-conotoxin ImI reveals a common scaffold in snail and snake toxins recognizing neuronal nicotinic acetylcholine receptors," FEBS Letters, vol. 444, No. 2-3, 1999, pp. 275-280.
Miranda, et al., "Accelerated chemical synthesis of peptides and small proteins," PNAS USA, vol. 96, No. 4, 1999, pp. 1181-1186.
Mullen, et al., "Synthesis of a-factor peptide from *Saccharomyces cerevisiae* and photoactive analogues via Fmoc solid phase methodology," Bioorganic & Medicinal Chemistry, vol. 19, No. 1, 2011, pp. 490-497.
Naider & Becker, "Synthesis of prenylated peptides and peptide esters," Biopolymers, vol. 43, No. 1, 1997, pp. 3-14.
Nielsen, et al., "Cosolvent-assisted oxidative folding of a bicyclic alpha-conotoxin ImI," Journal of Peptide Research, vol. 10, No. 5, 2004, pp. 249-256.
Ollivier, et al., "Correction: A simple and traceless solid phase method simplifies the assembly of large peptides and the access to challenging proteins," Chemical Science, vol. 8, No. 8, 2017, 1 page.
Palasek, et al., "Limiting racemization and aspartimide formation in microwave-enhanced Fmoc solid phase peptide synthesis," Journal of Peptide Research, vol. 13, 2007, pp. 143-148.
Paradis-Bas, et al., "The road to the synthesis of difficult peptides", Chemical Society Reviews, vol. 45, No. 3, 2016, pp. 631-654.

Pedersen, et al., "Microwave heating in solid-phase peptide synthesis," Chemical Society Reviews, vol. 41, No. 5, 2012, pp. 1826-1844.
Pels, et al., "Solid-Phase Synthesis of Diverse Peptide Tertiary Amides By Reductive Amination," ACS Combinatorial Science, vol. 17, No. 3, 2015, pp. 152-155.
Quibell, et al., "Reversible Modification of the Acid Labile 2-Hydroxy-4-methoxybenzyl(Hmb) Amide Protecting Group: A simple scheme yielding Backbone Substituted Free Peptides," Tetrahedron Letters, vol. 35, No. 14, 1994, pp. 2237-2238.
Qvortrup, et al., "Photolabile Linker for the Solid-Phase Synthesis of Peptide Hyrdrazides and Heterocycles," Organic Letters, vol. 16, No. 18, 2014, pp. 4782-4785.
Rahman, et al., "Optimization of solid-phase synthesis of difficult peptide sequences via comparison between different improved approaches," Amino Acids, vol. 33, No. 3, 2007, pp. 531-536.
Ramos-Tomillero, et al., "Formylation of Electron-Rich Aromatic Rings Mediated by Dichloromethyl Methyl Ether and TiCl4: Scope and Limitations," Molecules, vol. 20, No. 4, 2015, pp. 5409-5422.
Ramos-Tomillero, et al., "Tetrahydropyranyl, a Nonaromatic Acid-Labile Cys Protecting Group for Fmoc Peptide Chemistry," Organic Letters, vol. 17, No. 7, 2015, pp. 1680-1683.
Salah, et al., "Efficient Microwave-Assisted One Shot Synthesis of Peptaibols Using Inexpensive Coupling Reagents," Organic Letters, vol. 16, No. 6, 2014, pp. 1783-1785.
Salzet, et al., "Isolation, structural characterization and biological function of a lysine-conopressin in the central nervous system," European Journal of Biochemistry, vol. 217, No. 3, 1994, pp. 897-903.
Sarma, et al., "Amino Acid Esters and Amides for Reductive Amination of Mucochloric Acid: Synthesis of Novel Gamma-Lactams, Short Peptides, and Antiseizure Agent Levetiracetam," European Journal of Organic Chemistry, vol. 2006, No. 16, 2006, pp. 3730-3737.
Shelton and Jensen, "Linkers, Resins, and General Procedures for Solid-Phase Peptide Synthesis," Peptide Synthesis and Applications, vol. 1047, 2013, pp. 23-41.
Shin, et al., "Synthesis of Pentafluorophenyl Esters of Nitroveratryloxycarbonyl-Protected Amino Acids," Synlett, vol. 2009, No. 20, 2009, pp. 3307-3310.
Sieminski, et al., "Primary sequence of ionic self-assembling peptide gels affects endothelial cell adhesion and capillary morphogenesis," Journal of Biomedical Materials Research Part A, vol. 87, No. 2, 2008, pp. 494-504.
Simmonds, "Use of the Hmb backbone-protecting group in the synthesis of difficult sequences," International Journal of Peptide Research and Therapeutics, vol. 47, No. 1, 1996, pp. 36-41.
Sohma, et al., "Novel and efficient synthesis of difficult sequence-containing peptides through O—N intramolecular acyl migration reaction of O-acyl isopeptides," ChemComm, vol. 7, No. 1, 2004, pp. 124-125.
Taniguchi, et al., ""Click Peptide" Based on the "O-Acyl Isopeptide Method": Control of ABeta1-42 Production from a Photo-Triggered ABeta1-42 Analogue," Journal of the American Chemical Society, vol. 128, No. 3, 2006, pp. 696-697.
Thomas, et al., "Fmoc-based peptide thioester synthesis with self-purifying effect: heading to native chemical ligation in parallel formats," Journal of Peptide Research, vol. 19, No. 3, 2013, pp. 141-147.
Tickler, et al., "Overview of Solid Phase Synthesis of "Difficult Peptide" Sequences," Current Protocols in Protein Science, vol. 50, 2007, pp. 18.8.1-18.8.6.
Tseng, et al., "Arrays on Aluminum-Coated Glass Slides," Chemistry: An Asian Journal, vol. 3, No. 8-9, 2008, pp. 1395-1405.
Vine, et al., "In vitro cytotoxicity evaluation of some substituted isatin derivatives," Bioorganic & Medicinal Chemistry, vol. 15, No. 2, 2007, pp. 931-938.
Vinogradov, et al., "C-Terminal Modification of Fully Unprotected Peptide Hydrazides via in Situ Generation of Isocyanates," Organic Letters, vol. 18, No. 6, 2016, pp. 1222-1225.
Wang, et al., "Synthesis of peptide C-terminal derivatives using the transfer active ester condensation technique," Tetrahedron Letters, vol. 39, No. 47, 1998, pp. 8719-8720.

(56) References Cited

OTHER PUBLICATIONS

Akerblom, et al., "Six new photolabile linkers for solid-phase synthesis. 1. Methods of preparation," Molecular Diversity, vol. 3, No. 3, 1997, pp. 137-148.

Alsina and Albericio, "Solid-Phase Synthesis of CTerminal Modified Peptides," Biopolymers, vol. 71, 2003, pp. 454-477.

Amblard, et al., "Fundamental of Modern Peptide Synthesis," Methods in Molecular Biology, vol. 298, 2005, pp. 1-25.

Angell, et al., "Practical protocols for stepwise solid-phase synthesis of cysteine-containing peptides," Journal of Peptide Research, vol. 60, 2002, pp. 292-299.

Arbour, et al., "Epimerization-free access to C-terminal cysteine peptide acids, carboxamides, secondary amides, and esters via complimentary strategies," Chemical Science, vol. 9, 2018, pp. 350-355.

Arbour, et al., "Exploiting the MeDbz Linker To Generate Protected or Unprotected C-Terminally Modified Peptides," Chemistry A European Journal, vol. 23, No. 51, 2017, pp. 12484-12488.

Arbour, et al., "Recent advances in the synthesis of C-terminally modified peptides," Organic & Biomolecular Chemistry, vol. 18, No. 37, 2020, pp. 7253-7272.

Arbour, et al., "Sequence Diversification by Divergent C-Terminal Elongation of Peptides," J. Org Chem., vol. 83, No. 4, 2018, pp. 1797-1803.

Aussedat, et al., "Total Synthesis of the Alpha-Subunit of Human Glycoprotein Hormones: Toward Fully Synthetic Homogeneous Human Follicle-Stimulating Hormone," Journal of the American Chemical Society, vol. 134, 2012, pp. 3532-3541.

Bacsa, et al., "Solid-Phase Synthesis of Difficult Peptide Sequences at Elevated Temperatures: A Critical Comparison of Microwave and Conventional Heating Technologies," The Journal of Organic Chemistry, vol. 73, 2008, pp. 7532-7542.

Barany, et al., "Side-Chain Anchoring Strategy for Solid-Phase Synthesis of Peptide Acids with C-Terminal Cysteine," Biopolymers, vol. 71, No. 6, 2003, pp. 652-666.

Bedford, et al., "Amino acid structure and "difficult sequences" in solid phase peptide synthesis," International Journal of Peptide Research and Therapeutics, vol. 40, No. 3-4, 1992, pp. 300-307.

Blanco-Canosa & Dawson, "An efficient Fmoc-SPPS approach for the generation of thioester peptide precursors for use in native chemical ligation," Angewandte Chemie, vol. 47, No. 36, 2008, pp. 6851-6855.

Blanco-Canosa, et al., "Chemical Protein Synthesis Using a Second-Generation N-Acylurea Linker for the Preparation of Peptide-Thioester Precursors," Journal of the American Chemical Society, vol. 137, 2015, pp. 7197-7209.

Botti, et al., "Native chemical ligation using removable NAlpha-(1-phenyl-2-mercaptoethyl) auxiliaries," Tetrahedron Letters, vol. 42, 2001, pp. 1831-1833.

Brailsford, et al., "Total chemical synthesis of human thyroid-stimulating hormone (hTSH) Beta-subunit: Application of arginine-tagged acetamidomethyl (AcmR) protecting groups," Tetrahedron, vol. 74, No. 15, 2018, pp. 1951-1956.

Butterfield, et al., "Amyloid Beta-Peptide (1-42)-Induced Oxidative Stress in Alzheimer Disease: Importance in Disease Pathogenesis and Progression," Antioxidants & Redox Signaling, vol. 19, No. 8, 2013, pp. 823-835.

Carpino, et al., "Racemization Studies During Solid-Phase Peptide Synthesis Using Azabenzotriazole-Based Coupling Reagents," Tetrahedron Letters, vol. 35, No. 15, 1994, pp. 2279-2282.

Chen, et al., "Selective N-terminal functionalization of native peptides and proteins," Chemical Science, vol. 8, No. 4, 2017, pp. 2717-2722.

Cherkupally, et al., "Solid-phase peptide synthesis (SPPS), C-terminal vs. side-chain anchoring: a reality or a myth," Amino Acids, vol. 46, No. 8, 2014, pp. 1827-1838.

Choi, et al., "Light-controlled release of caged doxorubicin from folate receptor-targeting PAMAMdendrimer nanoconjugate," ChemComm, vol. 46, No. 15, 2010, pp. 2632-2634.

Clarke, "Protein Isoprenylation and Methylation at Carboxyl-Terminal Cysteine Residues," Annual Review of Biochemistry, vol. 61, 1992, pp. 355-386.

Clippingdale, et al., "The amyloid-beta peptide and its role in Alzheimer's disease," Journal of Peptide Science, vol. 7, No. 5, 2001, pp. 227-249.

Coin, "The depsipeptide method for solid-phase synthesis of difficult peptides," Journal of Peptide Science, vol. 16, No. 5, 2010, pp. 223-230.

Cruz, et al., "Invertebrate vasopressin/oxytocin homologs. Characterization of peptides from Conus geographus and Conus straitus venoms," Journal of Biological Chemistry, vol. 262, No. 33, 1987, pp. 15821-15824.

Dawson, et al., "Synthesis of proteins by native chemical ligation," Science, vol. 266, No. 5186, 1994, pp. 776-779.

De L. Milton, et al., "Prediction of Difficult Sequences in Solid-Phase Peptide Synthesis," Journal of the American Chemical Society, vol. 112, 1990, pp. 6039-6046.

Dettin, et al., "SPPS of difficult sequences A comparison of chemical conditions, synthetic strategies and on-line monitoring," Journal of Peptide Research, vol. 49, No. 1, 1997, pp. 103-111.

Diaz-Rodriguez, et al., "Synthesis of Peptides Containing C-Terminal Methyl Esters Using Trityl Side-Chain Anchoring: Application to the Synthesis of a-Factor and a-Factor Analogs," Organic Letters, vol. 14, No. 22, 2012, pp. 5648-5651.

Diaz-Rodriguez, et al., "Synthesis of Peptides Containing C-Terminal Esters Using Trityl Side-Chain Anchoring: Applications to the Synthesis of C-Terminal Ester Analogs of the *Saccharomyces cerevisiae* Mating Pheromone a-Factor," J. Org. Chem., vol. 80, No. 22, 2015, pp. 11266-11274.

Doh, et al., "Synthesis and evaluation of Ketorolac ester prodrugs for transdermal delivery," Journal of Pharmaceutical Sciences, vol. 92, 2003, pp. 1008-1017.

Elashal, et al., "Fmoc solid-phase synthesis of C-terminal modified peptides by formation of a backbone cyclic urethane moiety," ChemComm, vol. 52, No. 62, 2016, pp. 9699-9702.

Elashal, et al., "Serine promoted synthesis of peptide thioester-precursor on solid support for native chemical ligation," Chemical Science, vol. 8, No. 1, 2017, pp. 117-123.

Fang, et al., "A convenient approach to synthesizing peptide C-terminal N-alkyl amides," Biopolymers Peptide Science, vol. 96, No. 6, 2011, pp. 715-722.

Fernandez-Escamilla, et al., "Prediction of sequence-dependent and mutational effects on the aggregation of peptides and proteins," Nature Biotechnology, vol. 22, No. 10, 2004, pp. 1302-1306.

Fosgerau and Hoffmann, "Peptide therapeutics: current status and future directions," Drug Discovery Today, vol. 20, No. 1, 2015, pp. 122-128.

Garcia, et al., "o-Formylation of electron-rich phenols with dichloromethyl methyl ether and TiCl4," Tetrahedron Letter, vol. 44, 2003, pp. 4961-4963.

Gehrmann, et al., "Solution Structure of Alpha-Conotoxin ImI by 1H Nuclear Magnetic Resonance," Journal of Medicinal Chemistry, vol. 42, No. 13, 1999, 2364-2372.

Glenner and Wong, "Alzheimer's disease: initial report of the purification and characterization of a novel cerebrovascular amyloid protein," Biochemical and Biophysical Research Communications, vol. 120, No. 3, 1984, pp. 885-890.

Glomset, et al., "Prenyl proteins in eukaryotic cells: a new type of membrane anchor," Trends in Biochemical Sciences, vol. 15, No. 4, 1990, pp. 139-142.

Han, et al., "Occurrence and Minimization of Cysteine Racemization during Stepwise Solid-Phase Peptide Synthesis," Journal of Organic Chemistry, vol. 62, 1997, pp. 4307-4312.

Hansen, et al., "C-Terminally modified peptides via cleavage of the HMBA linker by O-, N- or S-nucleophiles," Organic and Biomolecular Chemistry, vol. 14, No. 12, 2016, pp. 3238-3245.

Hibino & Nishiuchi, "4-Methoxybenzyloxymethyl group, a racemization-resistant protecting group for cysteine in Fmoc solid phase peptide synthesis," Organic Letters, vol. 14, No. 7, 2012, pp. 1926-1929.

(56) References Cited

OTHER PUBLICATIONS

Hibino, et al., "Evaluation of acid-labile S-protecting groups to prevent Cys racemization in Fmoc solid-phase peptide synthesis," Journal of Peptide Science, vol. 20, No. 1, 2014, pp. 30-35.

Holmes, et al., "Extensive neurite outgrowth and active synapse formation on self-assembling peptide scaffolds," PNAS USA, vol. 97, No. 12, 2000, pp. 6728-6733.

Hrycyna & Clarke, "Farnesyl cysteine C-terminal methyltransferase activity is dependent upon the STE14 gene product in *Saccharomyces cerevisiae*," Molecular and Cellular Biology, vol. 10, No. 10, 1990, pp. 5071-5076.

Huang, et al., "Accelerated Fmoc solid-phase synthesis of peptides with aggregation-disrupting backbones," Organic and Biomolecular Chemistry, vol. 13, No. 5, 2015, pp. 1500-1506.

Hyde, et al., "Internal Aggregation during Solid Phase Peptide Synthesis. Dimethyl Sulfoxide as a Powerful Dissociating Solvent," Journal of the Chemical Society, 1992, pp. 1573-1575.

Isidro-Llobet, et al., "Amino Acid-Protecting Groups," Chemical Reviews, vol. 109, No. 6, 2009, pp. 2455-2504.

Jang, et al., "Disordered amyloidogenic peptides may insert into the membrane and assemble into common cyclic structural motifs," Chemical Society Reviews, vol. 43, No. 19, 2014, pp. 6750-6764.

Warrass, et al., "High-Resolution Magic Angle Spinning NMR Study of Resin-Bound Polyalanine Peptides," Journal of the American Chemical Society, vol. 122, No. 8, 2000, pp. 1789-1795.

White, et al., "Expediting the Fmoc Solid Phase Synthesis of Long Peptides Through the Application of Dimethyloxazolidine Dipeptides," Journal of Peptide Science, vol. 10, No. 1, 2004, pp. 18-26.

Wilson, et al., "A Fascinating Journey into History: Exploration of the World of Isonitriles En Route to Complex Amides," Angewandte Chemie, vol. 51, No. 12, 2012, pp. 2834-2848.

Wohr, et al., "Pseudo-Prolines as Solubilizing, Structure-Disrupting Protection Technique in Peptide Synthesis," Journal of the American Chemical Society, vol. 118, 1996, pp. 9218-9227.

Wohr, et al., "Pseudo-Prolines in Peptide Synthesis: Direct Insertion of Serine and Threonine Derived Oxazolidines in Dipeptides," Tetrahedron Letters, vol. 36, No. 22, 1995, pp. 3847-3848.

Wu, et al., "Thio-mediated two-component coupling reaction of carboxylic acids and isonitriles under mild conditions," Tetrahedron Letters, vol. 50, No. 14, 2009, pp. 1523-1525.

Yoshiya, et al., "O-Acyl isopeptide method: development of an O-acyl isodipeptide unit for Boc SPPS and its application to the synthesis of ABeta1-42 isopeptide," Journal of Peptide Science, vol. 20, No. 9, 2014, pp. 669-674.

Yu, et al., "Enhanced Coupling Efficiency in Solid-Phase Peptide Synthesis by Microwave Irradiation," Journal of Organic Chemistry, vol. 57, No. 18, 1992, pp. 4781-4784.

Zablocki, et al., "A novel series of orally active antiplatelet agents," Bioorganic & Medicinal Chemistry, vol. 3, No. 5, 1995, pp. 539-551.

Zahariev, et al., "Synthesis of 'difficul' peptides free of aspartimide and related products, using peptoid methodology," Tetrahedron Letter, vol. 47, 2006, pp. 4121-4124.

Zeng, et al., "Use of Fmoc-N-(2-hydroxy-4-methyoxybenzyl) amino acids in peptide synthesis," Journal of Peptide Science, vol. 49, 1997, pp. 273-279.

Zhang & Casey, "Protein prenylation: molecular mechanisms and functional consequences," Annual Review of Biochemistry, vol. 65, 1997, pp. 241-269.

Zhang, et al., "Peptide self-assembly in functional polymer science and engineering," Reactive & Functional Polymers, vol. 41, 1999, pp. 91-102.

Zhang, et al., "Solid-Phase Synthesis of C-Terminal Peptide Hydroxamic Acids," Journal of Combinatorial Chemistry, vol. 3, No. 2, 2001, pp. 151-153.

Zhang, et al., "Spontaneous assembly of a self-complementary oligopeptide to form a stable macroscopic membrane," PNAS USA, vol. 90, No. 8, 1993, pp. 3334-3338.

Zhang, et al., "Unusually stable beta-sheet formation in an ionic self-complementary oligopeptide," Biopolymers, vol. 34, No. 5, 1994, pp. 663-672.

Zhang, et al., Emerging biological materials through molecular self-assembly, Biotechnology Advances, vol. 20, No. 5-6, 2002, pp. 321-339.

Zinieris, et al., "Improved solid-phase peptide synthesis of "difficult peptides" by altering the microenvironment of the developing sequence," Tetrahedron Letters, vol. 47, 2006, pp. 6861-6864.

\* cited by examiner

General strategy for N to C SPPS using N-acyl ureas.

Synthesis of difficult sequences/specialized residues.

Traditional Fmoc C to N SPPS illustrated with a MeDbz linker.

Epimerization caused by oxazalone formation during activation of C-terminal carboxylic acids.

Application of N-acyl urea strategy for C-terminal functionalization of cysteine peptides to the synthesis of α-conotoxin ImI.

Boc–(GCCSDPRCAWRC)–MeDbz-Gly-Resin
  SAcm  SAcm
  STrt  STrt 1) activation
2) $NH_3$, DMF 1.5 h
3) TFA:TIPS:$H_2O$ (95:2.5:2.5)
(25% yield, 3 steps)

→ H–(GCCSDPRCAWRC)–$NH_2$
     SAcm  SAcm
     SH    SH

1% DMSO
$Na_2HPO_4$/$NaH_2PO_4$ buffer pH 8

→ [ H–(GCCSDPRCAWRC)–$NH_2$
      SAcm  SAcm
      S——————S ]

$I_2$ MeOH/$H_2O$
(52% yield, 2 steps)

→ H–(GCCSDPRCAWRC)–$NH_2$
     S——————S
     S——————S

*α-conotoxin ImI*

FIGURE 9

Evaluation of conversion and epimerization for non-NCL C-terminal peptide elongation.

| entry[a,b] | amino acid (X) | co-solvent | conversion (%)[c] | epimerization (%D-Ala)[d] |
|---|---|---|---|---|
| 1 | Ile (I) | $H_2O$ | 72 | <1 |
| 2 | Pro (P) | $H_2O$ | >99 | 2 |
| 3 | Pro (P) | *i*PrOH | 74 | <1 |
| 4 | Pro (P) | HFIP | >99 | <1 |

Synthesis of H-AA-Dbz derivatives from Fmoc amino acids.

Evaluation of stereointegrity at C terminus during activation of DbzOMe.

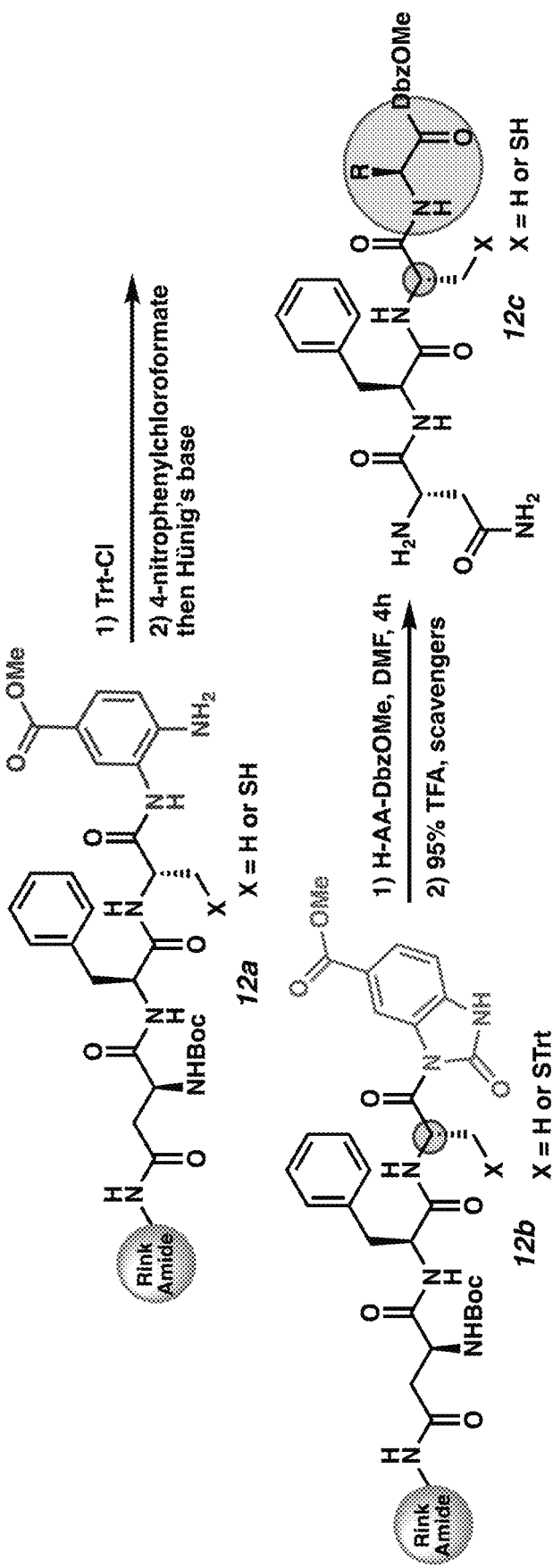
FIGURE 13. Evaluation of conversion and stereointegrity for all 20 H-AA-DbzOMe.
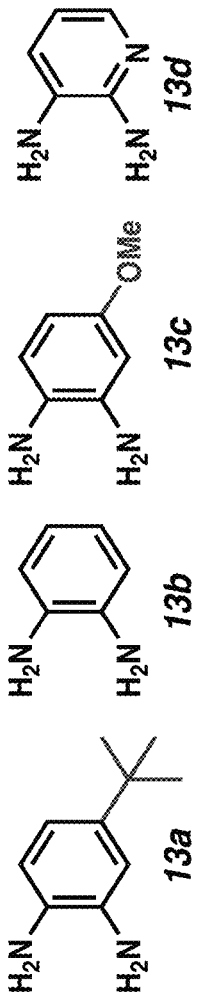
FIGURE 14. Commercially available diamines for altering the electronics of the aryl group in the N-acyl urea.

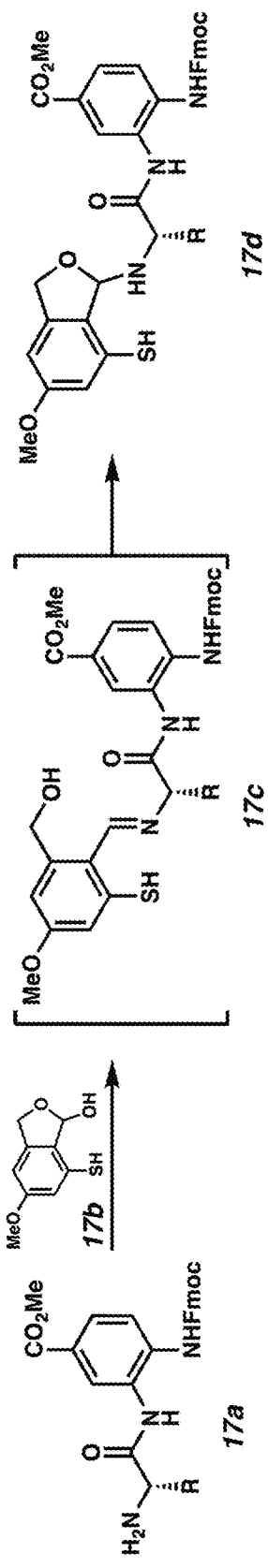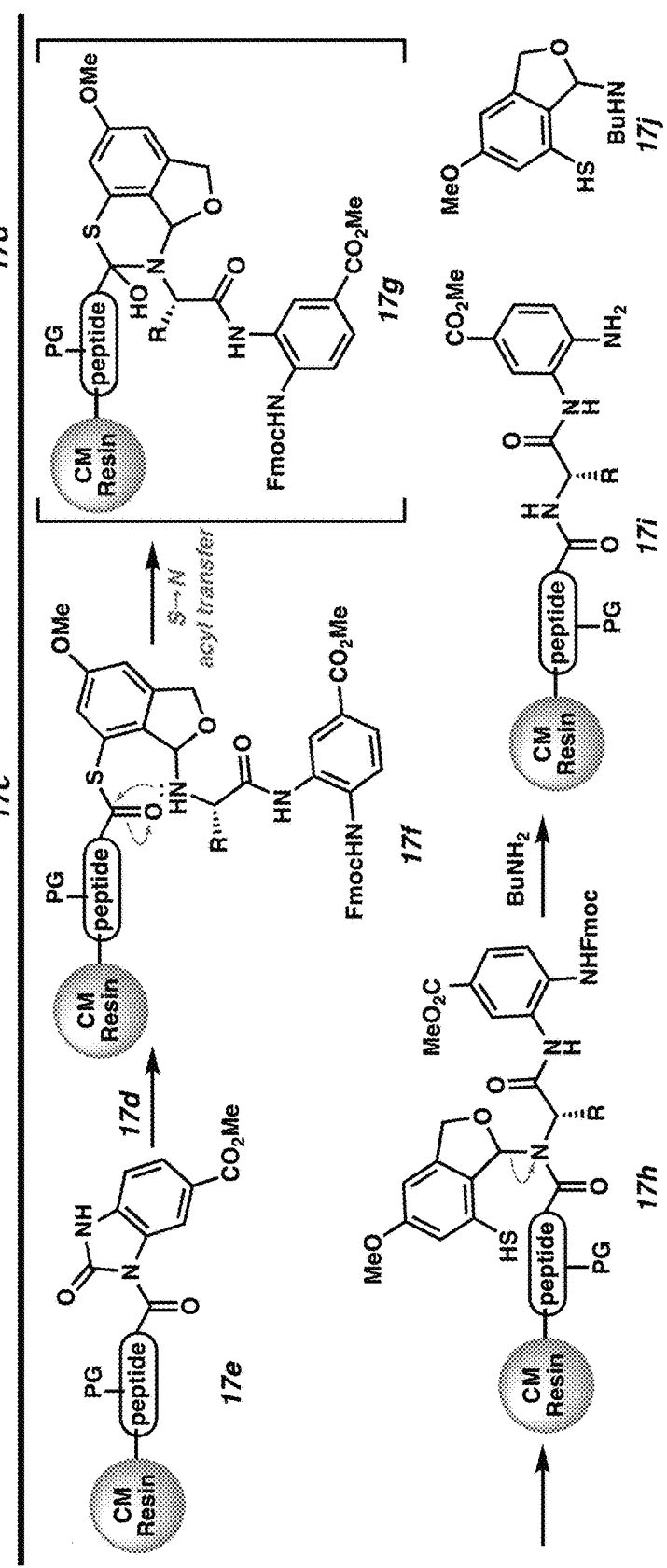
FIGURE 18A. Coupling reaction employing amine transfer agent for SPPS.
FIGURE 18B Peptides known to be difficult to prepare via C to N SPPS.

*18a:* Ac-(RADARADA)$_4$-NH$_2$  *18c:* Aβ(1-40)  *18e:* Ac-UPUAUAQUVUGLUPVUUQQFol

*18b:* Ac-(RARADADA)$_4$-NH$_2$  *18d:* H-VQAAIDYING-NH$_2$

U = α-aminoisobutyric acid
Fol = β-phenylalaninol

Synthesis of *O*-acyl linkage by resin-cleaving displacement of *MeNbz-Gly-Rink*.

Synthesis of O-acyl isodipeptide and pseudoproline dipeptides.

Access to protected or deprotected peptides via photolabile linker.

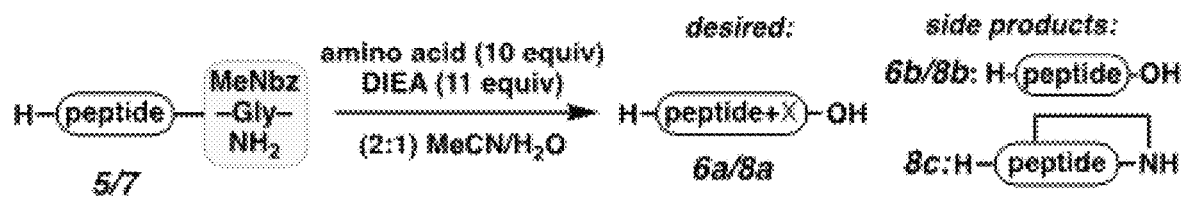

FIGURE 27A

| entry[a] | peptide | amino acid (X) | time (h) | conversion (%)[b] | a (%)[c] | b (%)[c] | c (%)[c] |
|---|---|---|---|---|---|---|---|
| 1 | AWA (5) | H-Gly (G) | 1 | >99 | >99 | <1 | n/a |
| 2 | AWA (5) | H-Ala (A) | 1 | >99 | 52 | 48 | n/a |
| 3 | AWA (5) | H-Pro (P) | 6 | >99 | 29 | 71 | n/a |
| 4 | AWA (5) | H-Ile (I) | 1 | >99 | >99 | <1 | n/a |
| 5 | AWA (5) | H-Trp (W) | 0.5 | >99 | >99 | <1 | n/a |
| 6 | AKTWA (7) | H-Gly (G) | 0.5 | >99 | >99 | <1 | <1 |
| 7 | AKTWA (7) | H-Ala (A) | 0.5 | >99 | <1 | <1 | >99 |
| 8 | AKTWA (7) | H-Ile (I) | 2 | >99 | 12 | 3 | 85 |
| 9 | AKTWA (7) | H-Pro (P) | 6 | >99 | <1 | <1 | >99 |

[a] All reactions were performed on 20 mg crude peptide in 300 μL solvent, rt = 24 ± 1 °C. [b] Conversion indicates degree of consumption of peptide-MeNbz-Gly-NH₂. [c] Based on relative ratio of HPLC-MS data.

FIGURE 27B

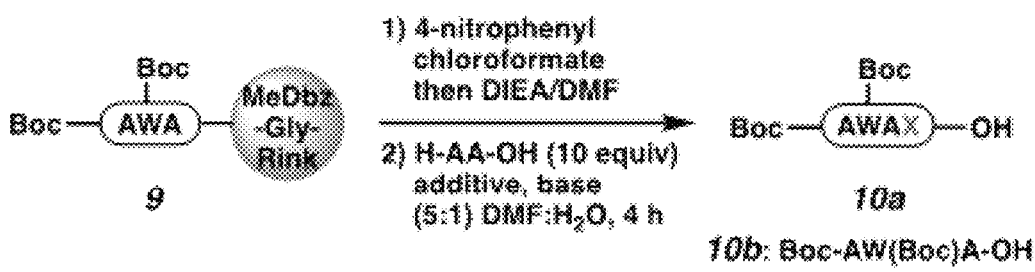

FIGURE 28A

| entry[a] | amino acid (X) | DIEA (equiv) | additive | % conversion[b] (% isolated yield)[c] | 10a:10b[d] |
|---|---|---|---|---|---|
| 1[e] | Gly (G) | 11 | – | 5 | >99:<1 |
| 2 | Gly (G) | 11 | – | 39 | 94:06 |
| 3 | Gly (G) | 21 | – | 76 | 91:09 |
| 4[f] | Gly (G) | 21 | NaSPh/HS(CH$_2$)$_3$CO$_2$Et | >99 | n.o. |
| 5 | Gly (G) | 21 | NaSPh | >99 (39[h]) | 94:06 |
| 6 | Ile (I) | 11 | – | 20 | 88:12 |
| 7 | Ile (I) | 21 | – | 72 | 88:12 |
| 8 | Ile (I) | 21 | NaSPh | 76 | 85:15 |
| 9[g] | Ile (I) | 21 | NaSPh/MPAA | 94 (22) | 90:10 |
| 10 | Ala (A) | 11 | – | 19 | 81:19 |
| 11 | Ala (A) | 21 | – | 77 | 77:13 |
| 12 | Ala (A) | 21 | NaSPh | 93 | 72:28 |
| 13[g] | Ala (A) | 21 | NaSPh/MPAA | 94 (29) | 86:14 |
| 14 | Pro (P) | 11 | – | 34 | 62:38 |
| 15 | Pro (P) | 21 | – | >99 (44[i]) | 88:12 |
| 16 | Pro (P) | 21 | NaSPh | 94 | 83:17 |
| 17[j] | Pro (P) | 21 | NaSPh | >99 | 87:13 |

[a] All reactions were conducted on 20 mg of resin in 600 μL (5:1) DMF:H$_2$O, rt = 24 ± 1 °C. [b] Conversion based on integration of remaining peptide on activated linker after nucleophile cleavage in MS data. [c] Yield based on final loading of (50-100 mg) WA-MeDbz-Gly-Rink Amide resin. [d] Relative ratios at 254 nm. [e] Reaction was conducted in 500 μL DMF. [f] 100 μL of ethyl-3-mercaptopropionate was used, giving exclusively the alkyl thioester. [g] A solution of 600 μL 5:1 DMF:modified NCL buffer (pH 7.2) was used. [h] Went to 73% conversion on a larger scale. [i] Went to 97% conversion on a larger scale. [j] Treated for 4 h twice.

FIGURE 28B

Epimerization of C-terminal alanine.

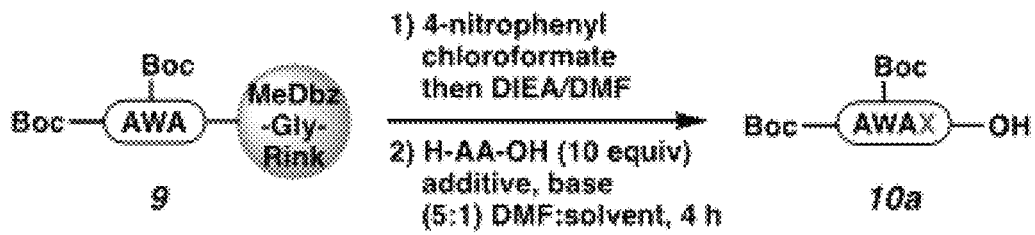

FIGURE 29A

| entry[a] | amino acid (X) | DIEA (equiv) | additive | solvent | % conversion[b] | epimerization (%D-Ala)[c] |
|---|---|---|---|---|---|---|
| 1 | Ile (I) | 21 | — | H₂O | 72 | <1 |
| 2[d] | Ile (I) | 21 | MPAA | Na₂HPO₄ (aq) | XX | XX |
| 3[d] | Ile (I) | — | NaSPh/MPAA | Na₂HPO₄ (aq) | XX | XX |
| 4[d] | Ile (I) | 21 | NaSPh/MPAA | Na₂HPO₄ (aq) | 94 | 14 |
| 5 | Pro (P) | 21 | — | H₂O | >99 | XX |
| 6 | Pro (P) | 21 | NaSPh | H₂O | 94 | 3 |

[a] All reactions were conducted on 10-20 mg of resin in 600 μL (5:1) DMF:solvent, rt = 24 ± 1 °C. [b] Conversion based on integration of remaining peptide on activated linker after nucleophile cleavage in MS data. [c] Relative ratios at 254 nm. [d] Na₂HPO₄ buffer at pH 7.2.

FIGURE 29B

LYRAGLRAY elongation to access protected peptide acids.

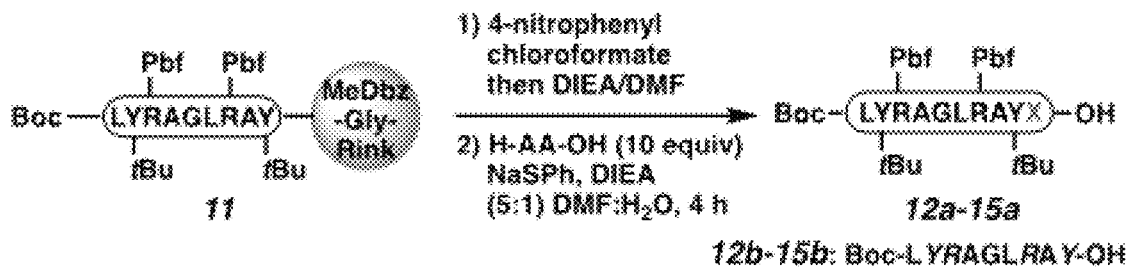

FIGURE 30A

| entry[a] | amino acid (X) | % conversion[b] (% isolated yield)[c] | product | a : b[d] |
|---|---|---|---|---|
| 1 | Gly (G) | >99 | LYRAGLRAYG (*12a*) | 91:09 |
| 2[e] | Ile (I) | >99 | LYRAGLRAYI (*13a*) | 74:26 |
| 3[e] | Ala (A) | >99 | LYRAGLRAYA (*14a*) | 79:21 |
| 4[f] | Pro (P) | >99 (9) | LYRAGLRAYP (*15a*) | 70:30 |

[a] All reactions were conducted on 20 mg of resin in 600 µL (5:1) DMF:H₂O, rt = 24 ± 1 °C.
[b] Conversion based on integration of remaining peptide on activated linker after nucleophile cleavage in MS data. [c] Yield based on initial loading of 100 mg of MeDbz-Gly-Rink Amide resin and represents 3 steps (SPPS, activation, and elongation). [d] Relative ratios at 254 nm. [e] Used 500 µL (5:1) DMF:modified NCL buffer containing MPAA, pH = 7.2. [f] Treated for 4 h twice.

FIGURE 30B

Table 5. Proline elongation solvent screen.

| entry[a] | solvent (HOR) | % conversion[b] | 15a : 15b : 15c[c] | | |
|---|---|---|---|---|---|
| 1 | TFE (HOCH$_2$CF$_3$) | >99 | 46 | 2 | 52 |
| 2 | MeOH (HOCH$_3$) | >99 | 95 | <1 | <1 |
| 3 | iPrOH (HOCH(CH$_3$)$_2$) | 97 | >99 | <1 | <1 |
| 4 | HFIP (HOCH(CF$_3$)$_2$) | >99 | 88 | 11 | <1 |

[a] All reactions were conducted on 30 mg of resin in 600 μL (5:1) DMF:solvent, rt = 24 ± 1 °C.
[b] Conversion based on integration of remaining peptide on activated linker after nucleophile cleavage in MS data. [c] Relative ratios at 254 nm.

Evaluation of C-terminal alanine epimerization with proline. A) D-Ala, B) L-Ala, and C) co-injection, gradient of 50% MeCN/H2O (0.1% HCOOH) over 15 min.

strategy for C-terminal peptide modification.

Access to C-terminally modified protected peptides by direct cleavage of MeNbz-linked peptides on resin.

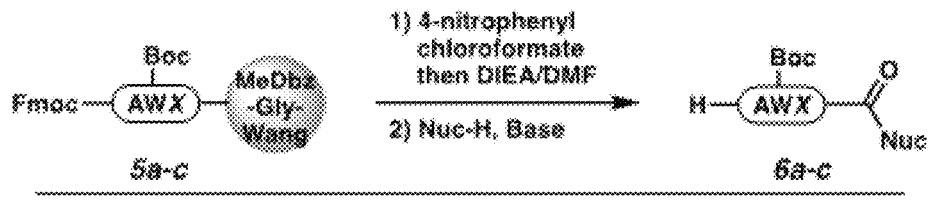

FIGURE 35A

| entry[a] | amino acid (X) | Nuc-H | base (5 equiv) | % conversion[b] (% isolated yield) |
|---|---|---|---|---|
| 1 | Gly | $NH_3$ | — | >99 (41) |
| 2 | Gly | $H_2N$-propyl | — | >99 |
| 3[c] | Gly | $H_2N$-(CH2)3-$N_3$ | — | >99 (30) |
| 4 | Gly | $H_2N$-CH2-C≡CH | — | >99 |
| 5 | Gly | $H_2N$-CH2-Ph | — | 98 |
| 6 | Gly | $H_2N$-Ph | DIEA | 53[d] |
| 7[e] | Gly | MeOH | KOtBu | >99 (41) |
| 8[e] | Gly | EtOH | KOtBu | >99 |
| 9 | Gly | i-PrOH | KOtBu | 62 |
| 10 | Gly | BnOH | KOtBu | 63 |
| 11[f] | Gly | PhOH | KOtBu | 98 |
| 12 | Gly | $H_2O$ | NaOH | >99 |
| 13 | Ile | $NH_3$ | — | >99 (68) |
| 14 | Ile | $H_2N$-propyl | — | >99 |
| 15[e] | Ile | MeOH | KOtBu | 96 |
| 16 | Arg(Pbf) | $NH_3$ | — | >99 |
| 17 | Arg(Pbf) | $H_2N$-propyl | — | >99 |
| 18[e] | Arg(Pbf) | MeOH | KOtBu | >99 |

[a] All reactions were conducted on 100 mg of resin at rt (24 ± 1 °C). [b] Conversion based on MS ratio of MeNbz-Gly and AWG-MeNbz-Gly. [c] A 0.7 M solution of Nuc-H in DMF (500 µL) was used. [d] N-terminus is Fmoc protected. [e] Incomplete removal of Fmoc was observed. [f] Reaction was conducted in MeCN.

FIGURE 35B

Scope of nucleophilic substitution of MeNbz in solution.

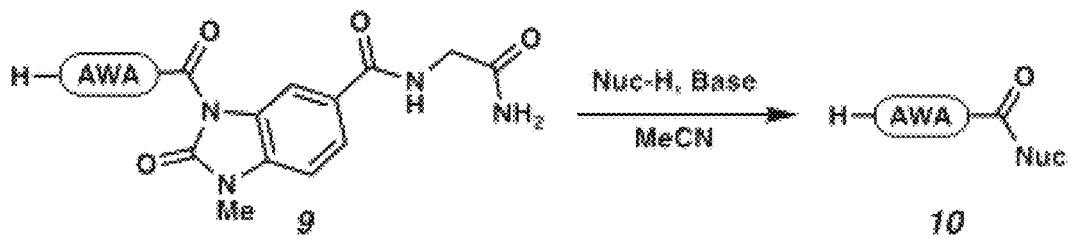

FIGURE 37A

| entry[a] | Nuc-H | base[b] | time (h) | conversion (%)[c] |
|---|---|---|---|---|
| 1 | H₂N-pentyl | — | 0.5 | >99 |
| 2[d] | H₂N-butyl-N₃ | — | 0.5 | >99 |
| 3 | H₂N-propargyl | — | 0.5 | >99 |
| 4 | H₂N-CH₂-Ph | — | 0.5 | >99 |
| 5 | H₂N-Ph | DIEA | 6 | >99 |
| 6 | H₂N-NH₂ | — | 0.5 | >99 |
| 7[e] | H₂N-OH | DIEA | 3 | >99 |
| 8[e] | MeNH-OMe | DIEA | 6 | 48 |
| 9 | MeOH | DIEA | 0.5 | >99 |
| 10 | EtOH | DIEA | 5 | >99 |
| 11 | BnOH | DIEA | 0.5 | >99 |
| 12[f] | PhOH | DIEA | 1 | >99 |
| 13 | i-PrOH | DIEA | 5 | 61 |
| 14 | H₂O | NaOH | 0.5 | >99 |
| 15[g] | NaBH₄ | — | 0.5 | >99 |

[a] All reactions were performed on 20 mg crude peptide in 200 μL MeCN at rt (24 ± 1 °C). [b] 5 equiv. unless noted. [c] Conversion based on MS data. [d] 10 equiv Nuc-H was first dissolved in 100 μL MeCN then added to the peptide mixture. [e] 5 equiv of the Nuc-HCl salt was used with 10 equiv base. [f] 10 equiv of PhOH was added directly to the peptide mixture. [g] Reaction was conducted in 200 μL THF, giving the C-terminal amino alcohol.

FIGURE 37B

Selectivity for intermolecular attack vs intramolecular attack.

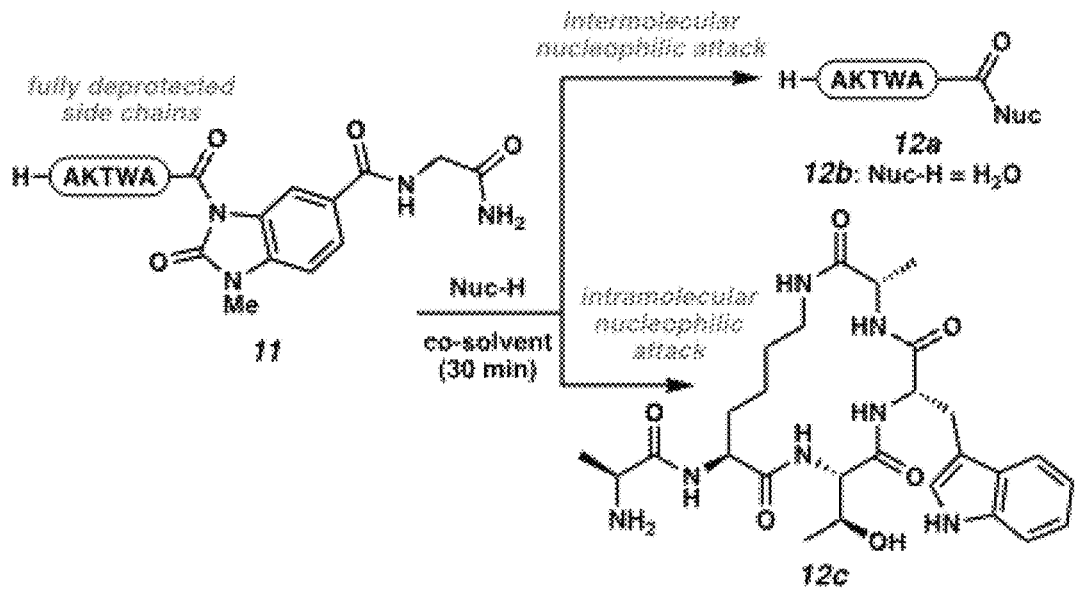

FIGURE 38A

| entry[a] | Nuc-H | base | co-solvent | 12a:12b:12c (%)[b] | | |
|---|---|---|---|---|---|---|
| 1 | H₂N-butyl | — | MeCN | >99 | — | — |
| 2[c] | H₂N-butyl | — | MeCN/H₂O | 93 | 7 | — |
| 3 | H₂N-propargyl | — | MeCN | >99 | — | — |
| 4 | H₂N-Ph | DIEA (5 equiv) | MeCN | 8 | — | 92 |
| 5 | H₂N-NH₂ | — | MeCN | >99 | — | — |
| 6[d] | H₂N-OH | DIEA (10 equiv) | MeCN | 82 | 18 | — |
| 7[d] | Me-N(Me)-O-Me | DIEA (10 equiv) | MeCN | — | 11 | 89 |
| 8 | MeOH | DIEA (5 equiv) | MeCN | 42 | — | 58 |
| 9[e] | — | DIEA (10 equiv) | MeCN | — | 9 | 91 |
| 10[f] | NaBH₄ | — | THF/MeCN | 77 | 23 | — |

[a]Unless noted, all reactions were performed on 20 mg crude peptide in 200 µL MeCN with 200 µL nucleophile at rt (24 ± 1 °C). [b]Relative ratio of MS data. [c]Performed in 200 µL each MeCN, H₂O, BuNH₂. [d]5 equiv of the Nuc·HCl salt was used and Hünig's base was increased accordingly. [e]Performed on 60 mg crude peptide in 600 µL MeCN. [f]Performed in 100 µL THF and 200 µL MeCN using 5 equiv NaBH₄.

FIGURE 38B

Selectivity for cyclization-prone substrates and evaluation of other nucleophilic side chains.

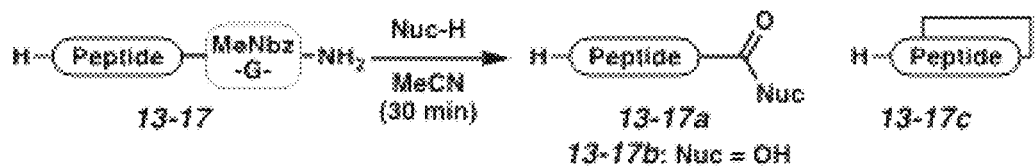

FIGURE 39A

| entry[a] | Peptide (13-17) | Nuc-H | base | solvent | a : b : c (%)[b] | | |
|---|---|---|---|---|---|---|---|
| 1 | AKTPWA (13) | H$_2$N~~~ | – | MeCN | >99 | – | – |
| 2 | AKTPWA | MeOH | DIEA (5 equiv) | MeCN | 39 | – | 61 |
| 3 | AKTPWA | – | DIEA (11 equiv) | MeCN | – | – | >99 |
| 4 | AKTGWA (14) | H$_2$N~~~ | – | MeCN | 97 | – | 3 |
| 5 | AKTGWA | MeOH | DIEA (5 equiv) | MeCN | 9 | – | 88 |
| 6 | AKTGWA | – | DIEA (11 equiv) | MeCN | – | – | >99 |
| 7 | ASTGWA (15) | H$_2$N~~~ | – | MeCN | >99 | – | – |
| 8 | ASTGWA | MeOH | DIEA (5 equiv) | MeCN | >99 | – | – |
| 9 | ASTGWA | – | DIEA (11 equiv) | MeCN | – | 65 | 35 |
| 10 | ACTGWA (16) | H$_2$N~~~ | – | MeCN | >99 | – | – |
| 11 | ACTGWA | MeOH | DIEA (5 equiv) | MeCN | >99 | – | – |
| 12 | ACTGWA | – | DIEA (11 equiv) | MeCN | – | 34 | 66 |
| 13 | AYTGWA (17) | H$_2$N~~~ | – | MeCN | >99 | – | – |
| 14 | AYTGWA | MeOH | DIEA (5 equiv) | MeCN | >99 | – | – |
| 15 | AYTGWA | – | DIEA (11 equiv) | MeCN | – | 19 | 81 |

[a]Unless noted, all reactions were performed on 5 mg crude peptide in 100 µL MeCN:H$_2$O (95:5) with 100 µL nucleophile at rt (24 ± 1 °C). [b]Relative ratio of MS data.

FIGURE 39B

Investigation of Ala epimerization.

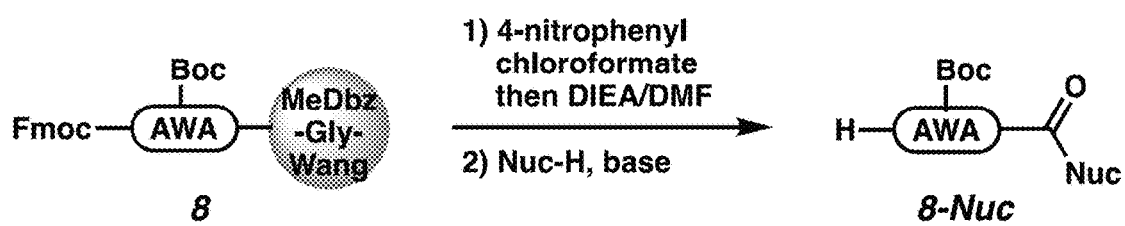

FIGURE 40A

| entry[a] | Nuc-H | base (5 equiv) | conversion (%)[b] | epimerization (% D-Ala) |
|---|---|---|---|---|
| 1[c] | BuNH$_2$ | – | >99 | N/A |
| 2[d] | MeOH | KOtBu | >99 | 15 |
| 3[d] | MeOH | DIEA | >99 | N/A |
| 4[d] | H$_2$O | DIEA | 70 | N/A |

[a] Unless otherwise noted, reactions were performed on 20 mg of resin containing all L amino acids in 200 µL of Nuc-H at rt (24 ± 1 °C), [b] Conversion based on MS ratio of MeNbz-Gly and AWG-MeNbz-Gly. [c]TFA:TIPS:H$_2$O (95:2.5:2.5) was used (PGs removed for assay), [d] Partial removal of Fmoc was observed. N/A = Below the limit of detection.

FIGURE 40B

Evaluation of epimerization during nucleophilic cleavage of the MeNbz group in C-terminal cysteine peptides.

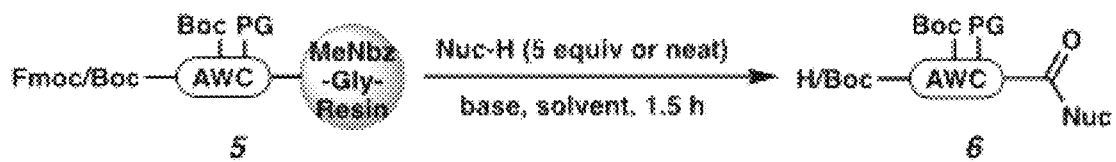

FIGURE 42A

| entry[a] | PG | Nuc-H | base (5 equiv) | solvent | % conversion | epimerization[b] (% D-X) |
|---|---|---|---|---|---|---|
| 1[c] | Trt | NH₃ | – | DMF | >99 | <1 |
| 2 | Trt | PhCH₂NH₂ | – | BnNH₂ | >99 | 16 |
| 3 | Trt | PhCH₂NH₂ | – | MeCN | >99 | <1 |
| 4 | Trt | BuNH₂ | – | BuNH₂ | >99 | 8 |
| 5 | Trt | BuNH₂ | – | DMF | >99 | 10 |
| 6 | Trt | BuNH₂ | – | MeCN | >99 | 9 |
| 7[c] | Acm | BuNH₂ | – | MeCN | >99 | <1 |
| 8[c] | Mob | BuNH₂ | – | MeCN | >99 | <1 |
| 9[c] | Bn | BuNH₂ | – | MeCN | >99 | <1 |
| 10 | StBu | BuNH₂ | – | MeCN | >99 | <1 |
| 11[c] | tBu | BuNH₂ | – | MeCN | >99 | <1 |
| 12[d] | Trt | MeOH | KOtBu | MeOH | >99 | 42 |
| 13 | Trt | MeOH | DIEA | MeOH | 65 | <1 |
| 14[e] | Trt | MeOH | – | MeOH/Na₂HPO₄(aq) | >99 | <1 |
| 15 | Trt | H₂O | DIEA | H₂O/MeCN | 56 | <1 |

[a] All reactions were performed on 20 mg of resin containing all L amino acids in 200 μL of solvent at ambient temperature (24 ± 1 °C). [b] all PGs were removed prior to epimerization assay unless otherwise noted. [c] Cys(PG) was intact during epimerization assay. [d] 0.7 equiv KOtBu. [e] Na₂HPO₄/NaH₂PO₄ buffer at pH = 8.

FIGURE 42B

Synthesis of conotoxin α-ImI (10).

FIGURE 43

C-terminal elongation by nucleophilic attack of cysteine on MeNbz.

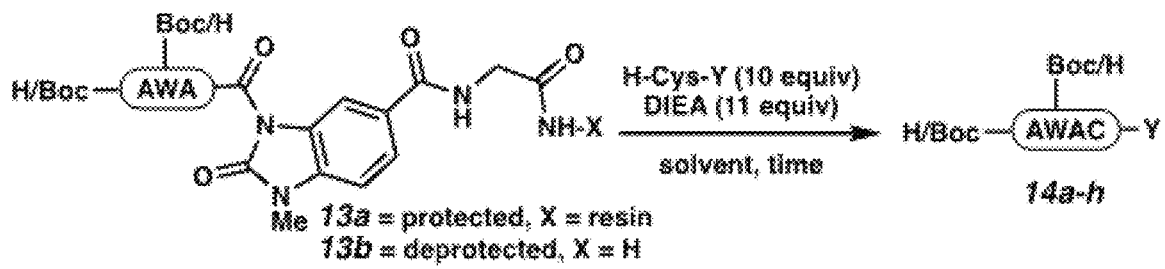

FIGURE 44A

| entry[a] | substrate | Y | solvent | time (h) | conversion (%)[b] |
|---|---|---|---|---|---|
| 1 | 13a | OH (*14a*) | (5:1) DMF:H$_2$O | 4 | >99 |
| 2 | 13a | OEt (*14b*) | DMF | 4 | >99 |
| 3 | 13a | NH$_2$ (*14c*) | DMF | 4 | >99 |
| 4[c] | 13a | NHBu (*14d*) | DMF | 4 | 38 |
| 5 | 13b | OH (*14e*) | (2:1) MeCN:H$_2$O | 0.5 | >99 |
| 6 | 13b | OEt (*14f*) | MeCN | 0.5 | >99 |
| 7 | 13b | NH$_2$ (*14g*) | MeCN | 0.5 | >99 |
| 8[c,d] | 13b | NHBu (*14h*) | (25:1) MeCN:H$_2$O | 0.5 | >99 |

[a] Unless noted, on-resin reactions were performed on 20 mg resin in 500 μL solvent, solution-phase reactions were performed on 20 mg crude peptide in 200 μL solvent, 100 μL of H$_2$O was added as indicated, rt = 24 ± 1 °C. [b] Conversion based on integration of relevant peaks in HPLC/MS data. [c] Cystine formation was observed. [d] Performed on 3.8 mg of *13* using 520 μL MeCN:H$_2$O.

FIGURE 44B

Table 3. Cysteine elongation to generate C-terminal acids, carboxamides, and esters.

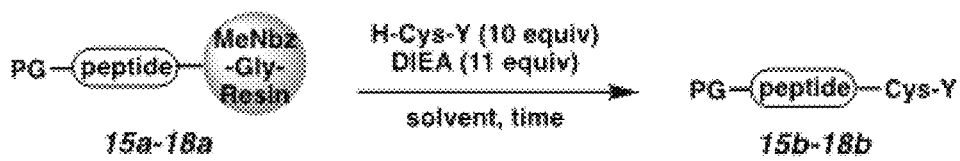

FIGURE 45A

| entry[a] | PG | peptide | Y | solvent | time (h) | conversion (%)[b] |
|---|---|---|---|---|---|---|
| 1[c,d] | H | AKTWA (15) | OH | (5:1) MeCN:H$_2$O | 0.5 | >99 |
| 2 | Boc | AKTWAP (16) | OH | (1:1) DMF:NCL buffer | 4 | 10 |
| 3[c,e] | H | AKTWAP (16) | OH | NCL buffer | 1 | >99 |
| 4 | Boc | LYRAGLRAY (17) | NH$_2$ | (1:1) DMF:NCL buffer | 4 | >99 |
| 5 | Boc | VGGVVI (18) | OMe | (1:1) DMF:NCL buffer | 4 | 10 |
| 6[c,f] | H | VGGVVI (18) | OMe | NCL buffer | 0.5 | >99 |

[a] Unless noted, on-resin reactions were performed on 20 mg resin in 500 μL solvent, rt = 24 ± 1 °C, NCL buffer at pH 7.2. [b] Based on integration of relevant peaks in HPLC/MS data. [c] Reaction performed in solution, unprotected. [d] Performed on 20 mg of 15a using 600 μL solvent. [e] Performed on 10 mg of 16a using 250 μL solvent. [f] Performed on 67.3 mg of 18a using 250 μL solvent.

FIGURE 45B

A) L-Cys, B) D-Cys, and C) Co-injection after SPPS, gradient: 40-95% MeCN/H₂O + 1% HCOOH over 15 min.

A) L-Cys after 24 h, B) 4 h, C) 2 h, and D) co-injection, gradient: 40-95% MeCN/H₂O + 1% HCOOH over 15 min.

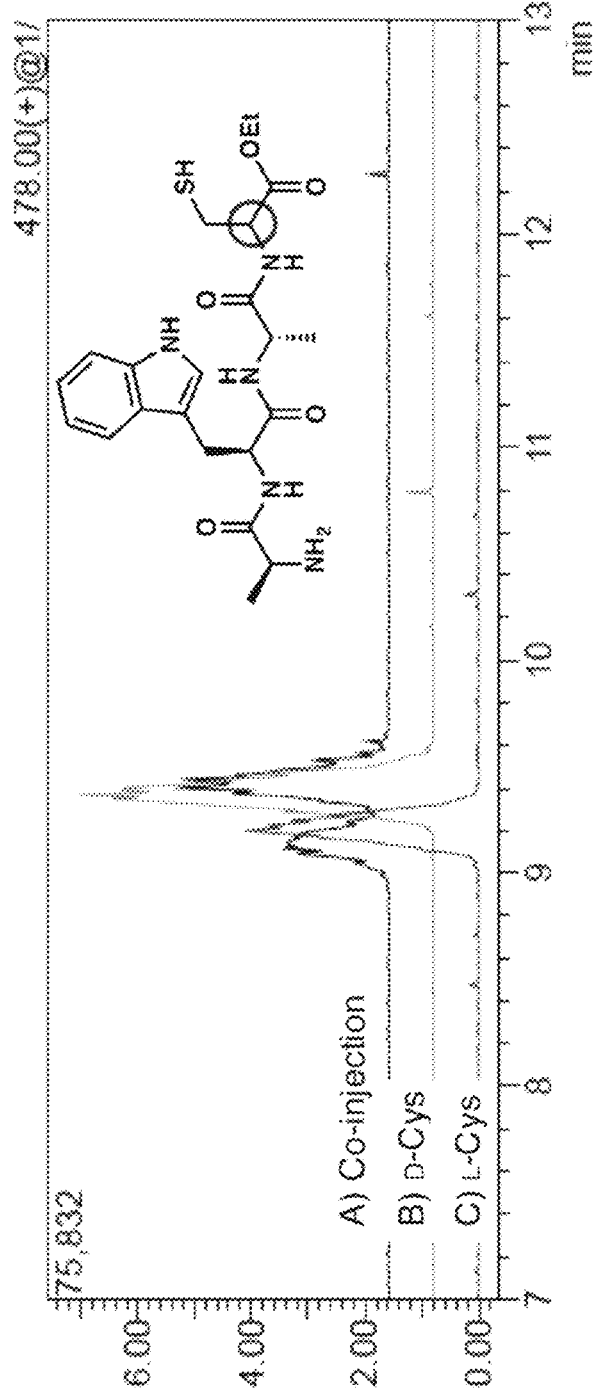
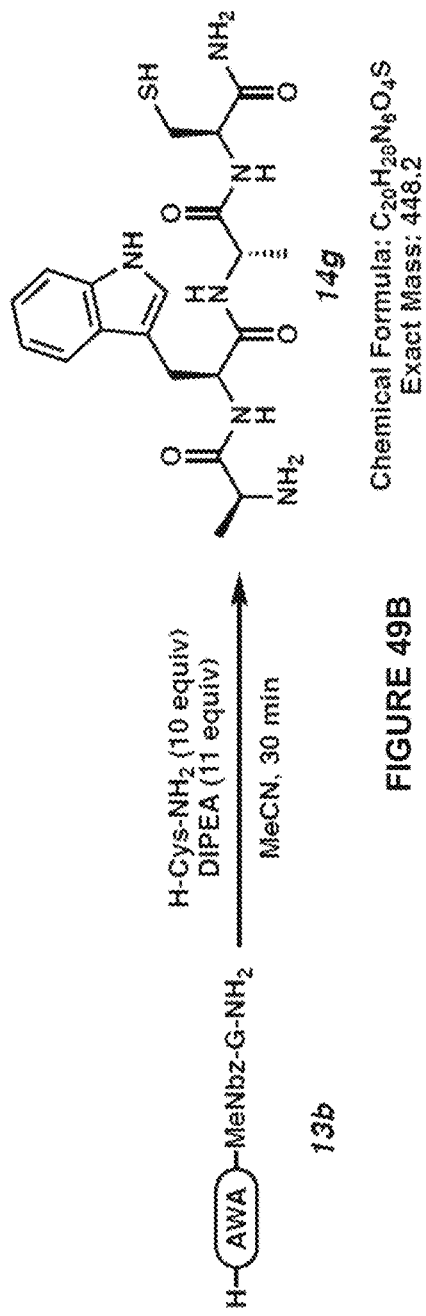
A) Co-injection, B) D-Cys, and C) L-Cys of in solution elongation of Cys-OEt, Gradient: 20-20(10 min)-45(5 min)% MeCN/H₂O + 1% HCOOH over 15 min.
FIGURE 49A
FIGURE 49B

SEQUENCE LISTING

```
<160> NUMBER OF SEQ ID NOS: 38

<210> SEQ ID NO 1
<211> LENGTH: 12
<212> TYPE: PRT
```

<213> ORGANISM: Artificial Sequence
<220> FEATURE:
<223> OTHER INFORMATION: Synthetic peptide

<400> SEQUENCE: 1

Gly Cys Cys Ser Asp Pro Arg Cys Ala Trp Arg Cys
1               5                   10

<210> SEQ ID NO 2
<211> LENGTH: 32
<212> TYPE: PRT
<213> ORGANISM: Artificial Sequence
<220> FEATURE:
<223> OTHER INFORMATION: Synthetic peptide

<400> SEQUENCE: 2

Arg Ala Asp Ala Arg Ala Asp Ala Arg Ala Asp Ala Arg Ala Asp Ala
1               5                   10                  15
Arg Ala Asp Ala Arg Ala Asp Ala Arg Ala Asp Ala Arg Ala Asp Ala
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: Synthetic peptide

<400> SEQUENCE: 3

Arg Ala Arg Ala Asp Ala Asp Ala Arg Ala Arg Ala Asp Ala Asp Ala
1               5                   10                  15
Arg Ala Arg Ala Asp Ala Asp Ala Arg Ala Arg Ala Asp Ala Asp Ala
            20                  25                  30

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide

<400> SEQUENCE: 4

Val Gln Ala Ala Ile Asp Tyr Ile Asn Gly
1               5                   10

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: mutagen
<222> LOCATION: (1)..(1)
<223> OTHER INFORMATION: Aib - alpha aminoisobutyric acid
<220> FEATURE:
<221> NAME/KEY: mutagen
<222> LOCATION: (3)..(3)
<223> OTHER INFORMATION: Aib - alpha aminoisobutyric acid
<220> FEATURE:
<221> NAME/KEY: mutagen
<222> LOCATION: (5)..(5)
<223> OTHER INFORMATION: Aib - alpha aminoisobutyric acid
<220> FEATURE:
<221> NAME/KEY: mutagen
<222> LOCATION: (8)..(8)
<223> OTHER INFORMATION: Aib - alpha aminoisobutyric acid
<220> FEATURE:
<221> NAME/KEY: mutagen

```
<222> LOCATION: (10)..(10)
<223> OTHER INFORMATION: Aib - alpha aminoisobutyric acid
<220> FEATURE:
<221> NAME/KEY: mutagen
<222> LOCATION: (13)..(13)
<223> OTHER INFORMATION: Aib - alpha aminoisobutyric acid
<220> FEATURE:
<221> NAME/KEY: mutagen
<222> LOCATION: (16)..(17)
<223> OTHER INFORMATION: Aib - alpha aminoisobutyric acid
<220> FEATURE:
<221> NAME/KEY: mutagen
<222> LOCATION: (20)..(20)
<223> OTHER INFORMATION: beta-phenylalaninol

<400> SEQUENCE: 5

Xaa Pro Xaa Ala Xaa Ala Gln Xaa Val Xaa Gly Leu Xaa Pro Val Xaa
1               5                   10                  15

Xaa Gln Gln Xaa
            20

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: absent or any amino acid

<400> SEQUENCE: 6

Leu Tyr Arg Ala Gly Leu Arg Ala Tyr Xaa
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: Xaa is N-acyl urea (MeNbz) linker or is absent
<220> FEATURE:
<221> NAME/KEY: MISC_FEATURE
<222> LOCATION: (11)..(11)
<223> OTHER INFORMATION: Gly can optionally have Rink attached

<400> SEQUENCE: 7

Leu Tyr Arg Ala Gly Leu Arg Ala Tyr Xaa Gly
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Leu Tyr Arg Ala Gly Leu Arg Ala Tyr Ile
1               5                   10

<210> SEQ ID NO 9
<211> LENGTH: 10
<212> TYPE: PRT
<213> ORGANISM: Artificial Sequence
```

```
<220> FEATURE:
<223> OTHER INFORMATION: Synthetic peptide

<400> SEQUENCE: 9

Leu Tyr Arg Ala Gly Leu Arg Ala Tyr Ala
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

Leu Tyr Arg Ala Gly Leu Arg Ala Tyr Pro
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Leu Tyr Arg Ala Gly Leu Arg Ala Tyr
1               5

<210> SEQ ID NO 12
<211> LENGTH: 30
<212> TYPE: PRT
<213> ORGANISM: Artificial Sequence
<220> FEATURE:
<223> OTHER INFORMATION: Synthetic peptide

<400> SEQUENCE: 12

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Synthetic peptide

<400> SEQUENCE: 13

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Ala
            20                  25                  30

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Cys Phe Ile Arg Asn Cys Pro Lys Gly
1               5
```

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Cys Phe Ile Arg Asn Cys Pro Lys Gly
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: mutagen
<222> LOCATION: (9)..(9)
<223> OTHER INFORMATION: Modified with 7-NHpropargyl

<400> SEQUENCE: 16

Cys Phe Ile Arg Asn Cys Pro Lys Gly
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: mutagen
<222> LOCATION: (9)..(9)
<223> OTHER INFORMATION: Methoxylated (7-OMe)

<400> SEQUENCE: 17

Cys Phe Ile Arg Asn Cys Pro Lys Gly
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic peptide

<400> SEQUENCE: 18

Ala Lys Thr Pro Trp Ala
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Ala Lys Thr Gly Trp Ala
1               5

<210> SEQ ID NO 20
<211> LENGTH: 6
<212> TYPE: PRT
<213> ORGANISM: Artificial Sequence
<220> FEATURE:

<223> OTHER INFORMATION: Synthetic peptide

<400> SEQUENCE: 20

Ala Ser Thr Gly Trp Ala
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

Ala Cys Thr Gly Trp Ala
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22

Ala Tyr Thr Gly Trp Ala
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic peptide

<400> SEQUENCE: 23

Ala Lys Thr Trp Ala
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide

<400> SEQUENCE: 24

Ala Lys Thr Trp Ala Pro
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic peptide

<400> SEQUENCE: 25

Val Gly Gly Val Val Ile
1               5

<210> SEQ ID NO 26
<211> LENGTH: 13
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<222> LOCATION: (12)..(12)
<223> OTHER INFORMATION: Xaa is N-acyl urea (MeNbz)linker

<400> SEQUENCE: 26

Tyr Ile Ile Lys Gly Val Phe Trp Asp Pro Ala Xaa Gly
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic peptide

<400> SEQUENCE: 27

Tyr Ile Ile Lys Gly Val Phe Trp Asp Pro Ala Cys
1               5                   10

<210> SEQ ID NO 28
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is methyl-diaminobenzoyl (MeDbz) linker

<400> SEQUENCE: 28

Ala Trp Cys Xaa Gly
1               5

<210> SEQ ID NO 29
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: mutagen
<222> LOCATION: (4)..(4)
<223> OTHER INFORMATION: Ethoxylated (-OEt)

<400> SEQUENCE: 29

Ala Trp Ala Cys
1

<210> SEQ ID NO 30
<211> LENGTH: 4
<212> TYPE: PRT
<213> ORGANISM: Artificial Sequence
<220> FEATURE:
<223> OTHER INFORMATION: Synthetic peptide

<400> SEQUENCE: 30

Ala Trp Ala Cys
1

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (4)..(4)
<223> OTHER INFORMATION: Xaa is methyl-diaminobenzoyl (MeDbz) linker
<220> FEATURE:
<221> NAME/KEY: MISC_FEATURE
<222> LOCATION: (5)..(5)
<223> OTHER INFORMATION: Gly can have a Rink attached

<400> SEQUENCE: 31

Ala Trp Ala Xaa Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is an N-acyl urea (MeNbz) linker or is
      absent
<220> FEATURE:
<221> NAME/KEY: MISC_FEATURE
<222> LOCATION: (5)..(5)
<223> OTHER INFORMATION: Gly can optionally have a Rink attached

<400> SEQUENCE: 32

Ala Trp Ala Xaa Gly
1               5

<210> SEQ ID NO 33
<211> LENGTH: 4
<212> TYPE: PRT
<213> ORGANISM: Artificial Sequence
<220> FEATURE:
<223> OTHER INFORMATION: Synthetic peptide

<400> SEQUENCE: 33

Ala Trp Ala Ile
1

<210> SEQ ID NO 34
<211> LENGTH: 4
<212> TYPE: PRT
<213> ORGANISM: Artificial Sequence
<220> FEATURE:
<223> OTHER INFORMATION: Synthetic peptide

<400> SEQUENCE: 34

Ala Trp Ala Trp
1

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: (6)..(6)
<223> OTHER INFORMATION: N-acyl urea (MeNbz)

<400> SEQUENCE: 35

Ala Lys Thr Trp Ala Xaa Gly
1               5

<210> SEQ ID NO 36
```

```
<211> LENGTH: 6
<212> TYPE: PRT
<213> ORGANISM: Artificial Sequence
<220> FEATURE:
<223> OTHER INFORMATION: Synthetic peptide

<400> SEQUENCE: 36

Ala Lys Thr Trp Ala Cys
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic peptide

<400> SEQUENCE: 37

Ala Lys Thr Trp Pro Cys
1               5

<210> SEQ ID NO 38
<211> LENGTH: 4
<212> TYPE: PRT
<213> ORGANISM: Artificial Sequence
<220> FEATURE:
<223> OTHER INFORMATION: Synthesized peptide

<400> SEQUENCE: 38

Ala Trp Ala Cys
1
```

EPIMERIZATION-FREE N TO C SOLID-PHASE PEPTIDE SYNTHESIS

CROSS REFERENCE TO RELATED APPLICATIONS

This application claims the benefit of U.S. Provisional Patent Application No. 62/720,668, filed on Aug. 21, 2018, which is hereby incorporated by reference in its entirety.

STATEMENT REGARDING FEDERALLY SPONSORED RESEARCH OR DEVELOPMENT

This invention was made with government support under grant R00GM097095 awarded by the National Institutes of Health. The government has certain rights in the invention.

REFERENCE TO SEQUENCE LISTING

The amino acid sequences described herein are shown using standard letter abbreviations, as defined in 37 C.F.R. § 1.822. A computer readable text file, entitled March1Seq_Listing ST25.txt" created on or about Mar. 1, 2022, with a file size of 9,795 bytes, contains the sequence listing for this application and is hereby incorporated by reference in its entirety.

BACKGROUND

Peptides are gaining increasing importance and prevalence as pharmaceuticals, especially in targeting difficult biological targets such as protein-protein interactions (PPIs).[1] Chemical synthesis remains the method of choice to access most peptide-derived pharmaceuticals on a commercial scale, despite ongoing advances in recombinant gene expression technologies, yet current solid-phase peptide synthesis (SPPS) methods are plagued by a variety of problems from cost to excessive, hazardous waste to regulatory challenges.[2]

The standard method for the chemical synthesis of peptides is solid-phase peptide synthesis (SPPS) starting with the amino acid on the C-terminal end of the peptide. In FIG. 1, this process is illustrated using the commercially available MeDbz linker (see compound 1) and Fmoc SPPS. First, the linker is loaded with the N-protected C-terminal amino acid (i.e., 3) using an expensive coupling agent such as HATU (2). An excess of both 2 and 3 are required for good conversion to the loaded resin (4). The N-terminal protecting group (Fmoc in 4) is removed. For Fmoc SPPS, piperidine is generally used to remove the N-protection. Next, the next amino acid (heading toward the N terminus in the sequence) is activated and coupled. This process is repeated until the full peptide sequence is elaborated (i.e. 5 is made). When MeDbz linker is used, it must be activated (usually with 4-nitrophenylchloroformate then Hünig's base), forming MeNbz-linked peptide 6 prior to cleavage with 95% trifluoroacetic acid (TFA) and scavengers from Rink or Wang resin.

Problem 1: Coupling—Reagents 2 and 3 are expensive, must be used in excess, and unreacted ⅔ cannot be recovered and reused.

Problem 2: Deprotection—Piperidine causes a variety of side reactions in the synthesis of complex peptides (formation of dehydroalanine, aspartim ides, epimerization of cysteine residues, etc.). During Boc SPPS, the Boc group is removed after each coupling with TFA, but the side chain protecting groups are cleaved and the peptide is removed from the resin using HF, which is a highly toxic and exceptionally corrosive gas.

Problem 3: Modification—It is difficult to make modifications to the C-terminus of a carboxylic acid-terminated peptide without epimerization of the C-terminal amino acid, which is induced by oxazolone formation.

Because of the problems mentioned above, researchers in the field of peptide synthesis have been looking for ways to accomplish N to C SPPS for many years, but when activating the C-terminal carboxylic acid beyond the 2nd amino acid in a sequence, oxazolone formation is difficult to avoid. When the oxazolone is formed, the acidity of the hydrogen at the α-position in the amino acid is increased. Typically, the coupling conditions are basic enough to cause deprotonation of this hydrogen, and upon reprotonation, the stereointegrity of the α-center is lost. This stereocenter is critical to the biological activity of the peptide.

Many of these issues could be resolved by a reliable method for SPPS in the N to C direction. However, despite decades of efforts,[3] no N to C strategy for SPPS has been reported that can avoid epimerization and diketopiperazine formation during activation of the C-terminal residue during peptide elongation. Thus, there remains a critical need for mild activation strategies that will enable SPPS in the N to C direction.

SUMMARY OF THE DISCLOSURE

This Summary is not intended to identify key features or essential features of the claimed subject matter, nor is it intended to be used to limit the scope of the claimed subject matter.

The present disclosure describes a novel method for synthesizing peptides in the N to C direction which proceed without epimerization and diketopiperazine formation. The method includes synthesizing a series of derivatized amino acids, for example, amino acid diaminobenzoyl derivatives or amino acid diamino-aryl derivatives. These derivatized amino acids are employed in the synthesis of the peptide. The unreacted derivatized amino acids are recovered and reused.

The method includes attaching the first derivatized amino acid to a resin prior to coupling a second amino acid to the carboxyl group of the first amino acid. In embodiments, attaching the first derivatized amino acid to the resin comprises anchoring the α-amino group or a side-chain of the first amino acid to the resin.

The method further includes activating the first amino acid to form a first amino acid including an N-acyl urea group and coupling a derivatized second amino acid to displace the N-acyl urea group on the first amino acid at its C-terminus to obtain a peptide. Repetition of activation of the peptide and coupling with other derivatized amino acid provides for elongation to form a peptide of desired length with a terminal N-acyl urea group. Subsequently, the peptide can be cleaved from the resin by acidic resin cleavage to obtain C-terminally functionalized unprotected peptide or by nucleophilic resin cleavage to obtain C-terminally functionalized protected peptide.

In contrast to peptide synthesis from C to N direction, the novel method employs N-acyl urea which is a very mild carbonyl activating agent to enable N to C direction peptide synthesis that is epimerization free.

BRIEF DESCRIPTION OF THE SEVERAL VIEWS OF THE DRAWINGS

FIG. 9. Application of N-acyl urea strategy for C-terminal functionalization of cysteine peptides to the synthesis of α-conotoxin Iml. FIG. 9 illustrates SEQ ID NO: 1.

FIG. 13. Evaluation of conversion and stereointegrity for all 20 H-AA-DbzOMe.

FIG. 14. Commercially available diamines for altering the electronics of the aryl group in the N-acyl urea.

FIGS. 18A and 18B. Coupling reaction employing amine transfer agent for SPPS.

FIGS. 27A and 27B. Solution phase C-terminal peptide elongation.

FIGS. 28A and 28B. On-resin elongation to access protected peptide acids.

FIGS. 29A and 29B. Epimerization of C-terminal alanine.

FIGS. 30A and 30B. LYRAGLRAY (SEQ ID NO: 11) elongation to access protected peptide acids. FIG. 30A illustrates SEQ ID NO: 6; FIG. 30B lists SEQ ID NOs: 7-10.

FIG. 31A illustrates SEQ ID NOs: 11 and 10.

FIG. 32 illustrates SEQ ID NOs: 12 and 13.

FIGS. 35A and 35B. Access to C-terminally modified protected peptides by direct cleavage of MeNbz-linked peptides on resin.

FIG. 36 illustrates SEQ ID NOs: 14-17.

FIGS. 37A and 37B. Scope of nucleophilic substitution of MeNbz in solution.

FIGS. 38A and 38B. Selectivity for intermolecular attack vs. intramolecular attack. Peptide 11 corresponds to residues 1-5 of SEQ ID NO: 23.

FIGS. 39A and 39B. Selectivity for cyclization-prone substrates and evaluation of other nucleophilic side chains. FIG. 39B lists SEQ ID NOs: 18-22.

FIGS. 40A and 40B. Investigation of alanine epimerization.

FIGS. 42A and 42B. Evaluation of epimerization during nucleophilic cleavage of the MeNbz group in C-terminal cysteine peptides.

FIG. 43. Synthesis of conotoxin α-Iml (10) (SEQ ID NO: 1).

FIGS. 44A and 44B. C-terminal elongation by nucleophilic attack on MeNbz.

FIGS. 45A and 45B. Cysteine elongation to generate C-terminal acids, carboxamides, and esters. FIG. 45B lists SEQ ID NOs: 23, 24, 11, and 25.

FIG. 6 illustrates SEQ ID NOs: 26 and 27.

FIG. 48 illustrates SEQ ID NO: 28.

FIGS. 49A and 49B. Co-injection, D-Cys, and L-Cys in solution elongation of Cys-OEt, Gradient: 20-20(10 min)-45(5 min) % MeCN/H$_2$O+1% HCOOH over 15 min. 10 equiv H-Cys-NH$_2$ was weighed out into a vial containing a stir bar. 20 mg of crude peptide (13b) was dissolved in 200 μL of HPLC grade MeCN and added to the amino acid containing vial. 11 equiv of freshly distilled DIEA was added to the vial and allowed to stir at ambient temperature for 30 min. After 30 min, the reactions were quenched in 20% MeCN/H$_2$O (1% TFA) and analyzed via RP-HPLC-MS. FIG. 49A illustrates SEQ ID NO: 29, and FIG. 49B illustrates SEQ ID NO: 30.

DETAILED DESCRIPTION

Peptides are becoming increasingly important pharmaceutical targets as classically "druggable" targets dwindle and methods for peptide synthesis, delivery, and penetration through the cell membrane continue to improve.[1] As peptides become more accepted as viable pharmaceutical compounds and are more widely employed, methods for their synthesis will be subject to increasing scrutiny. The standard method for solid-phase peptide synthesis (SPPS) proceeds from the C terminus to the N terminus and suffers from several drawbacks. Excess of both the incoming fluorenylmethoxycarbonyl (Fmoc)- or t-butoxycarbonyl (Boc)-protected amino acid (AA) and the coupling agent are needed, and neither component is recoverable. Successive exposure to piperidine in Fmoc SPPS can induce problematic side reactions, leading to impurities that are often difficult to separate. Meanwhile, Boc SPPS requires trifluoroacetic acid (TFA) to remove the N-protecting group after every amino acid addition and requires HF for side-chain deprotection. For industrial scale synthesis, the huge amount of waste associated with C to N SPPS as well as issues such as solvent selection and environmental impact are major sources of added cost that are ultimately translated to the general public through increased cost of prescription drugs.[6]

For decades, it has been widely recognized in the field of peptide synthesis that many of these limitations could be reduced or avoided by the use of N to C peptide synthesis.[3] However, no method for accomplishing SPPS in this direction has been able to overcome the formation of oxazolone during the activation of the C terminus, leading to epimerization of the activated residue.

The inventors surprisingly discovered a novel method for peptide synthesis that solves the problems associated with peptide synthesis while making the synthesis of peptides on the solid phase more efficient, environmentally friendly, and industrially viable. The activating reagents used are inexpensive, and the individual amino acids can be recovered and reused. Based on developed C-terminal modification chemistry, which activates the C terminus of peptides without oxazolone-induced epimerization,[4,5] the novel method of peptide elongation proceeds without epimerization of the C-terminal residue.

Figure 1:
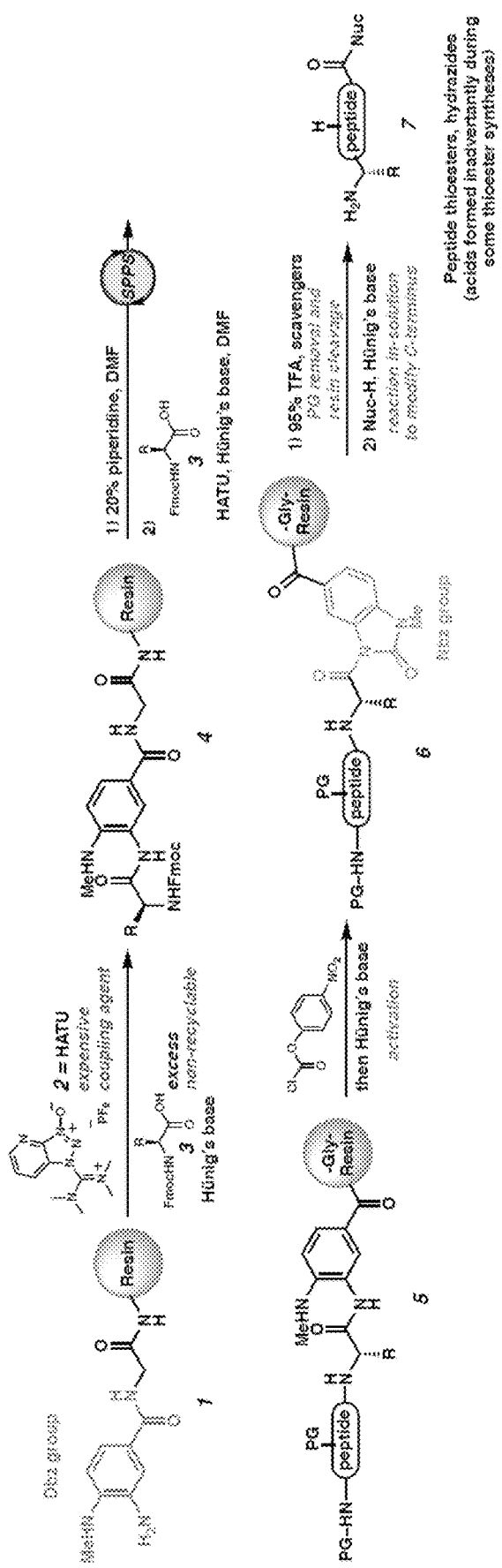
FIG. 1. General strategy for C to N SPPS using MeDbz linker.
Figure 2:
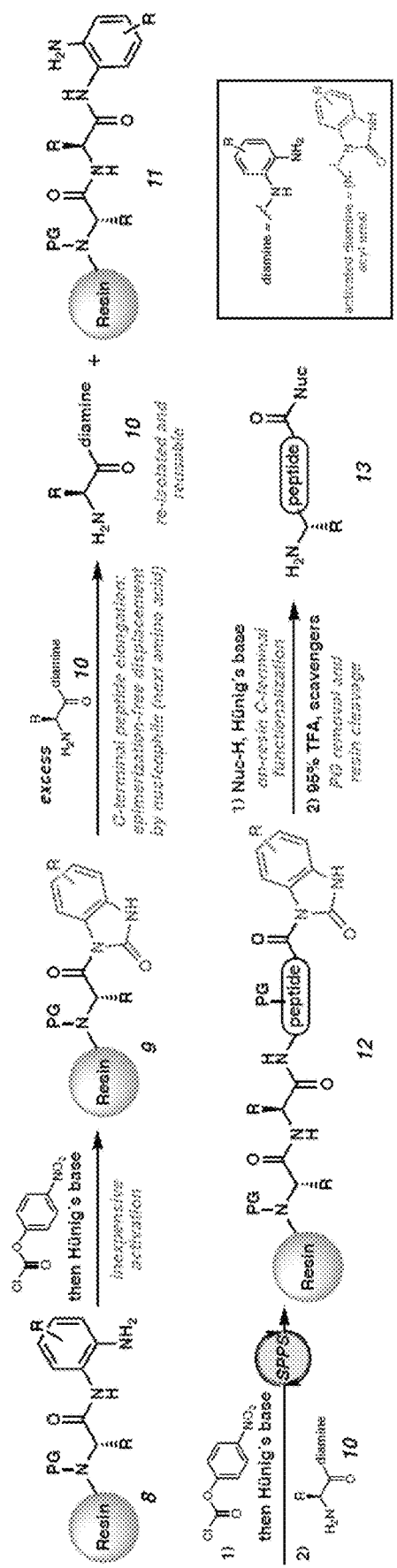
FIG. 2. General strategy for N to C SPPS using N-acyl ureas.

The present disclosure describes a novel process for N to C SPPS, which does not cause epimerization of the C-terminal amino acid. The novel process is shown in FIG. 2. The process includes synthesizing a series of amino acids (10) bearing an aryl diamine functionality (see box of FIG. 2) on the C-terminus. The process also includes linking the first (N-terminal) amino acid through the N atom to the resin and then protecting the first amino acid as a carbamate (peptide 8, PG=a carboxamide). Activation with the inexpensive 4-nitrophenyl chloroformate and other phosgene equivalents leads to the N-acyl urea (light gray group in 9). This N-acyl urea is displaced by the next amino acid (10), which already bears a C-terminal diamine to form an elongated peptide (11). The excess amino acid (10) is filtered off, and because it is not chemically modified during the coupling reaction, the unreacted amino acid can be recovered and made available for reuse. In embodiments, repeating this activation and displacement process provides the final peptide sequence (12). The C terminus is then converted to a desired functional group. Removal of the carboxamide protecting group and side chain protecting groups, and cleavage from the resin can provide the peptide.

The advantages of the novel process include the following:
  (1) Coupling—The coupling reagents used in this process are inexpensive, and the individual amino acids can be recovered and reused. C-terminal modification chemistry supports the feasibility of accomplishing this method of peptide elongation without epimerization of the C-terminal residue. Conditions to avoid epimerization of cysteine, which is the most epimerization-prone residue are described.
  (2) Deprotection—There is no deprotection step required during the iterative SPPS via the disclosed strategies.
  (3) C-terminal modification—The C-terminus can be functionalized in a variety of ways at the end of the SPPS.

Furthermore, bidirectional synthesis[7] is enabled by employing a sequence-appropriate side-chain anchoring strategy, allowing an unprecedented degree of flexibility in terms of synthesizing a variety of sequence variations for biological evaluation. As an example, by employing a sequence-appropriate side-chain anchoring strategy, Fmoc or Boc SPPS can be used to elongate in the C to N direction, then upon completion of that portion of the peptide, the N to C elongation can be used. This allows an unprecedented degree of flexibility in terms of synthesizing a variety of sequences for, for example, biological evaluation.

Additionally, by avoiding repetitive treatment with strong bases (i.e., piperidine) during SPPS, common pitfalls such as the formation of aspartimide, dehydroalanine, and piperidinylalanine side products are avoided.

The present disclosure describes synthesis of peptides from the N to C direction and enables synthesis of peptides of various length including peptides having 3 to 50 amino acids, 5 to 45 amino acids, 10 to 40 amino acids, 15 to 35 amino acids, 20 to 30 amino acids, or 20 to 25 amino acids.

The present disclosure describes the use of aromatic diamines/N-acyl ureas as exceptionally mild carbonyl activating agents to enable epimerization-free SPPS in the N to C direction. Examples of N-acyl ureas include Nbz and MeNbz or any cyclic urea fused to an aromatic ring, including heterocyclic rings. This is supported by the finding that a C-terminal aryl-fused N-acyl urea can be displaced by a variety of nucleophiles without detectable epimerization of the C-terminal residue, even for epimerization-prone amino acids such as Cys and His, and without diketopiperazine formation.[4] Additionally, it was established that a variety of amino acids are competent nucleophiles in displacing the N-acyl urea (MeNbz).[5]

The present disclosure also describes novel tools for the efficient synthesis of bioactive peptides and a suite of protocols for peptide synthesis in the N to C direction. The use of aromatic diamines/N-acyl ureas, such as aryl diamines/N-acyl ureas, to accomplish this goal is innovative as it is based on the finding that N-acyl ureas are among the mildest known activated carboxylic acid derivatives, while exploiting the latent reactivity of aryl diamines.

Moreover, the present disclosure describes N to C peptide synthesis using various methods including solid-phase, solution-phase, fluorous phase peptide synthesis (FPPS), and other known phases for peptide synthesis. As an example, in FPPS, the N terminus is anchored to a fluorous phase. These may be conducted using any solvent, including ionic liquids.

Figure 3:
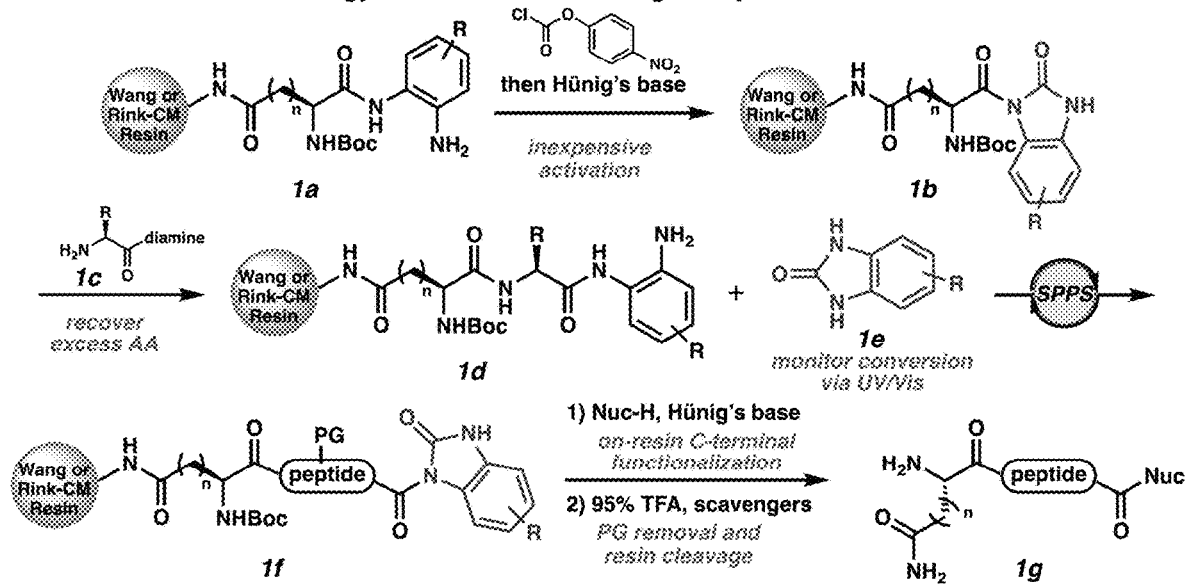
FIG. 3. General Strategy for N to C SPPS using N-acyl ureas.

Further, the present disclosure describes a strategy for N to C that is innovative because it takes advantage of the discovery that the aromatic-appended N-acyl urea, such as aryl-appended N-acyl urea is among the mildest carboxylic acid activation methods currently available. Additionally, employing amides of diamino-aromatic species (including heterocyclic species) rather than a protected carboxylic acid on the incoming amino acid avoids the need for an orthogonal protecting group scheme and replaces expensive coupling agents with a simple activation step. Perturbation of the aryl group's electronics are also described, including the use of other aromatic rings in place of C6H6, to tune the reactivity of the activated species in case any epimerization is observed. FIG. 3 provides an exemplary strategy for peptide synthesis in the N to C direction.

The present disclosure provide data supporting the discovery of the feasibility of N to C peptide elongation without epimerization. Key parameters such as the presence of added thiol or exogenous base that modulate reaction conversion and epimerization in model studies have been identified. In embodiments, the present disclosure describes establishing the reactivity profile of amino acids during N to C SPPS using N-acyl urea activation (FIG. 3) by synthesizing the full set of 20 amino acid diamines and determining the best conditions for each to maximize conversion while avoiding epimerization.

Figure 4:
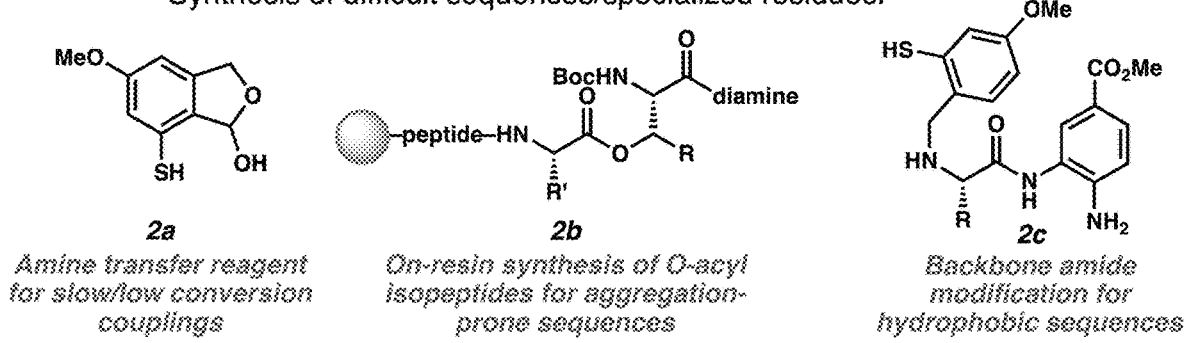
FIG. 4. Synthesis of difficult sequences/specialized residues.

Moreover, the present disclosure describes a strategy for overcoming poor coupling reactions by harnessing the exceptional nucleophilicity of sulfur to avoid basic conditions while facilitating coupling by S to N acyl transfer. The reason is that peptide properties vary wildly from sequence to sequence with weak predictability. Certain amino acid derivatives or sequences require specialized conditions to achieve high conversion and/or to avoid epimerization. Additionally, the present disclosure describes the synthesis of O-acyl isopeptides and backbone-modified peptides (FIG. 4) which are employed to disrupt aggregation.

This is innovative because the novel amine transfer agent described herein harnesses the high nucleophilicity and acidity of thiols to enhance reactivity while avoiding epimerization. The further exploitation of an S to N acyl transfer step leads to traceless amide bond formation. By simply lowering the oxidation state of the reagent, similar reactivity gives rise to a backbone modification strategy that is useful in improving the synthesis of aggregation-prone sequences.

Furthermore, the present disclosure describes tools needed for broad application of N to C direction SPPS. The present disclosure also describes reliable methods for N-terminal peptide anchoring and cleavage to yield protected or deprotected peptides, for quantification of resin loading, for capping during SPPS, and for the synthesis of aryl diamine amino acids without the use of any coupling agents. In embodiments, the method of peptide synthesis described herein utilizes simple conjugate addition reactivity, while maintaining both the N-terminal carbamate protecting group needed to prevent racemization during the first amide bond formation and the standard cleavage conditions for generating deprotected peptides. This approach allows straightforward application of the various cleavage cocktails created to accommodate different peptide sequences over the last half-century.

The present disclosure further describes the combination of an Alloc-protected Dbz linker with the N-acyl urea elongation strategy to enable access to protected peptides. UV activity of the Nbz group is harnessed to facilitate in situ monitoring of the coupling reaction. The recently developed C-terminal modification for purification-enabling capping strategies is used, and the Dbz amino acid derivatives are synthesized without employing a coupling agent.

1. Establishing the reactivity profile of common amino acids during N to C SPPS using N-acyl urea activation.

Figure 5:
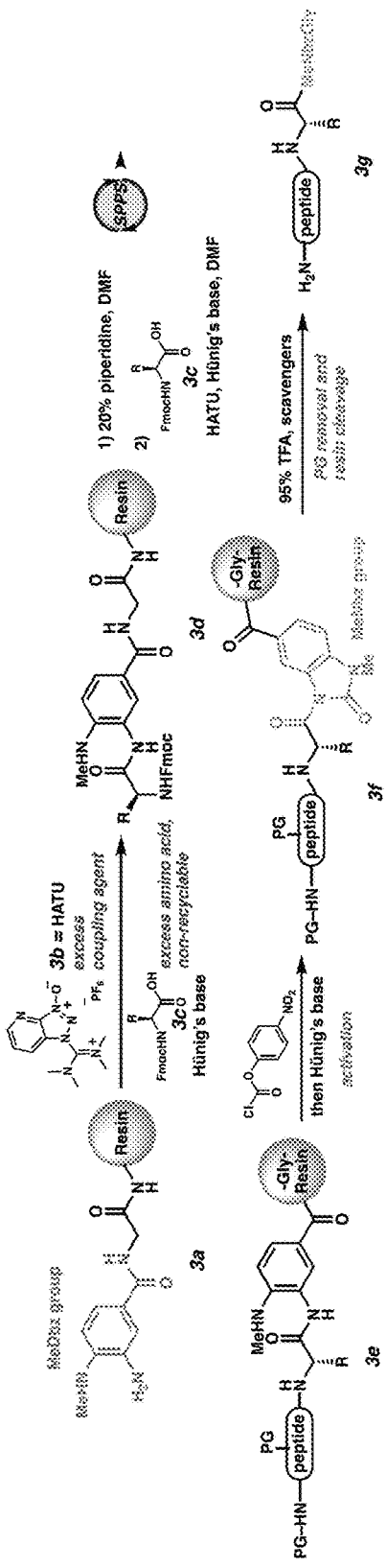
FIG. 5. Traditional Fmoc C to N SPPS illustrated with a MeDbz linker.
Figure 6:
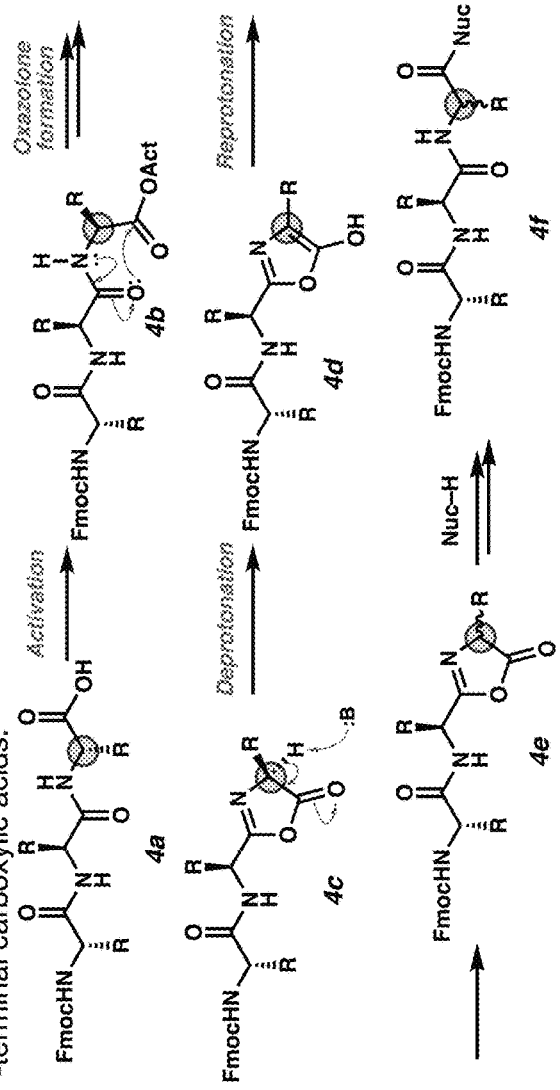
FIG. 6. Epimerization caused by oxazolone formation during activation of C-terminal carboxylic acids.

1A Introduction. Modern SPPS proceeds in the C to N direction and suffers from several problems that limit its efficiency. FIG. 5 illustrates a typical SPPS protocol employing Fmoc protection on nitrogen. During the coupling step, the incoming amino acid (3c), used in excess (typically 4-fold or more), cannot be recovered after the reaction, and must be activated toward nucleophilic attack. Significant effort by the peptide community has led to coupling agents (e.g., 3b) that avoid racemization of the individual amino acids during carboxylic acid activation, though often at the expense of coupling efficiency.[6] Double-coupling—repeating the coupling without deprotecting Fmoc—is a typical way to resolve such issues of conversion. Removal of Fmoc is typically conducted with piperidine, often leading to problematic side reactions such as β-elimination to form dehydroalanine,[7] backbone amide attack on aspartic acid residues to form aspartimides,[8] and epimerization of sensitive residues like cysteine.[9] Some of these side reactions can be avoided using Boc SPPS, but the use of gaseous HF for the final resin cleavage and side chain protecting group removal is a significant drawback of this approach. Finally, the need to access diverse functional groups on the C terminus of peptides has historically been problematic for the C to N approach. Post-SPPS modification via activation of the C-terminal peptide carboxylic acid leads to epimerization of the C-terminal residue (see FIG. 6).

Many of the limitations of C to N SPPS could readily be overcome by implementing an SPPS approach that proceeds in the N to C direction. Unfortunately, efforts to accomplish this deceptively simple goal have been fraught with challenges. For example, it is difficult to identify practical carboxylic acid protecting groups and new linker strategies that are compatible with known side chain protecting groups. More problematically, the major problems preventing adoption of reported "inverse" SPPS platforms developed to date are dehydrative reactions related to activation of the C-terminal carboxylic acid of the growing peptide chain.[3] These include diketopiperazine formation upon nucleophilic addition of the n−2 backbone nitrogen to the activated acid (4b) and C-terminal epimerization following oxazolone (4c-4e) formation (attack by the n−1 backbone carbonyl oxygen, FIG. 6). The latter represents the bigger limitation because it is not a chain-terminating event. Thus, full length peptides (4f) are produced with an unknown number of diastereomers. When the oxazolone is formed, the acidity of the hydrogen at the α-position in the amino acid is increased. Typically, coupling conditions are basic enough to cause deprotonation of this hydrogen, and, upon reprotonation, the stereointegrity of the α-center is lost. When this issue arises in N to C SPPS, heterogeneous peptides are produced of unknown stereochemical composition. Even in small quantities, these impurities are not tolerable for a pharmaceutical product.

Figure 7:
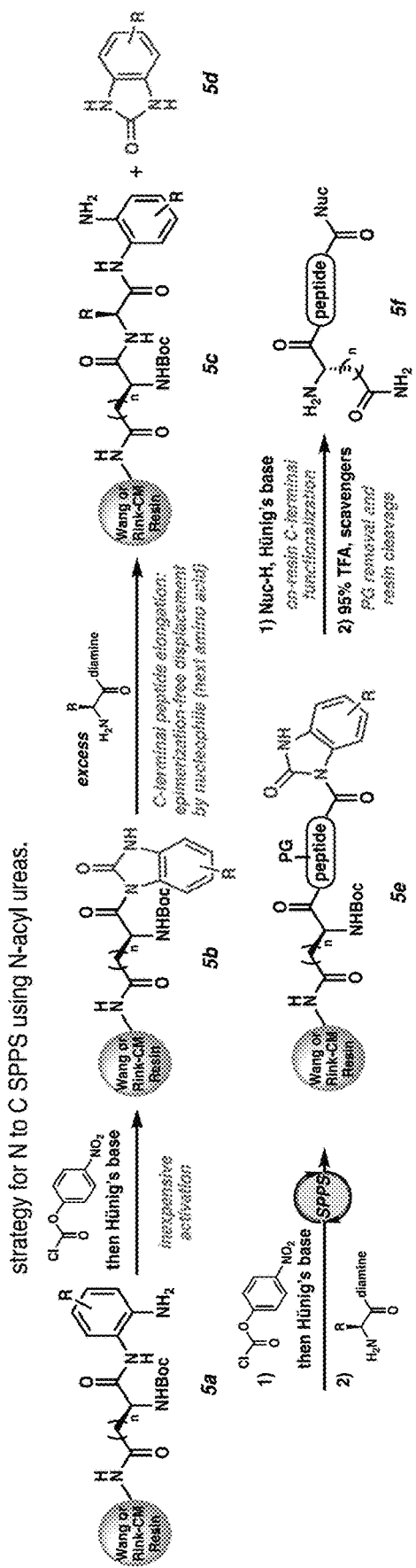
FIG. 7. Strategy for N to C SPPS using N-acyl ureas.

General N to C SPPS Design. Based on the success of the recent C-terminal peptide modification work, the present disclosure describes a novel method for N to C SPPS, which will not cause epimerization of the C-terminal amino acid or diketopiperazine formation.[9,10] In embodiments, the present disclosure describes a novel method of peptide synthesis including a side-chain anchoring strategy to attach the first amino acid to the resin (5a, FIG. 7)[11]; following attachment to the resin, activating Asn-Dbz derivative 5a using 4-nitrophenyl chloroformate or other phosgene equivalent, acylating the aniline nitrogen, followed by treating with Hünig's base to displace nitrophenol[14]; and adding the next amino acid to displace the Nbz derivative (5d). Because it is not chemically modified during the coupling reaction, the unreacted amino acid diamine will be recoverable. Repetition of the activation and displacement process leads to C-terminal peptide elongation and yields N-linked Nbz-terminated (N-acyl urea terminated) peptide 5e, which can be functionalized as desired by employing the C-terminal functionalization conditions.[4] Finally, treatment with a sequence appropriate nucleophile, such as an alcohol, amine, or thiol, functionalizes the C-terminus. Treatment with a TFA cocktail cleaves the peptide and all side-chain protecting groups to access peptides 5f.

Figure 8:
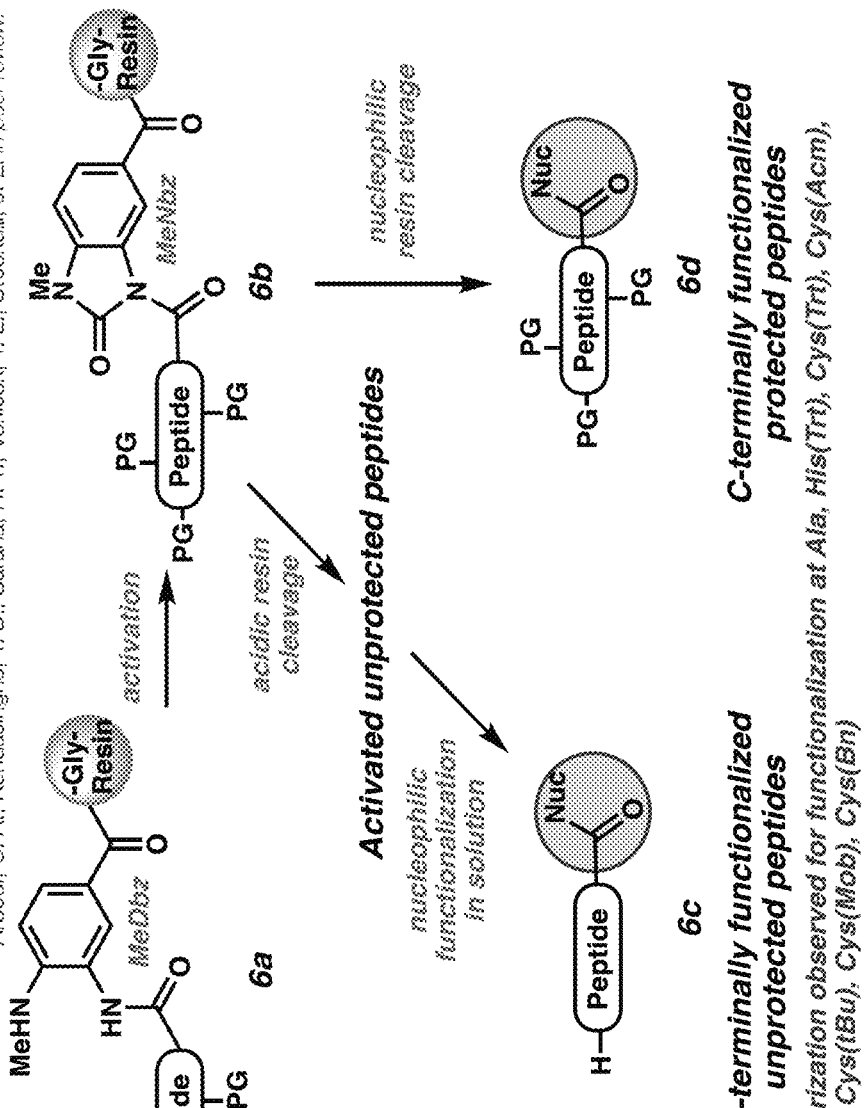
FIG. 8. N-Acyl urea strategy for C-terminal functionalization of peptides.

1B Supporting data. For both N to C SPPS and C-terminal modification of peptide carboxylic acids, the long-standing limitation has been epimerization of the C-terminal residue. An approach for C-terminal functionalization upon displacement of the activated form of the commercially available MeDbz linker was recently reported[4]a (FIG. 8). The diaminobenzoyl linker was incorporated between the solid support and the peptide (6a), which upon activation using 4-nitrophenyl chloroformate, gave the N-acyl urea (MeNbz, 6b), which was then poised to function as a leaving group. This substrate was cleaved from resin under standard TFA conditions to yield the fully deprotected peptide-MeNbz, which was used for solution-phase manipulations (6c). As an alternative approach, the peptide was directly cleaved from the resin using various nucleophiles to displace the activated linker and generate fully protected peptides (6d). This work established the scope of nucleophiles capable of displacing MeNbz ($NH_3$, $BuNH_2$, $H_2N(CH_2)_3N_3$, propargylamine, aniline, $H_2NN_2H$, MeHNOMe, MeOH, EtOH, i-PrOH, BnOH, PhOH, $H_2O$, $NaBH_4$) and confirmed that Ala- and His-terminated peptides are not epimerized during the reaction. It was demonstrated that the potential of this method for use in complex targets via C-terminal modification of the neuropressin $G^{12}$ and the active portion of glucagon-like peptide-1, GLP-1(7-36), which was selected because it is a target of broad interest to the pharmaceutical community. GLP-1 receptor agonists are state-of-the-art pharmaceutical agents for the regulation of glucose levels,[13] including 16 different GLP-1 agonists in clinical trials as of 2015.[14]

These results indicate that MeNbz is mild enough to enable functionalization of C-terminal Cys peptides. Under previous conditions, significant epimerization was observed. Unlike other amino acids, Cys commonly undergoes epimerization during attachment to the resin, during elongation of the peptide via Fmoc SPPS, as well as during activation of the C terminus.[15] The present disclosure describes the synthesis of modified C-terminal cysteine peptides without epimerization, a previously insurmountable problem. Two different strategies, both of which proceed without any detectable epimerization, were employed. The first approach exploited the exceptionally mild activating nature of the N-acyl urea group for the direct diversification of the C terminus. An alternative strategy, wherein cysteine derivatives served as nucleophiles in a resin-cleaving elongation reaction, analogously to native chemical ligation (NCL)[16] was also effective. The fundamental, novel chemical insights established in this work include the following: 1) once attached, the diaminobenzoyl linker is not sufficiently electron withdrawing to induce cysteine epimerization during elongation (as validated by extended exposure to base); 2) the N-acyl urea appears to be less electron withdrawing than any known coupling agent; and 3) when conducted on-resin, cysteine thiol attack followed by S to N acyl transfer proceeds efficiently, and the product peptides are stable to epimerization under the reaction conditions tested. No diketopiperazine products were observed for any of these reactions. The present disclosure describes the use of this approach in the synthesis of the nicotinic acetylcholine receptor antagonist α-conotoxin ImI (FIG. 9).

Figures 10A, 10B:
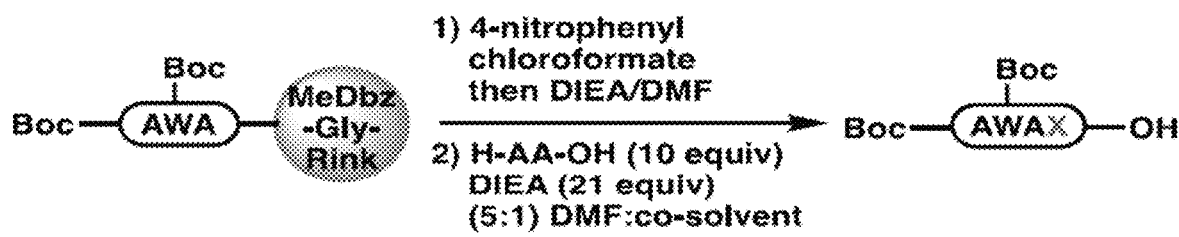
FIGS. 10A and 10B. Evaluation of conversion and epimerization for non-NCL C-terminal peptide elongation.

Since it was established that amines were good nucleophiles for MeNbz displacement, it was considered that amino acids can also be employed. Such a transformation would provide excellent support for the feasibility of N to C SPPS via an N-acyl urea activation approach. Free amino acids as nucleophiles in resin-cleaving reactions were established (FIGS. 10A and 10B).[5] Unprotected amino acids were used because of their lower cost, but their poor solubility led to significant efforts to optimize the reaction, including the addition of water as a co-solvent. The conversion and epimerization for β-branched isoleucine and secondary amine-containing proline were evaluated. They were expected to be the most challenging because of sterics and higher basicity, respectively. Employing water as a co-solvent with excess Hünig's base, reasonable conversion and no detectable epimerization for isoleucine addition over 4 h (entry 1) was observed. Counter to early results with secondary amines,[4a] it was found that proline was surprisingly reactive, with >99% conversion and 2% epimerization with water co-solvent (entry 2). A major drawback with using $H_2O$ as a co-solvent is that the undesired truncated product H-AWA-OH is also formed. To minimize this side reaction, two bulky alcohol co-solvents, i-PrOH and hexafluoroisoproanol (HFIP), were employed as solvents.[4] Isopropanol facilitated the reaction somewhat, leading to 74% conversion (entry 3), while HFIP led to >99% conversion. In either non-aqueous solvent, no epimerization was observed. Taken together, these studies support the feasibility of epimerization-free peptide elongation in the N to C direction.

1C Validation of the N to C SPPS Platform.

Figure 11:
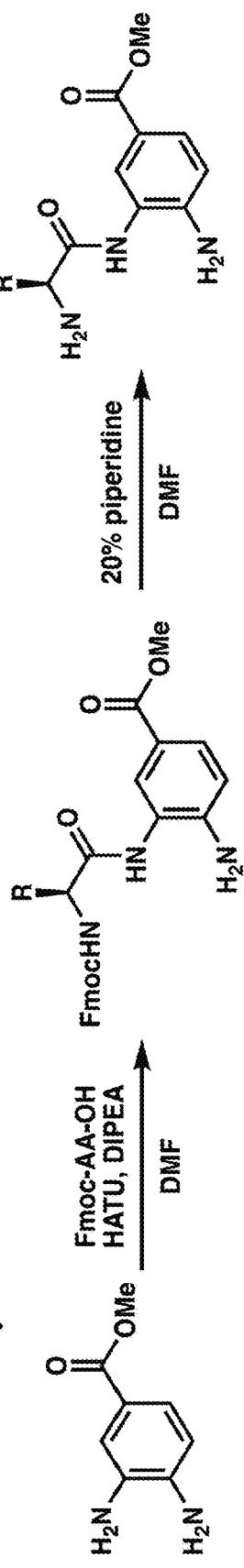
FIG. 11. Synthesis of H-AA-Dbz derivatives from Fmoc amino acids.

1C.1 Synthesis of amino acid diaminobenzoyl (H-AA-DbzOMe) derivatives. The present disclosure describes the synthesis of amino acid diaminobenzyol (H-AA-DbzOMe) derivatives. A full set of 20 amino acid diaminobenzoyl derivatives are synthesized for establishing the reactivity profile of various amino acids in the N-acyl urea activation strategy described herein. The goal is to access these without employing any coupling agents which is described below. In embodiments, the approach outlined in FIG. 11 is followed. The electronics of the aryl ring are kept as analogous as possible to the MeDbz systems already investigated, while capitalizing on reagents already available. Additionally, avoiding the need for exogenous bases in the Nbz displacement can help to avoid epimerization. Fmoc removal with piperidine unveils the target H-AA-DbzOMe groups (10c) in their neutral state (whereas Boc removal leads to the TFA or HCl salt of the amino acid, leading to the need for exogenous base in the coupling reaction). Thus, treatment of DbzOMe (10a) with Fmoc-protected amino acids under epimerization-free coupling conditions affords Fmoc-AA-DbzOMe (10b).[17]

Figure 12:
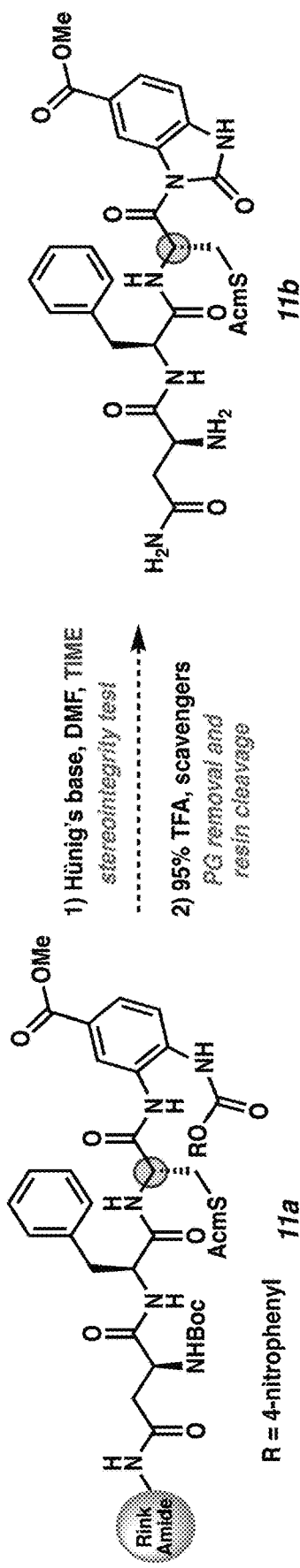
FIG. 12. Evaluation of stereointegrity at C terminus during activation of DbzOMe.

1C.2 Confirmation of stability to epimerization under Hünig's base exposure during Dbz activation conditions. To establish the N to C SPPS, the window of tolerance for the activation step must be determined. The established conditions for Dbz and MeDbz activation involve initial treatment with 4-nitrophenyl chloroformate in $CH_2Cl_2$ (40 min, provides 11a), filtration, and addition of 1M Hünig's base in DMF (~25 equiv, 15 min, FIG. 12).[4,5,14] While epimerization during our C-terminal functionalization chemistry during the activation was not observed, the NbzOMe group is slightly more electron withdrawing than the MeNbz-Gly group. Additionally, that the location of the C-terminal NbzOMe at the distal end of the peptide relative to the linker does not significantly alter its reactivity must be confirmed. The present disclosure describes the use of a C-terminal Cys for performing these studies. However, Trt cannot be used because the free thiol in the product could lead to intermolecular cleavage of Nbz group. Thus, 11a is treated with 1M Hünig's base for various lengths of time (5 min-4 h), then the peptide is cleaved with 95:2.5:2.5 TFA:TIPS:water to afford tripeptide 11b. Although the longer exposure times are not necessary for complete activation, they provide baseline information for nucleophilic addition reactions that may require an exogenous base for complete conversion.

1C.3 Determination of conversion, validation of no epimerization for the 20 native amino acids. The present disclosure describes the evaluation of the reactivity of the 20 native amino acid diaminobenzoyl derivatives (H-AA-NbzOMe) (see FIG. 13). These experiments are performed on the sequence Boc-NFC(Trt)-NbzOMe (12b). These amino acids were selected to enable attachment via side-chain anchoring, to provide a chromophore, and because Cys(Trt) is the most epimerization-prone amino acid. In synthesizing 12b, it was shown that Cys(Trt) coupling was not very efficient. Therefore, Cys is incorporated via our C-terminal elongation strategy[4b], which is followed by selective alkylation with trityl chloride and activation. Peptide 12b is then treated with varying concentrations of each amino acid for 4 h (beginning at 1.1 equiv H-AA-DbzOMe in the minimum solvent volume to allow efficient mixing/resin movement). Conversion and epimerization are determined for each reaction to establish at what point a larger excess leads to either diminishing returns in the conversion or begins to induce epimerization. With this information in hand, the role of other reaction parameters such as solvent, temperature, time, and microwave heating to maximize the coupling efficiency are determined.[18]

1D Alternative strategies. The present disclosure also describes alternative strategies for improving N to C SPPS. In embodiments, amino acid derivatives of the commercially available diamines, such as amino acid diamine-aryls illustrated in FIG. 14, can be synthesized to adjust the electrophilicity of the activated species. Because the MeNbz group is less epimerization-prone than the NbzOMe group, more electron-rich aryl diamines are evaluated. Additionally, the methyl ester of the DbzOMe group is converted to an amide and an alcohol. Variations to the aromatic ring itself can also affect the outcome. Moreover, the amine transfer strategy outlined below can be employed.

The amino acid diamine-aryls can be used in any of the methods for N to C peptide synthesis including SPPS, solution phase peptide synthesis, and fluorous phase peptide synthesis.

2. Strategies for overcoming difficult coupling reactions during N to C SPPS.

Figure 15:
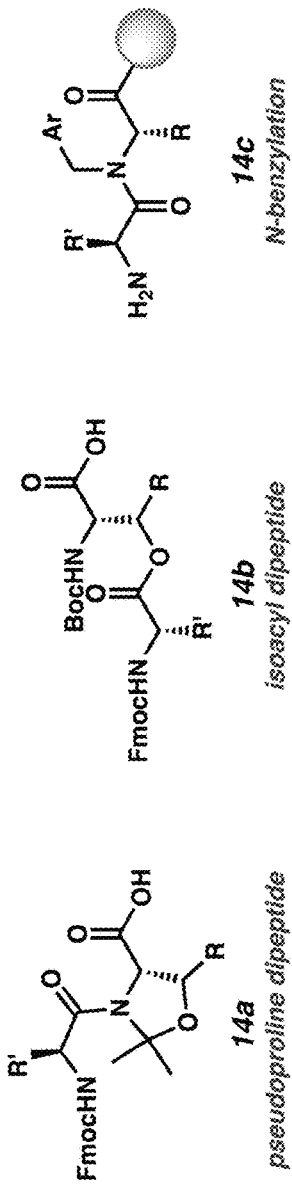
FIG. 15. Structural modifications used to limit aggregation during traditional C to N SPPS.
Figure 16:
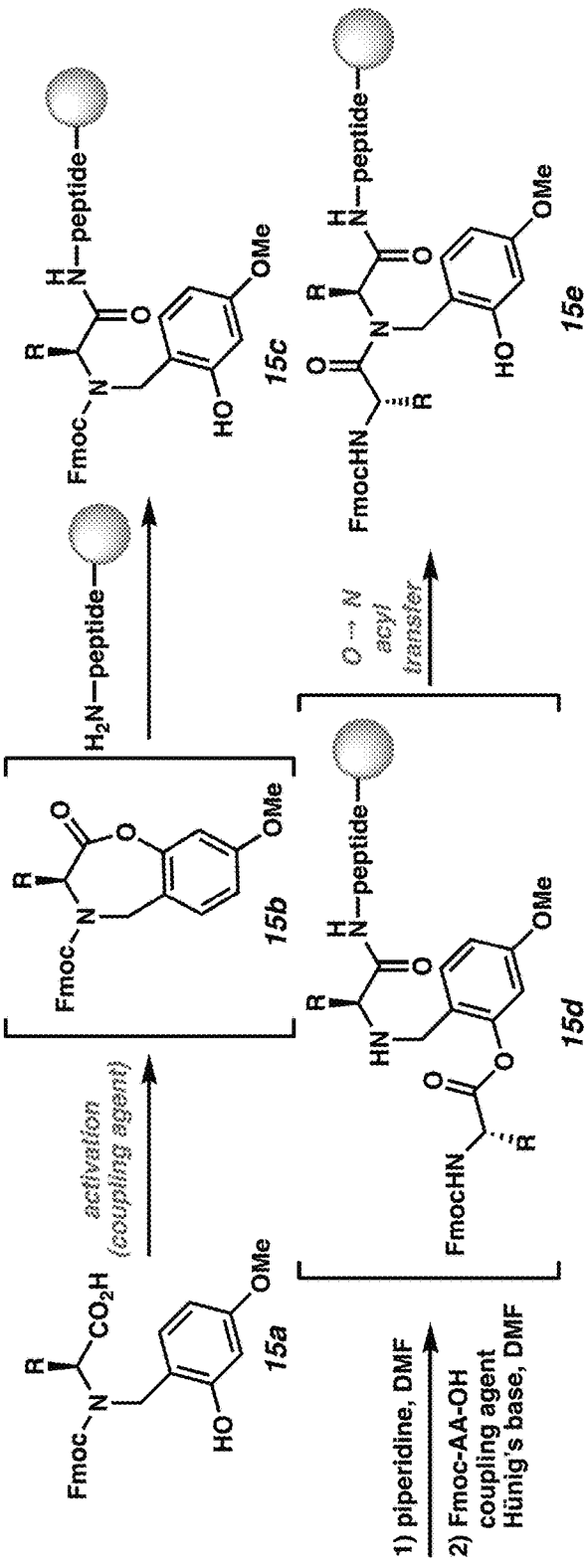
FIG. 16. Hydroxymethoxybenzyl (Hmb) group for backbone amide modification.

2A Introduction. Despite over half a century of optimization by the peptide synthesis community, there remain coupling reactions that must be repeated to achieve high levels of incorporation as well as peptide sequences that are recalcitrant to synthesis using modern C to N SPPS methods or isolation via HPLC.[19] The cause of these problems varies. Bulky amino acids (i.e., β-branched residues) or large side-chain protecting groups (i.e., Pbf) can slow down a particular coupling reaction.[20] Inter-chain interactions such as hydrogen bonding, ion pairing, and van der Waals interactions (i.e., β-sheet formation) can lead to aggregation on resin.[21] The aggregation increases the effective steric hindrance of the terminal amino acid, which can interfere with the Fmoc removal or the coupling of the next amino acid.[22] For on-resin aggregation problems encountered in traditional C to N SPPS, often referred to simply as "difficult sequences," structural modifications have been developed to disrupt inter-chain interactions by introducing a kink in the peptide chain (FIG. 15). If the target sequence includes an appropriately located serine or threonine, a pseudoproline dipeptide (14a)[23] or an O-acyl isopeptide linkage (14b)[24] is the most convenient strategy. The dipeptide building blocks for these sequences are often commercially available. In cases where the target sequence does not contain Ser or Thr, a backbone amide modification strategy is employed.[25] A reductive amination is either conducted on the N-terminal residue on the resin or on the individual amino acid, which is then Fmoc protected. Once the benzyl group is in place, the next amino acid is either double coupled or a specialized o-hydroxy or o-thiol group is used to relay the next amino acid via O to N or S to N acyl transfer (FIG. 16). In all cases, the backbone modification is designed to be cleavable during the side-chain protecting group removal (subsequent treatment with a pH 7-8 solution is required for isopeptide linkages).

2B Backbone amide modification. The present disclosure describes an amine-transfer strategy to assist in cases of difficult coupling reactions, strategies for O-acyl isopeptide and pseudoproline dipeptide synthesis, and a method for backbone N-benzylation. The amine-transfer strategy is employed to address issues described above which may arise during N to C direction SPPS because bulky amino acids and protecting groups as well as inter-strand interactions are present.

Figure 17:
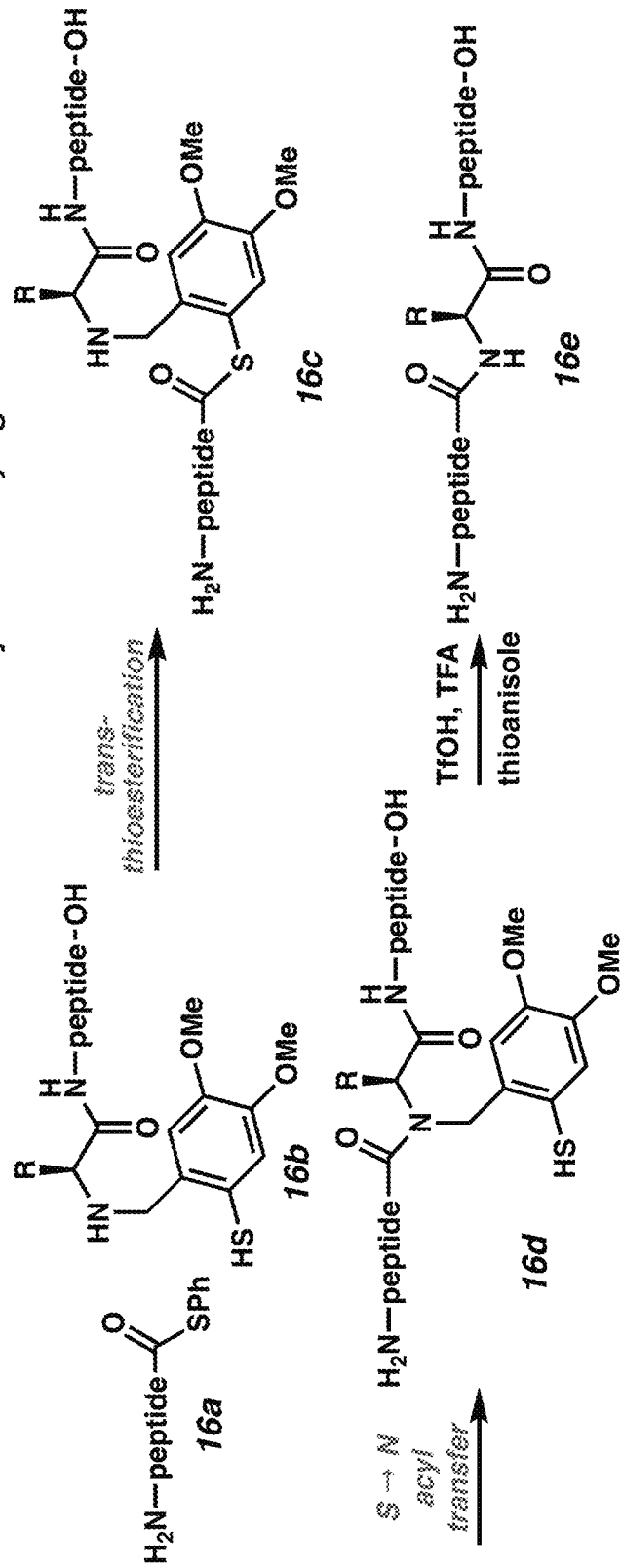
FIG. 17. Backbone amide modification for non-Cys auxiliary ligation.

The amine transfer strategy described herein can expedite slow or epimerization-prone coupling reactions. One of the backbone amide modifications employed for disrupting aggregation during C to N SPPS is the Hmb (hydroxymethoxybenzyl) group.[26] The installation of this moiety proceeds as outlined in FIG. 16. The Fmoc protected Hmb amino acid (15a) is activated upon treatment with a coupling agent to form 7-membered lactone 15b. Addition of the N-terminal amine then affords Hmb peptide 15c. Upon addition of the next activated amino acid, acylation occurs at the hydroxyl group, which is less hindered than the secondary amine, to form 15d. Acyl transfer via a 6-membered tetrahedral intermediate affords backbone modified peptide 15e. A related approach has been employed in solution as an auxiliary-based substitution for native chemical ligation.[27] In this case, an initial trans-thioesterification of peptide 16a and auxiliary-substituted 16b results in acylation of the aromatic thiol to form thioester 16c (FIG. 17). Subsequent S to N acyl transfer affords backbone modified 16d, which is treated with triflic acid and TFA in the presence of thioanisole to afford the native peptide 16e (FIG. 17).

2C Design 2C.1 Development of an amine transfer strategy for slow coupling reactions. The Dbz/N-acyl urea linker was originally developed to serve as a thioester analog in native chemical ligation reactions, and the ability to displace this moiety with aryl thiols at neutral pH without epimerization is well precedented.[14] To address slow coupling reactions, a reagent that will transiently tether the incoming amino acid nucleophile to a thiol is employed. Due to an interest in a strategy that would be traceless (i.e., not lead to backbone modification), lactol 17b was identified as an ideal amine transfer reagent (FIG. 18A). Treatment of 17a with this lactol leads to imine formation (17c), and the spontaneous cyclization of the pendant alcohol to form hemiaminal 17d. Addition of this masked imine to the growing peptide chain (17e) affords aryl thioester 17f. An S to N acyl transfer affords 17h via tetrahedral intermediate [17g]. Peptide 17h is in the same oxidation state as an N-formyl amide. These species are readily cleaved using mild nucleophiles such as NaOMe.[28] Thus, treatment with butylamine releases the native peptide 17i and generate hemi-aminal 17j, which could ultimately be recovered and recycled. Additionally, the Fmoc group is removed by butylamine treatment.[4a] Importantly, because no exogenous base is required for displacement of Nbz by a thiol, the in situ generated thioester (17f) should not be prone to epimerization.

Figure 19:
FIG. 19. Peptides known to be difficult to prepare via C to N SPPS. Peptides include 18a (SEQ ID NO: 2), 18b (SEQ ID NO: 3), 18d (SEQ ID NO: 4), and 18e (SEQ ID NO: 5).

The present disclosure describes using the amine transfer strategy outlined in FIG. 18 for any coupling reactions that cannot be sufficiently improved via optimization of the amino acid addition reaction. Additionally, several peptides have been reported as representative of "difficult" sequences (FIG. 19).[22] In embodiments, the amine transfer strategy is employed to synthesize these peptides and compare the outcomes (conversions of each coupling, number of deletion products, purity of crude peptide, overall yield) to those of the unassisted process. The selection of peptides includes those that self-assemble (18a and 18b),[29] a hydrophobic sequence prone to β-sheet formation (18c),[30] a fragment of acyl carrier protein (18d),[31] and a peptaibol sequence (18e)[32] riddled with hindered residues (U, L, V). Synthetic peptides 18a-e are analyzed by HPLC and MS and directly compared with the HPLC traces and MS data for these peptides when synthesized without employing the amine transfer agent.

Figure 20:
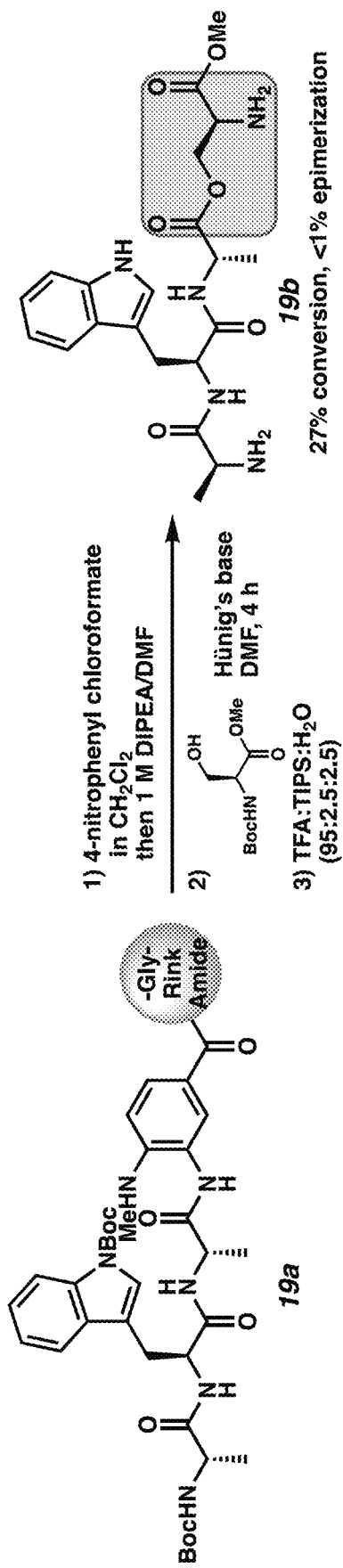
FIG. 20. Synthesis of O-acyl linkage by resin-cleaving displacement of MeNbz-Gly-Rink.

2C.2 Incorporation of O-acyl isopeptide sequences and pseudoproline dipeptides. As mentioned above, chemical modifications relying on the Ser/Thr hydroxyl group or the Cys thiol can be highly valuable in the preparation of difficult sequences. In long peptides lacking regular incorporation of proline, a natural "kink"-inducing residue, multiple pseudoprolines or isopeptides may be needed for efficient synthesis.[33] The present disclosure describes strategies for their incorporation to enable development of a general platform for N to C SPPS. To access O-acyl isopeptides, N-Boc protected serine and threonine residues are used under the conditions described above for N to C SPPS using N-acyl urea activation (under section 1). The present disclosure describes activating Boc-AWA-MeDbz-Gly-Rink (19a) (SEQ ID NO: 31) and treating it with Boc-Ser-OMe and Hünig's base (1.1 equiv each) in DMF (FIG. 20). The desired O-acyl linkage (19b) with no detectable epimerization was observed.

Figure 21A:
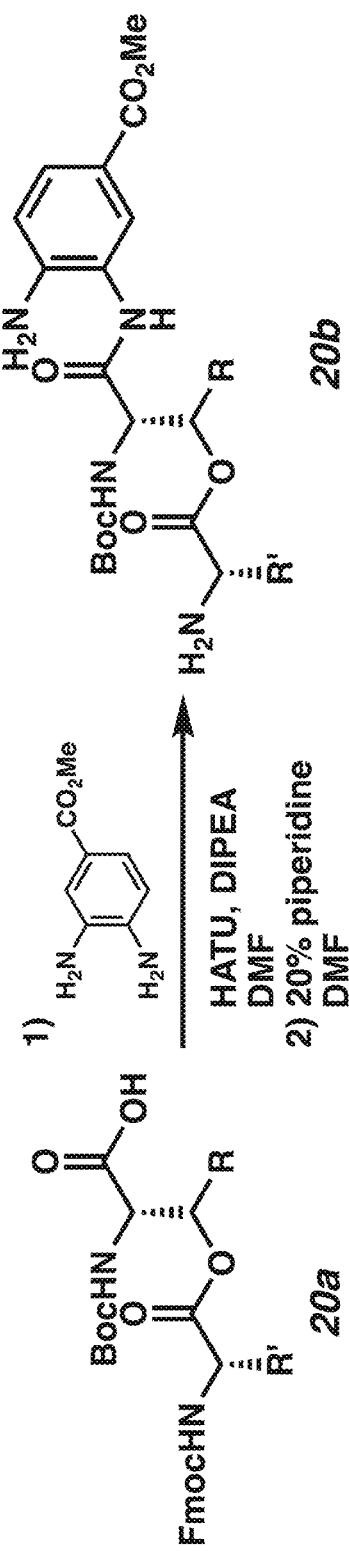
FIGS. 21A and 21B. Synthesis of O-acyl isodipeptide and pseudoproline dipeptides.
Figure 21B:
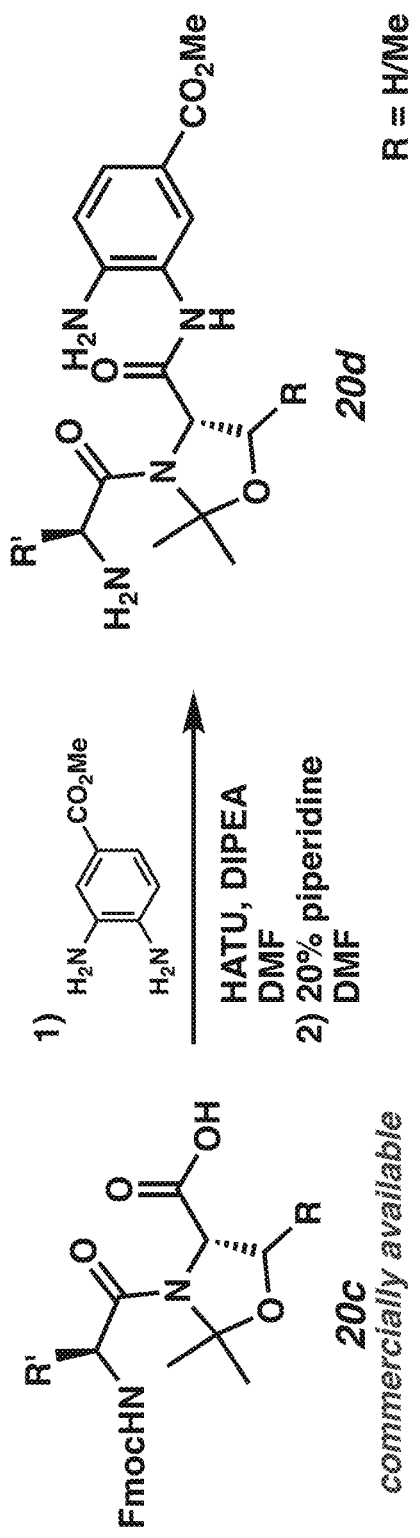

The present disclosure describes conducting investigations for improving the yield on an N-terminally linked peptide using a resin with better swelling properties. In embodiments, commercially available O-acyl isodipeptides (20a) are reacted with an aryl diamine followed by Fmoc removal to generate a dipeptide precursor (20b) for N to C SPPS (FIG. 21A). Similarly, pseudoproline dipeptide precursors (20d) from the commercially available Fmoc-protected dipeptides (20c, FIG. 21B) are accessed.

Figure 22:
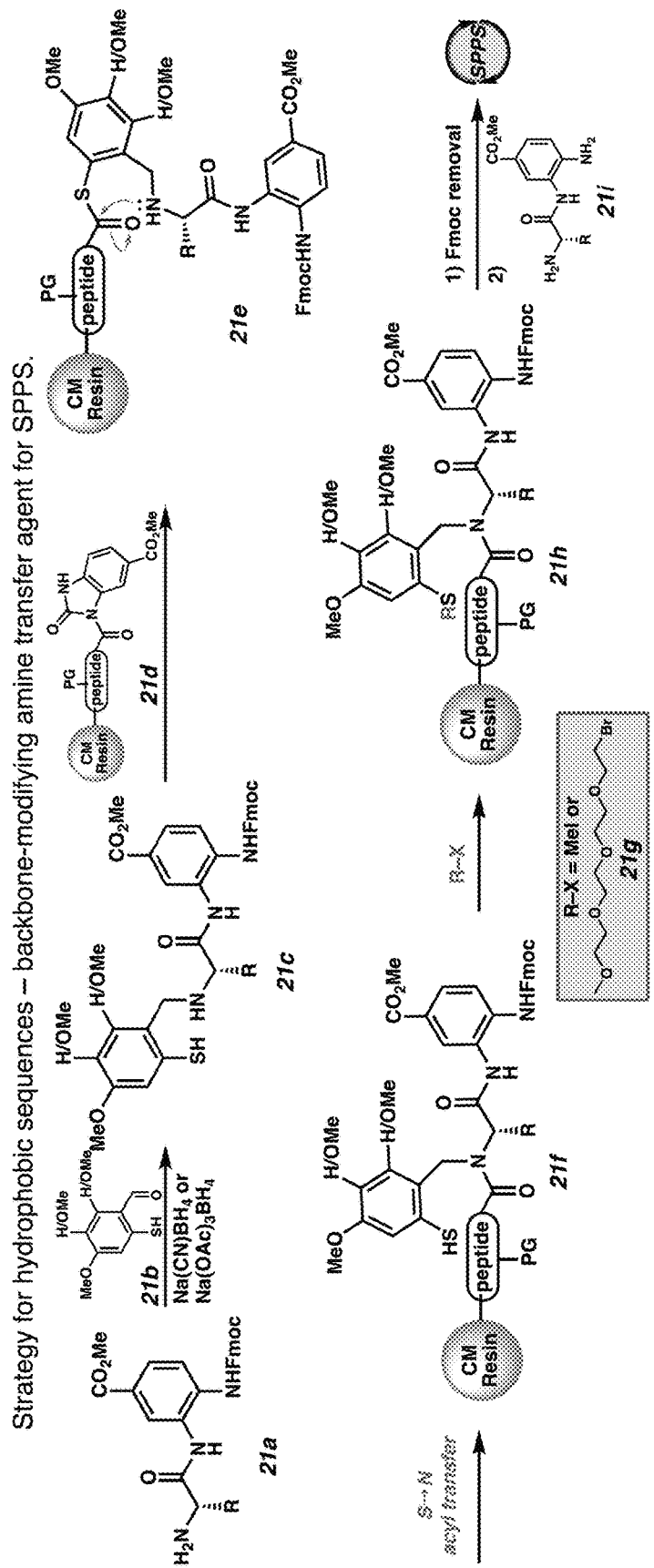
FIG. 22. Strategy for hydrophobic sequences-backbone-modifying amine transfer agent for SPPS.

2C.3 Strategy for amine transfer with amide backbone modification. For sequences that do not contain Ser or Thr, backbone modification may be necessary to disrupt aggregation during the SPPS. The present disclosure describes installing electron-rich benzyl derivatives on the backbone by employing a strategy analogous to those described in sections 2C.1 and 2B. Thus, amino acids 21a are reacted with benzaldehydes 21b via a reductive amination process to afford benzylated amino acids 21c (see FIG. 22). Addition of these derivatives to the growing peptide chain results in NbzOMe displacement (21d→21e) followed by S to N acyl transfer to generate 21f. An alkylation with MeI would prevent interference of the thiol in further chemistry, should this issue arise, or other solubilizing tags such as PEG4-bromide (21g) could be added if the aryl group is to be left in place during further handling operations. Following Fmoc removal, 21h is subjected to addition of the next amino acid (21i). Conversion is determined, and validation that no epimerization or diketopiperazine products are formed during the 21i addition is confirmed. The inclusion of the backbone benzyl group could increase the tendency to form oxazolone. If so, the next amino acid is added using one of the strategies described in sections 1D or 2C.1. The aldehydes 21b, which contain 1, 2, or 3 methoxy groups, depending on how permanent this modification is intended to be, are accessed according to known procedures.[34]

2D Alternative strategies. The present disclosure describes alternative strategies which combine the amine transfer strategy (section 2C.1) with plans to tune the Dbz reactivity through adjustments to the substituents on the aromatic ring or the aromatic ring structure itself (section 1D) if any reactivity or epimerization issues remain after implementing these strategies independently.

3. Development of Tools for Application of N to C SPPS.

3A Introduction. The present disclosure describes the development of a suite of tools for the N to C SPPS platform that are useful, simple, and straightforward as C to N SPPS, which has benefited from over 50 years of optimization. In addition to the basic tools described in section 1 for iterative SPPS via Dbz activation and displacement and the most critical modifications outlined in section 2 for the synthesis of difficult sequences, the present disclosure describes the development of a set of tools analogous to those available for SPPS in the C to N direction. These include resin attachment and removal strategies that can generate deprotected or protected peptides, irrespective of the identity of the N-terminal amino acid (section 3B.1), capping strategies to facilitate purification (section 3B.2), and a coupling agent-free synthesis of aryldiamine-modified amino acid precursors (section 3B.3).

Figure 23:
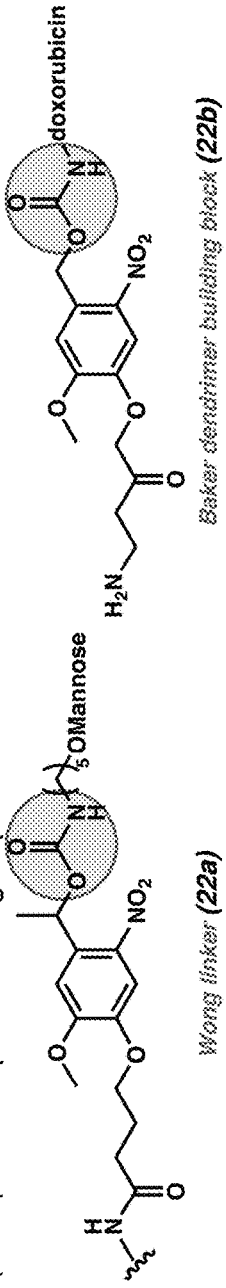
FIG. 23. 2-(2-Nitrophenyl)propyloxycarbonyl- and 6-nitroveratryloxycarbonyl (Nvoc)-derived photolabile groups.

3B Design 3B.1 N-terminal anchoring strategies for the synthesis of deprotected or protected peptides via N to C SPPS. Information is available to identify the best possible linker strategy for C to N SPPS.[35] Fewer reports have been dedicated to strategies for N-terminal anchoring. Of these, some are focused on anchoring a full peptide sequence after deprotection and purification to facilitate on-resin ligation chemistry,[36] while others involve a relay mechanism (so-called "safety-catch") to convert a C-terminally linked peptide directly to an N-terminally linked peptide.[37] However, none of these represent ideal methods for N-terminal anchoring to conduct N to C SPPS. The present disclosure describes a photolabile linker for N to C SPPS. This type of linker enables access to both protected and unprotected peptides. Several photolabile linkers have been developed for C to N SPPS and for other solid-phase chemistry.[38] In embodiments, a linker with an NVOC-like[39] structure, such as those developed for glycan arrays (22a)[40] and doxorubicin dendrimers (22b, FIG. 23),[41] would be ideal for N-terminal amino acid linkages because they contain a carbamate on cleavable portion (see blue circles). A carbamate would be needed to prevent racemization of the first amino acid in the N to C SPPS because activation of a single amino acid in solution requires this type of protecting group.[6,8]

Figure 24A:
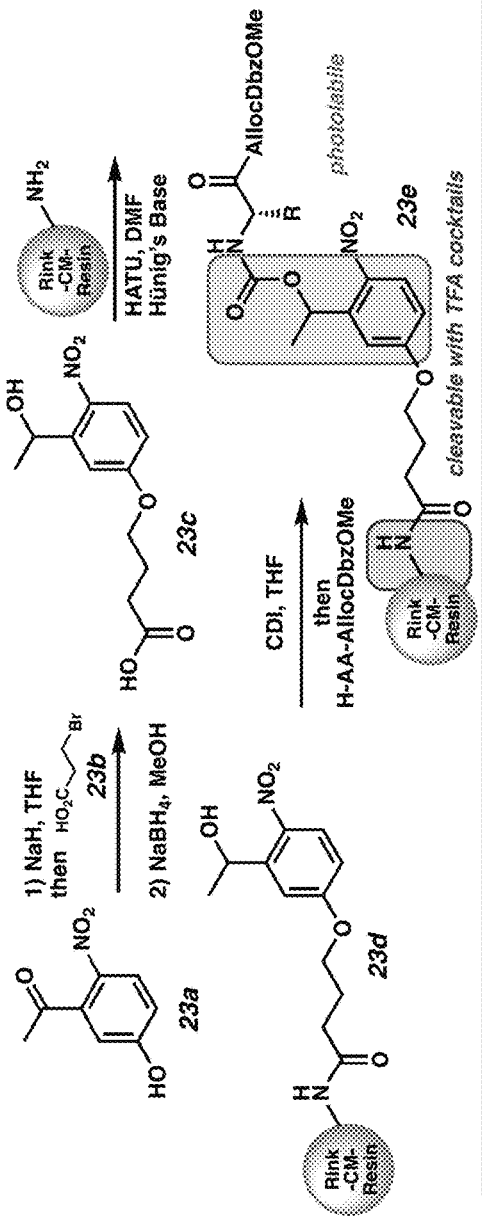
FIGS. 24A and 24B. Access to protected or deprotected peptides via photolabile linker.
Figure 24B:
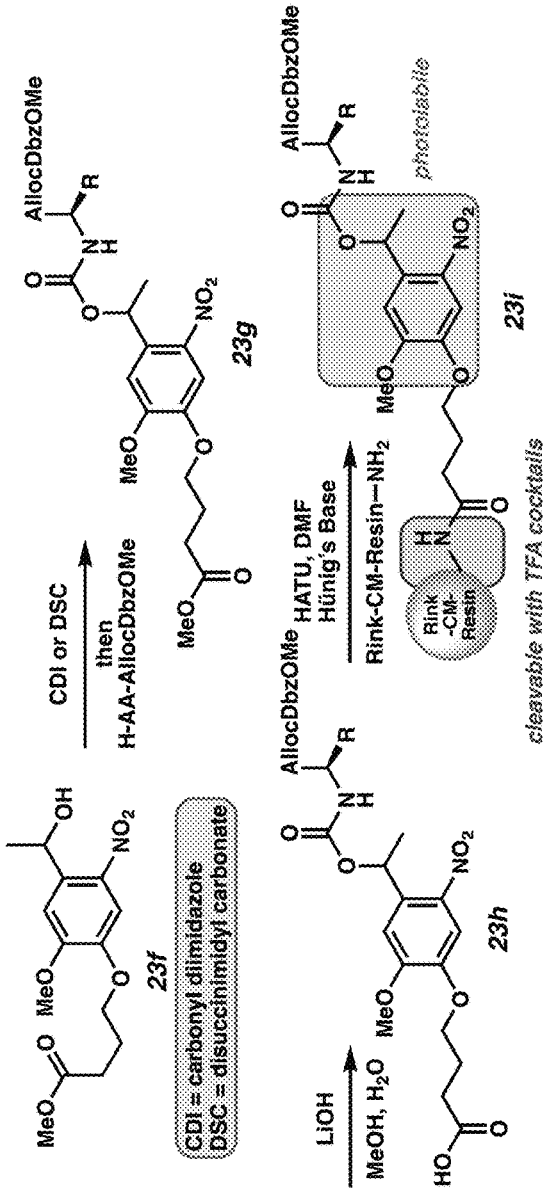

The present disclosure describes the synthesis of photolabile linkers (as outlined in FIG. 24A). In embodiments, the synthesis of photolabile linker 23e starts from commercially available o-nitro ketone 23a. Alkylation of the phenol is followed by selective borohydride reduction of the aryl ketone in the presence of the nitro group.[40] Alternatively, Meerwein-Pondorf-Verley reduction generates 23c.[42] Attachment of the resultant pendant carboxylic acid to a Rink amide-functionalized ChemMatrix resin affords 23d. Reaction with CDI followed by addition of the amino acid building block provides loaded resin 23e. Other embodiments incorporate a more electron-rich aromatic ring (FIG. 24B). Benzylic alcohol 23f is an intermediate in the reported synthesis of 23a.[50] Treatment with CDI or DSC followed by amino acid addition affords carbamate 23g. Selective hydrolysis of the methyl ester generates 23h. Finally, coupling to the Rink amide linker affords 23i. These linker strategies share 2 important design elements, including a photochemical cleavage option for access to protected peptides and a TFA cocktail cleavage option. The latter provides a method to more easily monitor the early coupling steps when low molecular weight products are being formed.

3B.2) Polarity-differentiated capping strategies to facilitate removal of truncated impurities. A commonly employed strategy to prevent contamination of long peptides with impurities containing deletion products is to employ a capping step after problematic coupling reactions. For traditional C to N SPPS, treatment with acetic anhydride will acylate any unreacted amines, aiding in their separation.[43] A significant advantage of the N-acyl urea activation strategy is that a variety of nucleophiles may be used to displace it, as established by published work.[4a] The present disclosure describes improved purification results due to judicious selection of the capping strategy. The polarity of a peptide is significantly altered by the C-terminal functional group.[4b,44] For peptides terminated in a carboxylic acid, the removal of deletion products is significantly improved if their C-terminus is an ester or alkyl amide. Conversely, peptide C-terminal esters and carboxamides are more straightforward to purify if the deletion products are carboxylic acids.

Figure 25:
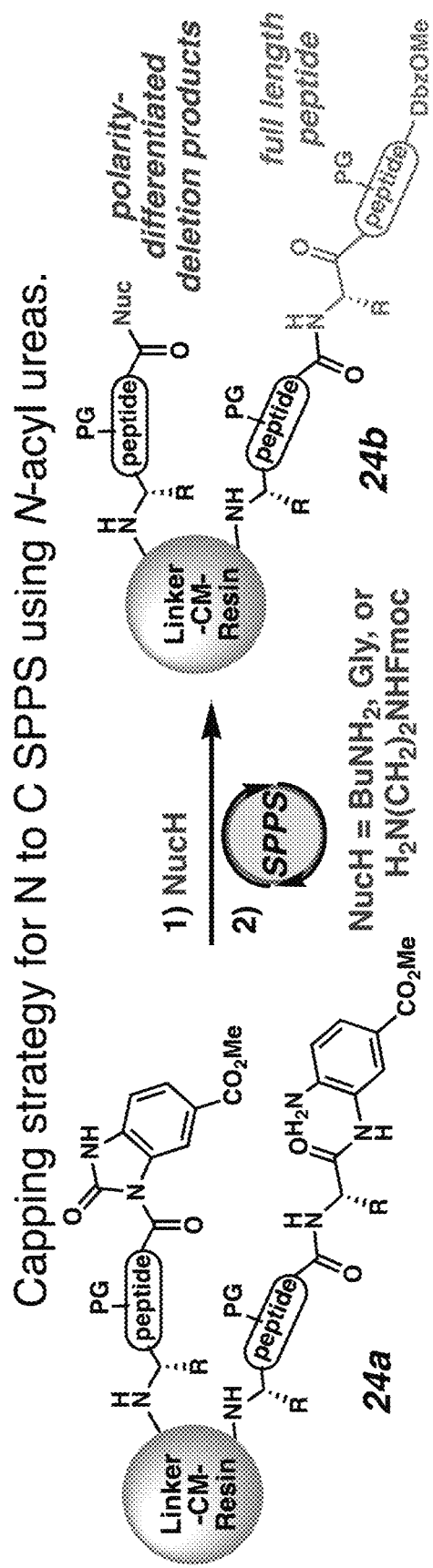
FIG. 25. Capping strategy for N to C SPPS using N-acyl ureas.

In FIG. 25, the on-resin product of a coupling reaction that does not proceed to full conversion (24a) is shown. The remaining N-acyl urea moiety could react with the next amino acid, leading to deletion products. Thus, it is treated with a more reactive nucleophile to truncate the peptide at this deletion. Because primary amines react most efficiently with the N-acyl urea,[4a] amines bearing the desired polarity group as substituents for the capping are used. Capping reactions for C-terminal acids employ butylamine as the nucleophile. Those for C-terminal esters and amides employ either glycine or its t-butyl ester, which are cleaved upon side-chain protecting group removal. In all cases, the minimum time and concentration of nucleophile needed for efficient coupling are determined. Fmoc-appended diaminoethane is employed to provide a secondary method to determine the conversion of coupling steps (sections 1-2). Implementation of the standard protocol for determining loading in Fmoc-SPPS[45] results in Fmoc removal, allowing quantification of the deletion products. Additionally, a standard protocol for the UV determination of N-acyl urea concentration in solution is developed, which provides a complimentary method for quantifying conversion and resin loading.

The efficiency of each capping step is determined by integration of the HPLC ratios of the elongated-DbzOMe peptide, the truncated-capped peptide, and the truncated-NbzOMe peptide. The rinsing protocol developed does not interfere with the next coupling reaction.

The present disclosure describes alternative strategies such as those discussed above. Moreover, if a more photolabile photolinker is ultimately desired, the present disclosure describes modifying the linker strategy to include thiophenyl or benzoyl substituents.[46]

The N to C direction peptide synthesis described herein can be performed by solid-phase peptide synthesis, solution phase peptide synthesis, and fluorous phase peptide synthesis.

The present disclosure describes an efficient novel platform for peptide synthesis that allows recovery of unreacted amino acid building blocks, avoids repetitive deprotection steps, and obviates the need for coupling agents. In addition to the basic methods for peptide assembly, traceless and backbone-modifying approaches are developed that facilitate amine transfer by exploiting a facile trans-thioesterification reaction to enable the formation of amide linkages between hindered residues. In embodiments, the present disclosure describes new methods for O-acyl isopeptide construction and dipeptide incorporation as well as a bifunctional N-terminal anchoring strategy that harnesses both the photolabile nature and carbamate structural element of the Nvoc and Nppoc protecting groups. Moreover, novel methods for polarity-differentiated capping are described herein which improves peptide purification.

The novel methods described herein vertically advance the field of peptide synthesis by providing fundamental insights into chemical reactivity and improving access to bioactive peptide targets in high purity and with minimal non-recoverable waste. Additionally, by preventing certain problematic side reactions and avoiding the need for Fmoc removal steps, strategic flexibility is increased, facilitating the parallel development of novel methods for ongoing synthetic challenges in the field. The methods described herein can positively impact society by improving the accessibility of peptide pharmaceuticals, as well as lowering the cost and environmental impact associated with their synthesis and purification.

The term "derivative" as used herein refers to a compound that is obtained from a similar compound or a precursor compound by a chemical reaction. Examples include an amino acid derivative.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in the ability to perform epimerization free N to C solid phase peptide synthesis.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the subject matter (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the subject matter and does not pose a limitation on the scope of the subject matter otherwise claimed. No language in the specification should be construed as indicating any non-claimed element essential to the practice of the present disclosure.

Groupings of alternative elements or embodiments of the subject matter disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of the subject matter are described herein, including the best mode known to the inventors for carrying out the described subject matter. Of course, variations on these described embodiments will become apparent to those of ordinary skill in the art upon reading the foregoing description. The inventor expects skilled artisans to employ such variations as appropriate, and the inventors intend for the subject matter to be practiced otherwise than specifically described herein. Accordingly, the subject matter disclosed herein includes all modifications and equivalents of the subject matter recited in the claims appended hereto as permitted by applicable law. Moreover, any combination of the above-described elements in all possible variations thereof is encompassed by the subject matter unless otherwise indicated herein or otherwise clearly contradicted by context.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

EXEMPLARY EMBODIMENTS

The following are exemplary embodiments:

1. A method of synthesizing a peptide, wherein the method includes preparing a first amino acid for synthesis, coupling an amino group of a second amino acid to the carboxyl group of the first amino acid to obtain a peptide, and optionally elongating the peptide by coupling one or more amino acids sequentially to a C-terminus of the peptide, wherein the amino acids used in the method are derivatized amino acids, and wherein the method proceeds without detectable epimerization of an amino acid at the carboxyl terminus of the peptide.

2. The method of embodiment 1, wherein the method includes solid-phase peptide synthesis, solution phase peptide synthesis, or fluorous phase peptide synthesis.

3. The method of embodiment 1 or 2, wherein the method further includes derivatizing amino acids to be used in synthesizing the peptide prior to preparing a first amino acid.

4. The method of any one of embodiments 1-3, wherein derivatizing amino acids comprises synthesizing amino acid diaminobenzoyl derivatives or amino acid diamino-aryl derivatives.

5. The method of any one of embodiments 1-4, wherein synthesis of amino acid diaminobenzoyl derivatives comprises obtaining Fmoc protected amino acid (Fmoc-AA-OH), reacting diaminobenzoylOMe (DbzOMe) with Fmoc-AA-OH to obtain Fmoc-AA-DbzOMe, and removal of Fmoc to yield H-AA-DbzOMe derivative.

6. The method of any one of embodiments 1-4, wherein synthesis of amino acid diamino-aryl or heteroaryl derivatives comprises obtaining Fmoc protected amino acid (Fmoc-AA-OH), reacting diamino-aryl or diamino-heteroaryl molecule with Fmoc-AA-OH to obtain Fmoc-AA-diamino-aryl or Fmoc-AA-diamino-heteroaryl molecule, and reacting with piperidine to remove Fmoc to yield H-AA-diamino aryl or H-AA-diamino-heteroaryl derivative.

7. The method of any one of embodiments 1-6, wherein preparing the first amino acid comprises attaching the first amino acid to a resin prior to coupling the amino group of second amino acid to the carboxyl group of the first amino acid.

8. The method of any one of embodiments 1-7, wherein attaching the first amino acid to the resin comprises anchoring the α-amino group or a side-chain of the first amino acid to the resin.

9. The method of any one of embodiments 1-8, wherein the method further comprises activating the first amino acid to form a first amino acid comprising an N-acyl urea group.

10. The method of any one of embodiments 1-9, wherein the activating the first amino acid comprises treating with 4-nitrophenyl chloroformate or other phosgene equivalent and followed by treating with Hünig's base.

11. The method of any one of embodiments 1-10, wherein coupling comprises adding a derivatized amino acid to displace the N-acyl urea group on the C-terminal amino acid of a peptide or single amino acid to yield an elongated peptide.

12. The method of any one of embodiments 1-11, wherein the method further comprises elongation of the peptide comprising repetition of activation of the peptide and coupling of the peptide with another derivatized amino acid to obtain a N-acyl urea group terminated peptide.

13. The method of any one of embodiments 1-12, wherein the method further comprises after elongating the peptide to a desired length, cleaving the N-acyl urea group from the C-terminus of the peptide to obtain a C-terminally functionalized unprotected peptide or a C-terminally functionalized protected peptide.

14. The method of any one of embodiments 1-13, wherein cleaving the peptide comprises acidic resin cleavage to obtain a C-terminally functionalized unprotected peptide.

15. The method of any one of embodiments 1-13, wherein cleaving the peptide comprises resin cleavage to obtain a C-terminally functionalized protected peptide.

16. The method of any one of embodiments 1-13, or 15, wherein nucleophilic resin cleavage comprises treatment with one or the following nucleophiles or a related molecule: $NH_3$, $BuNH_2$, $H_2N(CH_2)_3N_3$, propargylamine, aniline, $H_2NN_2H$, MeHNOMe, MeOH, EtOH, i-PrOH, BnOH, PhOH, $H_2O$, or $NaBH_4$.

17. The method of any one of embodiments 1-16, wherein the method further comprises elongation of the peptide in the C to N direction.

18. The method of any one of embodiments 1-17, wherein elongation to the desired length is completed in the N to C direction.

19. The method of any one of embodiments 1-18, wherein unreacted C-terminally derivatized amino acid diamines (H-AA-diamine) are recovered and reused.

20. The method of any one of embodiments 1-19, wherein the coupling reaction employs an amine transfer agent to avoid epimerization, to improve synthesis of aggregation-prone sequences, and/or avoid backbone modification.

21. The method of embodiment 20, wherein lactol is employed as an amine transfer agent and reacted with compound 17a to obtain compound 17d, wherein R is any amino acid side-chain, whether canonical or non-canonical.

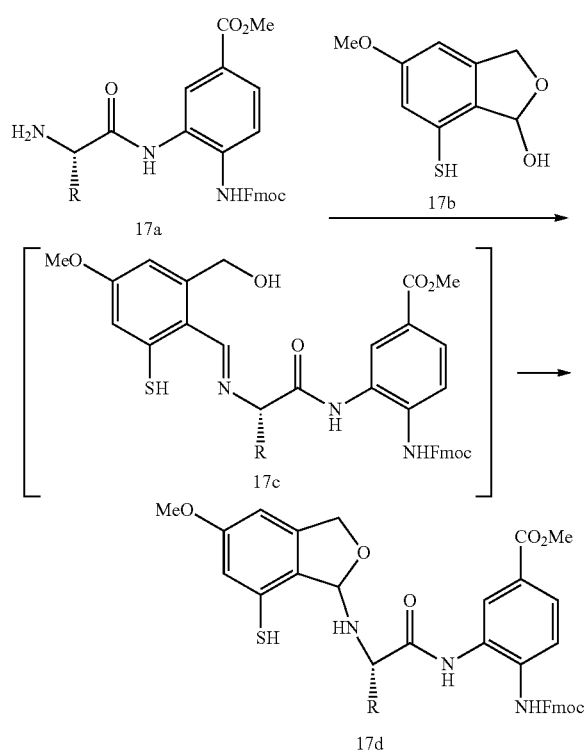

22. The method of embodiment 20 or 21, wherein Compound 17(d) is added during the elongation reaction to enable S to N acyl transfer to obtain Compound 17(h).

Compound 17(h)

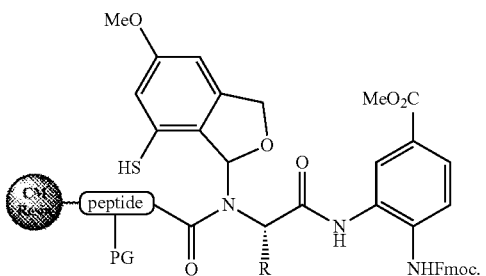

23. The method of embodiment 22, wherein the Compound 17(h) is cleaved with any nucleophile.

24. The method of any one of embodiments 21-23, wherein the amine transfer agent is used to synthesize difficult to sequences such as sequences that tend to self-assemble, hydrophobic sequences prone to β-sheet formation, a fragment of acyl carrier protein, or a peptaibol sequence including α-aminoisobutyric acid and/or β-pheylalaninol.

25. The method of any one of embodiments 1-24, wherein the method further includes incorporating O-acyl isopeptide sequences and pseudoproline dipeptides.

26. The method of embodiment 25, wherein the method includes using N-Boc protected serine and threonine residues using N-acyl urea activation for incorporating O-acyl isopeptides.

27. The method of any one of embodiments 1-26, wherein the method further includes incorporating electron-rich benzyl derivatives on the backbone to disrupt aggregation.

28. The method of embodiment 27, wherein the electron-rich benzyl derivatives are benzylated amino acids obtained by reacting amino acids with benzaldehydes via a reductive amination process (FIG. 21).

29. The method of embodiment 27, wherein the benzylated amino acids are added to the elongating peptide chain.

30. The method of any one of embodiments 1-29, wherein the method further includes incorporating a photolabile linker at the N-terminus of the peptide for N-terminal anchoring.

31. The method of embodiment 30, wherein the photolabile linker has a NVOC-like structure.

32. The method of any one of embodiments 27-29, wherein the method further includes coupling a Rink amide linker at the N-terminus of the peptide for N-terminal anchoring.

33. The method of any one of embodiments 1-34, wherein the method further includes capping the C-terminal functional group to prevent contamination of long peptides with impurities.

34. The method of embodiment 36, wherein capping comprises treating the elongating peptide with a nucleophile such as, but not limited to: butylamine, glycine, or $H_2H(CH_2)_2NHFmoc$.

EXAMPLES

Figure 26:
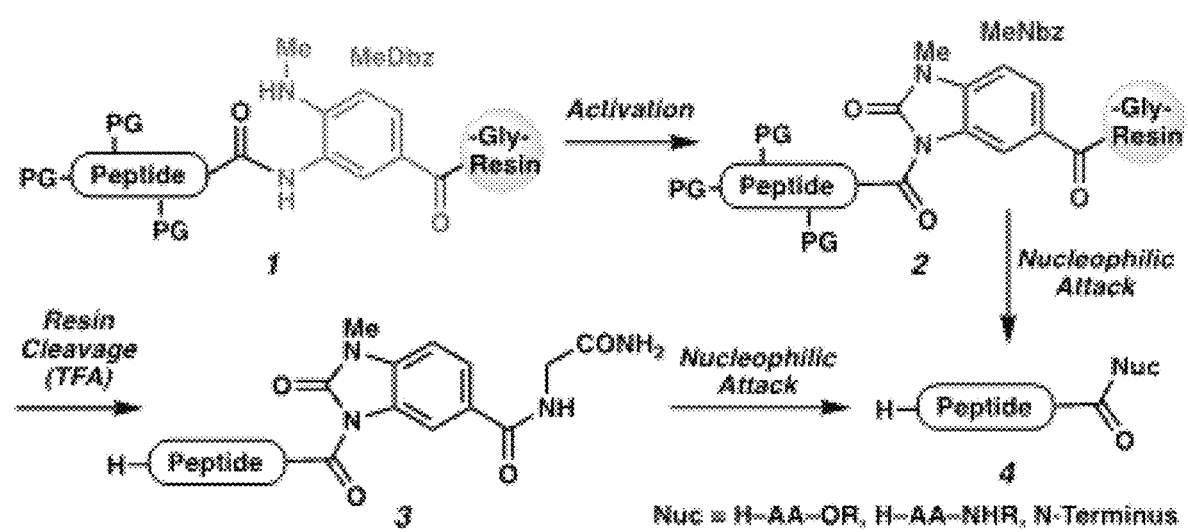
FIG. 26. Previous C-terminal functionalization of peptides.
Figures 31A, 31B:
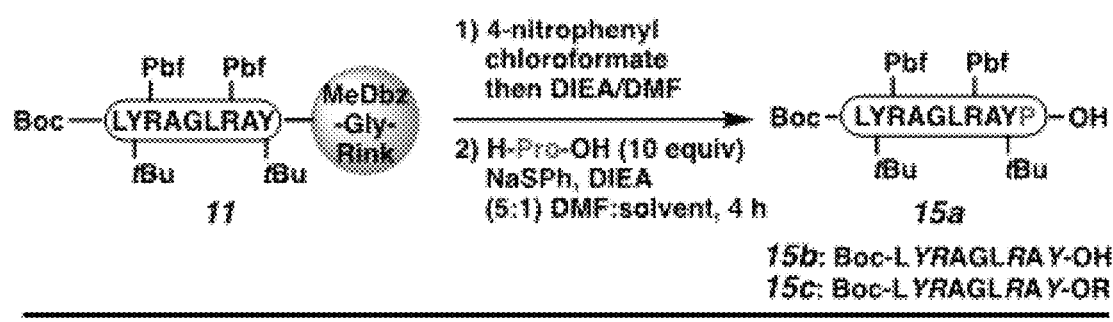
FIGS. 31A and 31B. Proline elongation solvent screen.
Figure 32:
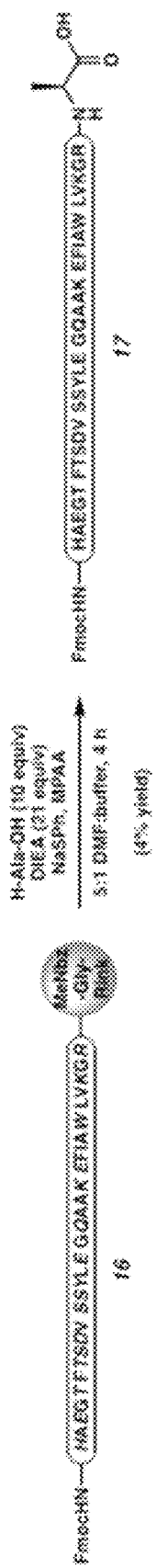
FIG. 32. Peptide cleavage and elongation of GLP-1(7-36).

Example 1. Sequence Diversification by Divergent C-Terminal Elongation of Peptides. Methods for the rapid diversification of peptide sequences are important in the optimization of peptide lead targets. Because of the tendency to epimerize the C-terminal residue during the carboxylic acid activation, sequences that vary at the C-terminal amino acid have not been readily accessible without repetition of the SPPS for each desired C-terminal amino acid. Recently, a method for C-terminal derivatization, as outlined in FIG. 26 was reported. First, peptide 1 is generated on solid support with a MeDbz linker. After activation to form the N-acyl urea (MeNbz, 2), the peptide was either displaced with a nucleophile to generate protected peptide 4, or it was cleaved from the resin, and then the unprotected peptide (3) was functionalized. During this work, it was found that the C-terminal residue is not epimerized during the modification reaction, even for sensitive residues such as His or Cys. Therefore, this approach is ideal for sequence diversification at the C-terminus.

Efficient addition of primary amine nucleophiles to MeNbz-appended peptides to generate secondary C-terminal amides has been reported. Reduced reactivity for secondary amines and α-branched alcohols during resin-cleaving reactions was observed. However, solution-phase functionalization proceeded more quickly. Therefore, investigations toward C-terminal peptide elongation using α-branched primary amines (i.e., amino acids) as nucleophiles in solution began. As shown in FIGS. 27A and 27B, a variety of amino acids can be employed as nucleophiles in the elongation of MeNbz-appended peptides in solution. For initial evaluations, AWA peptide 5 was employed, and upon treatment with 10 equiv amino acid and 11 equiv Hünig's base, complete conversion was observed in all cases to form either the corresponding elongated peptide (6a) or a mixture of 6a and hydrolysis product 6b. Water was employed as a co-solvent to improve the solubility of the unprotected amino acid nucleophiles relative to acetonitrile alone. In the absence of added water, reactivity was poor. The non-branched nucleophile glycine led exclusively to the elongated peptide H-AWAG-OH (SEQ ID NO: 32) (entry 1). However, when alanine was employed as a nucleophile, 1:1 elongation to hydrolysis was observed (entry 2). In previous work, it was found that the secondary amine Weinreb amine reacted much more slowly than primary amine nucleophiles. Therefore, it was not surprising to find that when proline was the nucleophile, only 29% elongated peptide was observed. Surprisingly, the α- and β-branched isoleucine reacted analogously to glycine, giving only the C-terminal elongation product H-AWAI-OH (SEQ ID NO: 33) (entry 4). Unprotected tryptophan required only 30 min and led exclusively to elongated peptide H-AWAW-OH (SEQ ID NO: 34), presumably because the unprotected nitrogen in the indole increases the amino acid's solubility (entry 5). Additionally, it is conceivable that a transient 7-7 interaction with the MeNbz group assists in the addition. The test peptide H-AKTWA-MeNbz-Gly-NH$_2$ (SEQ ID NO: 35) (7) was also employed to determine whether the elongation was efficient enough to modify unprotected peptides bearing nucleophilic side chains. Unfortunately, only glycine reacted quickly enough to outcompete macrolactam formation, affording 8a as the major product (entry 6). All α-branched amino acids led primarily to macrocycle 8c (entries 7-9).

Figure 33:
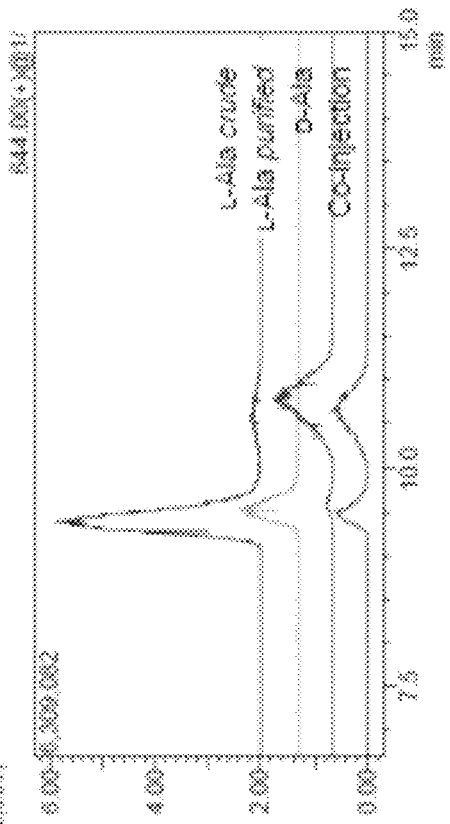
FIG. 33. Evaluation of C-terminal alanine epimerization with proline. D-Ala, L-Ala, and co-injection, gradient at 50% MeCN/H$_2$O (0.1% HCOOH) over 15 min FIG. 34. Strategy for C-terminal peptide modification.

Based on these results, it was clear that a useful strategy for C-terminal elongation would need to proceed directly from the resin-bound MeNbz peptide, where nucleophilic side chain groups would be protected. Thus, MeDbz-linked peptide 9 was activated and treated with 10 equiv glycine, 11 equiv DIEA in 500 μL DMF affording exclusively desired peptide 10a (FIGS. 28A and 28B. However, the conversion in this case was very low (5%, entry 1). To improve the reactivity of the amino acids, water was again employed as a co-solvent to help solubilize the free acid (entry 2). This modification improved the conversion to 39%, which was promising, but certainly not synthetically viable. The amount of Hünig's base employed was next increased, leading to 76% conversion over 4 h and a 91:9 ratio of elongation (10a) to hydrolysis (10b, entry 3). Sodium thiophenolate was added to generate a thioester in-situ, but it did not significantly alter the reaction outcome (entry 3). The combination of NaSPh and ethyl-3-mercaptopropionate led to complete consumption of 9, however the alkyl thioester was the sole observed product (entry 4). Finally, treatment with NaSPh and mercaptophenylacetic acid (MPAA) in a 5:1 mixture of DMF/Na2HPO4 buffer at pH 7.2 fully solubilized the glycine, allowing complete reaction of the MeNbz group. A 94:6 ratio of elongated product to MeNbz hydrolysis (10a:10b) was observed (entry 6). A similar trend in reactivity was observed for isoleucine (entries 7-10) and alanine (entries 11-14). However, because it is more nucleophilic than the primary amines, proline displaced MeNbz with complete conversion in the absence of any thiol additive (entries 15-19). As mentioned earlier, Weinreb amine was not an ideal nucleophile in this chemistry.[3] The improved reactivity of proline is likely caused by the more exposed nitrogen lone pair in the cyclic amine relative to the linear amine. For all amino acids tested under the optimized conditions, hydrolysis rates were maintained below 15%. Lastly, it was previously established that Hünig's base is mild enough to avoid epimerization in conversion of MeNbz peptides to the corresponding acids, esters, and amides. Nevertheless, because the conditions were slightly different here, the extent of epimerization observed in entry 17 was tested. Interestingly, proline addition led to 3% epimerization (FIG. 33). It was hypothesized that the in-situ generated phenyl thioester might be more prone to epimerization than the MeNbz group and that the longer time needed for complete conversion in the proline case would increase the amount of epimerization observed. To test this hypothesis, the stereointegrity of C-terminal L-Ala with isoleucine as the nucleophile was evaluated. Epimerization for either the C-terminal L- or D-Ala is determined.

It was expected that when performed on the resin, the nucleophilic reactions would become slower as the peptide length was increased, leading to more non-elongated acid by-products. Therefore, the optimized reaction conditions from FIG. 28 were tested on the longer peptide H-LYRAGL-RAY-MeNbz-Gly-Rink (SEQ ID NO: 7).

GLP-1(7-36) underwent the optimized alanine elongation conditions and after global deprotection yielded GLP-1(7-36)A in 4% isolated yield.

Example 2. Exploiting the MeDbz Linker to Generate Protected or Unprotected C-Terminally Modified Peptides. C-Terminally modified peptides are important for the development and delivery of peptide based pharmaceuticals because they improve peptide activity, stability, hydrophobicity, and membrane permeability. Additionally, the vulnerability of C-terminal esters to cleavage by endogenous esterases makes them excellent pro-drugs.[3] Meanwhile, C-terminal thioesters and hydrazides are critical to the synthesis of larger peptide targets via native chemical ligation (NCL) and non-cysteine NCL. Despite the demand for C-terminally modified peptides, there remain significant limitations in the available strategies to access them by chemical synthesis. Variations at the C-terminus traditionally require repetition of the solid-phase peptide synthesis (SPPS) on a different linker for each desired C-terminal moiety[2a,2c], or the use of a C-terminal glycine. Solution-phase activation of protected C-terminal acids risks epimerization. Side-chain anchoring strategies are limited by the need for particular amino acids at the C-terminus and by epimerization during the activation of the C-terminal carboxylic acid. Recent efforts to diversify the C-terminus from a single SPPS effort suffer from epimerization, require extended reaction times or heating, are incompatible with common cysteine protecting groups,[15] or require pre-functionalization of the peptide.

For broad utility, the ideal functionalization method should employ a commercially available resin/linker, use convenient reagents for activation, undergo reaction with a variety of nucleophiles of varying steric and nucleophilic properties, and proceed at ambient temperature without epimerization of the C-terminal residue. Furthermore, the approach should enable the user to select between the production of protected peptides and the solution-phase diversification of unprotected peptides. To date, no report has demonstrated the achievement of this set of objectives. In this Example, the commercially available MeDbz linker was commandeered to realize these goals for the first time.

Figure 34:
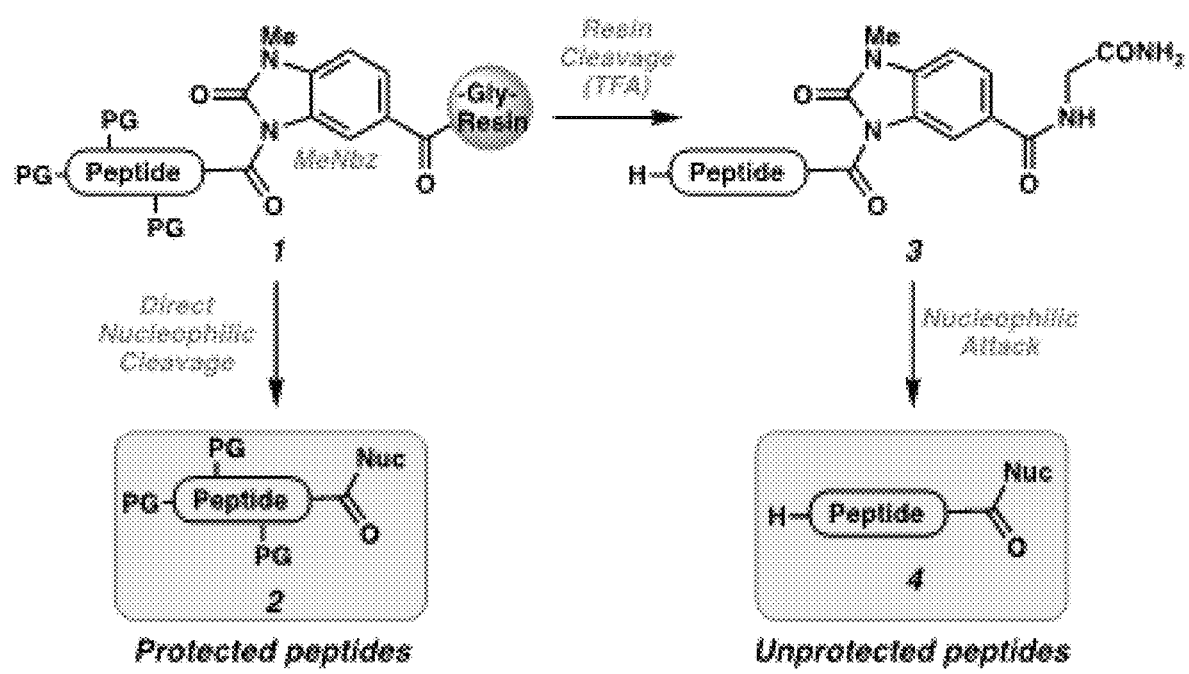

The strategy for divergent C-terminal functionalization is outlined in FIG. 34. MeNbz-Linked resin-bound peptides 1 are accessible upon activation of the MeDbz linker.[18] It was envisioned that these peptides could be directly cleaved to afford protected C-terminally modified peptides 2 or treated with trifluoroacetic acid (TFA) to afford side-chain-deprotected MeNbz peptides 3. Upon exposure to various nucleophiles, unprotected peptides 3 would be diversified at the C terminus (4). The susceptibility of this linker to attack by weaker nucleophiles than thiols[4] and hydrazine remains under-explored. Additionally, the direct nucleophilic cleavage of this linker from resin has not been reported.

To establish the reactivity of the resin-bound MeNbz group, MeNbz-linked tripeptides (5a-c) were treated with a variety of nucleophiles (FIGS. 35A and 35B). A Gly residue was installed at the C-terminus (5a) to avoid concerns related to epimerization at this stage. The generation of thioesters from MeNbz is well established, 18b so the investigation began with nitrogen nucleophiles. As the smallest nucleophile, it was expected that bubbling with ammonia would readily induce cleavage from the resin. Indeed, complete removal of the peptide from the resin was observed after bubbling with a balloon of $NH_3$ for 1.5 h. The corresponding tripeptide carboxamide was isolated in 41% yield. Primary amines of varying nucleophilicity were evaluated. Butylamine and 3-azidopropylamine proceeded with complete conversion. Propargyl amine and benzyl amine are slightly less nucleophilic than primary alkyl amines, but both are efficient in displacing MeNbz. Importantly, azide and propargyl containing products can be further diversified via azide-alkyne cycloaddition. The least nucleophilic amine tested was aniline, which led to minimal product formation. However, in the presence of 5 equiv Hünig's base, aniline displacement proceeded with 53% conversion, allowing access to peptide N-aryl amides via this strategy.

Because of the unique biological properties of C-terminal esters,[3] there was interest in the ability of oxygen nucleophiles to displace MeNbz. To maximize the amount of RO— in solution, alcohols were combined with KOtBu and added to the swelled resin.[14] Primary alkoxides reacted with complete conversion to afford the corresponding esters. Steric hindrance in the nucleophile slows the reaction considerably, with isopropoxide proceeding to only 62% conversion. Although benzyl oxide was also less efficient than the alkoxides, phenoxide led to complete conversion. Finally, treatment with aqueous NaOH resulted in >99% conversion to the corresponding carboxylic acid. Overall, a variety of strong, weak, and even branched N- and O-nucleophiles are effective in cleaving MeNbz from the resin. Additionally, hindered C-terminal amino acids and bulky protecting groups are tolerated. Tripeptide 5b (X=Ile) and 5c (X=Arg (Pbf)) reacted with excellent conversion when treated with ammonia, butylamine, or MeOH/KOtBu.

Figure 36:
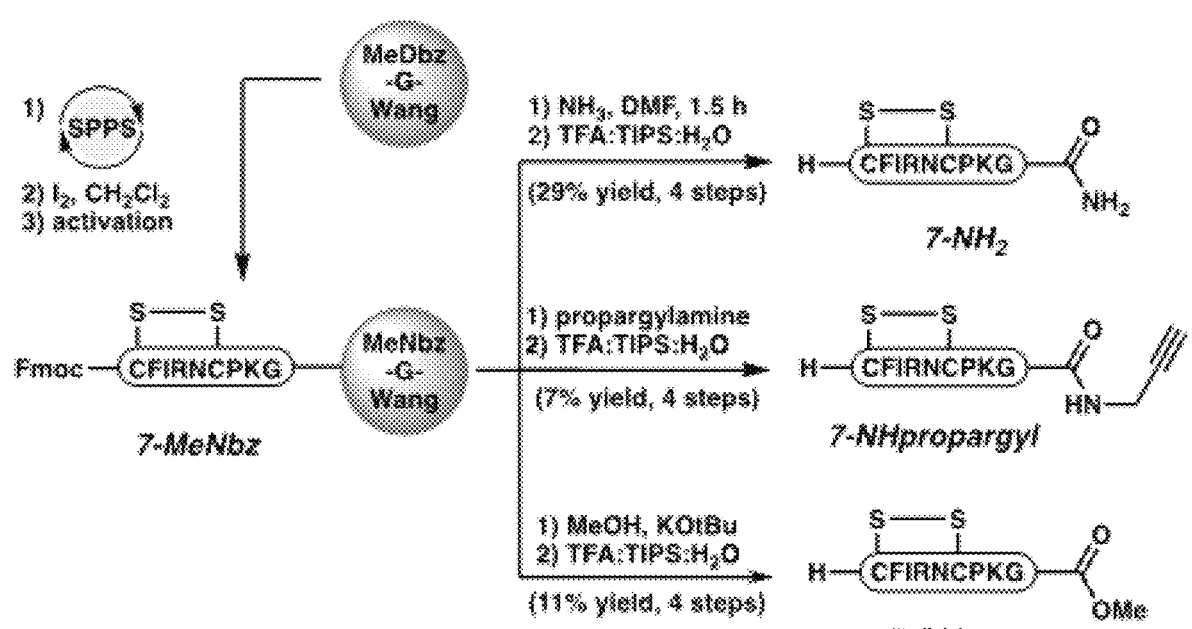
FIG. 36. Divergent synthesis of conopressin G and analogs.

To demonstrate the convenience of this approach, conopressin G (7), a C-terminal carboxamide-containing vasopressin homolog isolated from the venom of piscivorous Conus snails, and 2 analogs (FIG. 36) were synthesized. This neuroactive peptide contains a single disulfide bridge and a C-terminal carboxamide. Following SPPS, the disulfide bond was accessed via iodine-mediated Trt cleavage/oxidation. The MeDbz linker was activated in the presence of the disulfide linkage. The resin was divided into 3 vessels and treated with ammonia, propargyl-amine, or MeOH/KOtBu, cleaving the peptide from the resin and generating the fully protected conopressins. The remaining protecting groups were removed, affording native conopressin (7-$NH_2$) in 29% isolated yield, propargyl conopressin (7-NHpropargyl) in 7% yield, and conopressin methyl ester (7-OMe) in 11% A isolated yield. Additionally, the active portion of glucagon-like peptide-1, GLP-1(7-36) was synthesized. GLP-1 receptor agonists are state-of-the-art pharmaceutical agents, with 16 different GLP-1 agonists in clinical trials as of 2015. GLP-1(7-36)-MeNbz-Gly-Resin was treated with ammonia in DMF for 1.5 h to afford native GLP-1(7-36) in >99% conversion and 4% isolated yield (27% crude).

With the viability of the method established, the next focus was evaluating the extent of epimerization under these conditions using Fmoc-AW(Boc)A-MeNbz-Gly-Wang (8).[25] No epimerization was observed upon displacement of MeNbz by butylamine (FIGS. 40A and 40B). Given the extent of epimerization observed by Meldal and co-workers in the presence of KOt-Bu (50%),[14] epimerization during treatment with KOt-Bu/MeOH was expected. Indeed, under these conditions, 15% epimerization was observed. Dawson reported<2% epimerization during the activation of C-terminal Tyr-Dbz in the presence of Hünig's base.[18] Thus, it was hypothesized that under similar conditions, an epimerization-free ester modification might be feasible. Indeed, treatment with 5 equiv Hünig's base in MeOH led to complete conversion with no observable epimerization. Analogously, employing Hünig's base in water led to the carboxylic acid with no epimerization. Additionally, H-AW (Boc)H(Trt)-MeNbz-Gly-Wang was prepared and cleaved with ammonia. No epimerization was observed.[25]

An advantage of the MeDbz linker is that the activated linker (MeNbz) is stable to typical post-SPPS manipulations including resin cleavage, purification, 18 and storage. Thus, it was imagined that solution-phase modifications of unprotected peptides would be feasible. The ability to diversify the C-terminus of an unprotected peptide in solution would be ideal for situations where the SPPS itself led to multiple close-eluting products. Rather than diversification during resin cleavage followed by several challenging purifications, a single purification could be executed, followed by solution-phase diversification of the pure MeNbz peptide. For simplicity during evaluation of the nucleophile scope, the tripeptide H-AWA-MeNbz-Gly-$NH_2$(9) (SEQ ID NO: 32), which does not have any nucleophilic side chains was generated. The crude peptide was dissolved in MeCN then treated with the nucleophile. To avoid epimerization, Hünig's base was employed when a stoichiometric base was needed. A variety of primary amines were tolerated, leading to complete conversion in 30 min (FIGS. 37A and 37B). In contrast to the resin-bound approach, complete conversion was also observed for less nucleophilic amines such as aniline. Hydrazine and hydroxylamine were excellent nucleophiles, affording the corresponding hydrazide and hydroxamide with >99% conversion. The reaction has some sensitivity to steric effects, as demonstrated by the low conversion observed with Weinreb amine. Primary alkyl, benzyl, and phenyl alcohols were competent nucleophiles in the presence of Hünig's base, whereas i-PrOH was more sluggish (61% conversion, 5 h). In the presence of aqueous NaOH, the carboxylic acid was observed. Finally, the β-amino alcohol could be generated by $NaBH_4$ addition.

The solution-phase C-terminal diversification of MeNbz-linked peptides is notable in the ready accessibility of the activated peptide, the mild conditions, the short reaction times, and the scope of nucleophiles demonstrated. For maximum utility, the functionalization of unprotected peptides should be compatible with residues bearing nucleophilic side chains.[17] Thus, H-AKTWA-MeNbz-Gly (SEQ ID NO: 35) (11) was synthesized and subjected to various nucleophiles for 30 min (FIGS. 38A and 38B). The reactions were quenched by dilution with 1:1 MeCN: $H_2O$, and the product distribution (12a:12b:12c) was analyzed by HPLC integration. The functionalized acyclic peptide (12a) was the desired target. Unreacted peptide 11 was hydrolyzed to the corresponding acid (12b) during the quench and apart from entry 2, this product represents unreacted starting material. Attack of either the N terminus or the side chain of Lys or Thr would afford a cyclic peptide. The sole macrocyclic product was assigned as 12c based on the reactivity of the primary amine relative to an α-branched amine or alcohol and by independent synthesis of the head-to-tail cyclized lactam.[25]

In 1:1 $MeCN:BuNH_2$, only the intermolecular amide product was observed. Repeating this reaction with 1:1:1 $MeCN:H_2O:BuNH_2$ still led primarily to the amide with 7% hydrolysis occurring during the reaction. Thus, the modification has reasonable tolerance to aqueous conditions when an excess of nucleophile is employed. Propargylamine was similarly effective, while the reduced nucleophilicity of aniline resulted in an 8:92 ratio of amide to macrolactam. Peptide hydrazides[19] and hydroxamides[31] were generated with no macrocycle formation. In contrast, treatment with Weinreb amine led to 89% conversion to the macrolactam. Functionalization with MeOH proceeded with complete conversion to a 42:58 ratio of methyl ester to lactam. In the presence of a non-nucleophilic base, the lactam was formed with 91% conversion.

Finally, sodium borohydride reduction was slower, likely because of the MeCN co-solvent, but no macrocycle was observed.

Peptides containing Pro and Gly are generally more prone to macrocyclization. Peptides 13 and 14 were evaluated to determine whether more cyclization-prone substrates could be efficiently functionalized (FIGS. 39A and 39B). The proclivity of these peptides towards macrocyclization was validated by control reactions with MeOH/Hünig's base and Hünig's base alone (entry 2,3,5,6). Peptides 13 and 14 were more prone to cyclization than AKTWA (SEQ ID NO: 23). Yet, in the presence of a 50:47.5:2.5 ratio of butylamine/$MeCN/H_2O$, excellent conversion to the butyl amide (13a, 14a) was observed for both peptides (entry 1,4). All remaining nucleophilic side chains were evaluated by replacing Lys with Ser (15), Cys (16), and Tyr (17). In all cases, the butyl amide and the methyl ester could be accessed with no hydrolysis or macrocyclization. Omission of the exogenous nucleophile confirmed that these peptides form macrocycles during the short reaction (entry 9, 12, 15). Overall, intermolecular C-terminal functionalization with strong, unhindered nucleophiles occurs with excellent selectivity. Finally, to probe the utility of the in-solution chemistry, Fmoc-GLP-1(7-36)-MeDbz-Gly-Rink was activated and cleaved from the resin to afford unprotected GLP-1(7-36)-MeNbz-Gly-$NH_2$ in 45% crude yield. Subsequent displacement with butylamine in $MeCN/H_2O$ led to GLP-1(7-36)-NHBu with >99% conversion and 22% isolated yield.

In summary, a versatile method for the C-terminal functionalization of peptides is described. The approach is tolerant of a variety of nucleophiles, yielding carboxamides, alkyl and aryl amides and esters, hydrazides, hydroxamides, acids, and amino alcohols from a single SPPS effort. Either protected or unprotected peptides can be used. When employing a large excess of a strong nucleophile, both water and unprotected nucleophilic side chains are tolerated. The utility of this approach has been demonstrated via the divergent synthesis of 3 conopressin G derivatives and 2 GLP-1(7-36) derivatives. This convenient method will facilitate the synthesis of important bioactive peptides with diverse C-terminal functionalities, enabling investigation of their potential as pharmaceutical agents.

Example 3. Epimerization-Free Access to C-Terminal Cysteine Peptide Acids, Carboxamides, Secondary Amides, and Esters. C-Terminal cysteine peptides, including prenylated and farnesylated peptides, disulfide linked peptide toxins, and insulinotropic peptides, comprise an important but synthetically challenging class of biologically active peptides. Many of these peptides are modified at the C-terminus. C-terminal modifications such as esters and amides can be critical to maintaining a peptide's active conformation, in vivo activity, and pharmacokinetics; therefore, the ability to vary the peptide structure in this location is crucial to drug development efforts. Although several methods have been reported for C-terminal functionalization after solid-phase peptide synthesis (SPPS) is complete, these approaches either result in epimerization when applied to C-terminal Cys peptides or the applicability of the method to C-terminal Cys peptides is not addressed. While activation of the C-terminal carboxylic acid can induce epimerization via oxazolone formation in most amino acids, cysteine is also prone to epimerization via direct deprotonation during its attachment to the resin and upon prolonged or repeated exposure to base (i.e., during peptide elongation via Fmoc SPPS). Therefore, even the preparation of simple carboxylic acids or carboxamides of C-terminal cysteine peptides can be fraught with contamination by epimerized products,[1f-g,13a] reducing the overall yield and complicating the purification of the target peptides.

In this Example, the first mild and convenient method for the epimerization-free diversification of peptides bearing a C-terminal cysteine is described. Carboxylic acids, primary and secondary amides, and esters are accessed without epimerization or diketopiperazine and piperidinyl-alanine side products. This strategy was applied to the total syntheses of the nicotinic acetylcholine receptor (nAChR) antagonist α-conotoxin Iml and the insect pheromone α-factor.[1]

Figure 41:
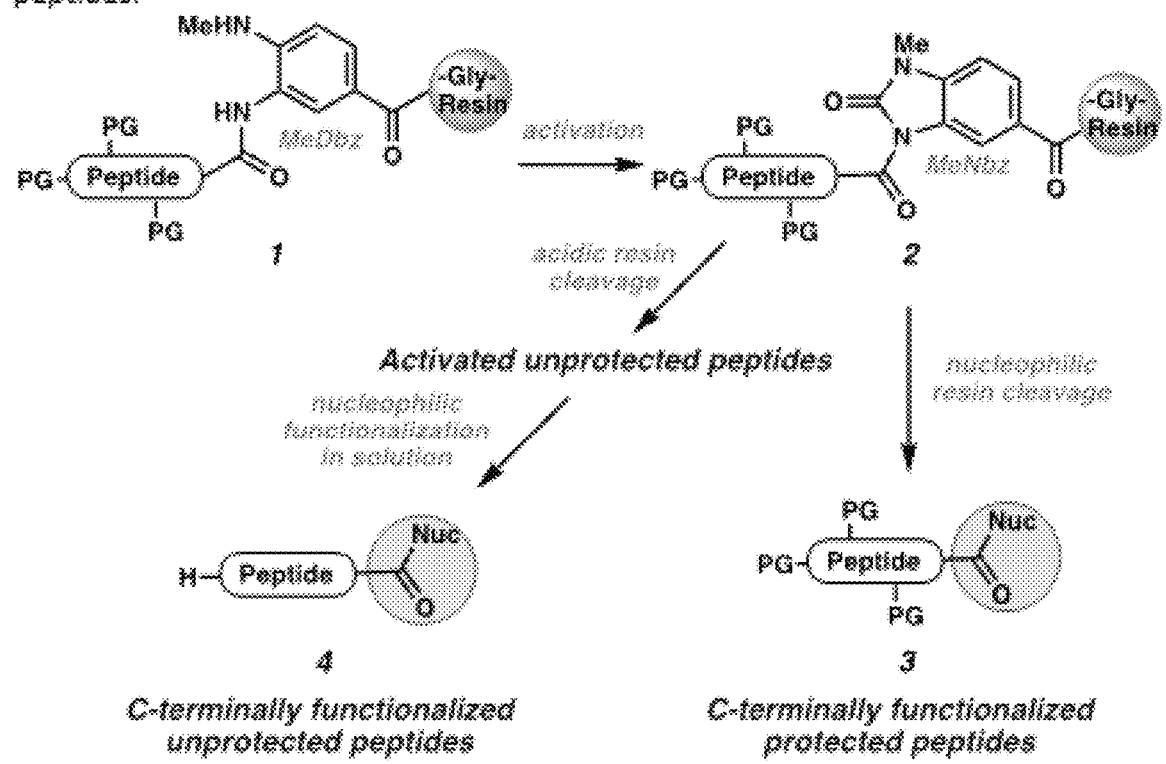
FIG. 41. Strategy for C-terminal peptide modification.

It was hypothesized that a recently reported strategy for C-terminal functionalization of non-Cys peptides (FIG. 41) would be mild enough to enable preparation of C-terminal Cys peptide acids, primary and secondary amides, and esters without epimerization. In C-terminal modification chemistry, activation of the methyl-diaminobenzoyl (MeDbz) linker (1→2) followed by nucleophilic cleavage of the N-acyl urea (MeNbz) group yields various protected (3) or unprotected (4) peptides. For epimerization-free functionalization at Cys, the attachment of the first amino acid,[21b] peptide elongation, linker activation, and nucleophilic attack all occur without epimerization of the unusually acidic[23] Cys α-stereocenter. It was expected that the C-terminal diversification strategy would accomplish these objectives.

Figure 47:
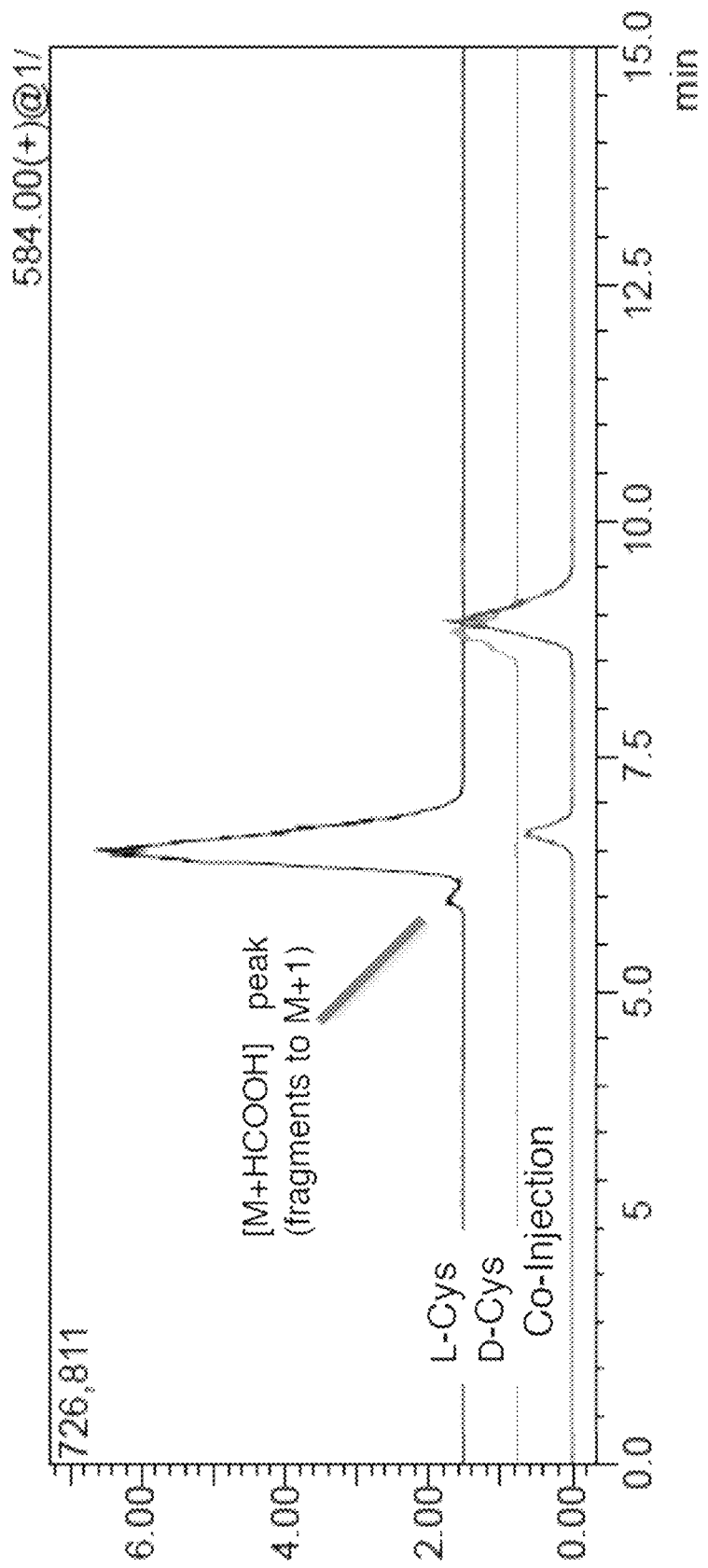
FIG. 47. L-Cys, D-Cys, and co-injection after SPPS, gradient 40-95% MeCN/H$_2$O+1% HCOOH over 15 min.
Figure 48:
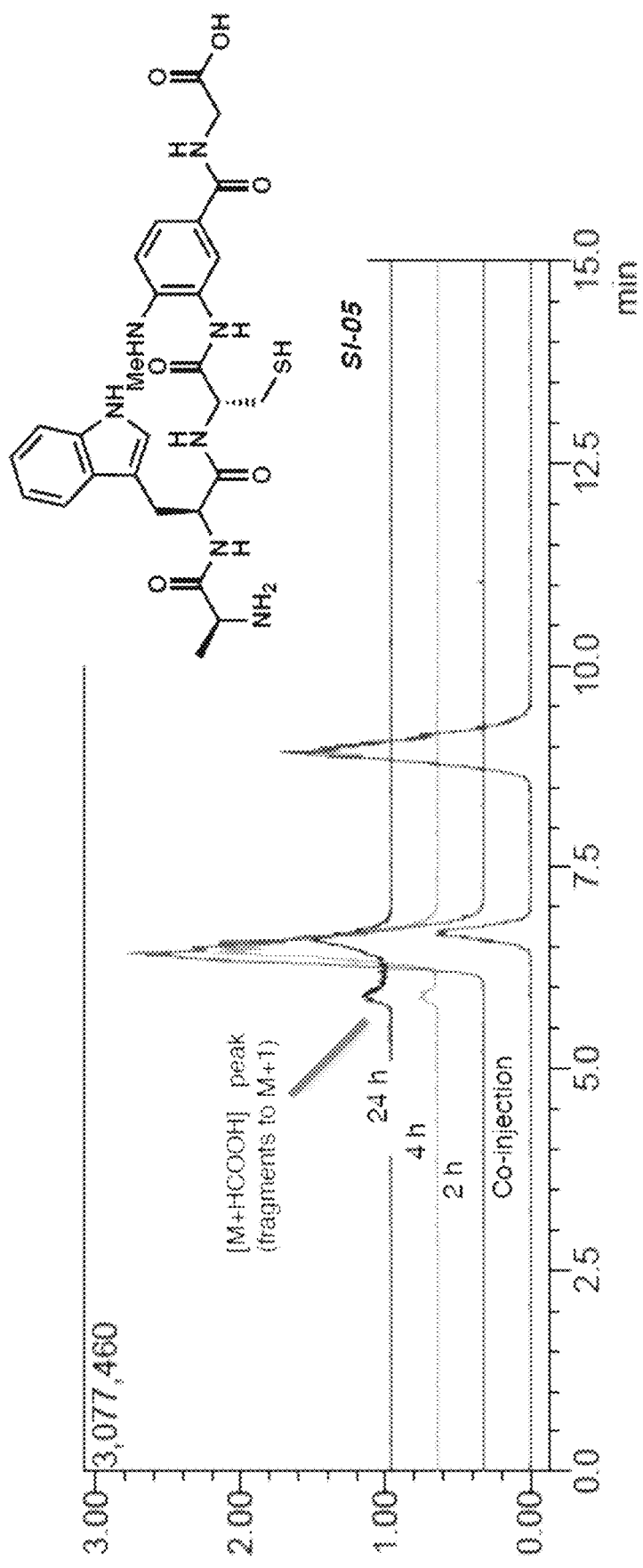
FIG. 48. L-Cys after 24 h, 4 h, 2 h, and co-injection, gradient 40-95% MeCN/H$_2$O+1% HCOOH) over 15 min.

Although the MeDbz group should not be sufficiently activating to cause epimerization during prolonged piperidine exposure, the stereochemical integrity of the Cys residue under these conditions unequivocally was sought. Cys (Trt) was selected for these experiments because of its extreme tendency toward epimerization.[14] Thus, tripeptide Boc-Ala-Trp(Boc)-Cys(Trt)-MeDbzGly-Wang (SEQ ID NO: 28) was synthesized and exposed to 20% piperidine/DMF over 2, 4, and 24 h. The peptides were then cleaved under acidic conditions to afford H-AWC-MeDbz-Gly-OH (SEQ ID NO: 28). As expected, no epimerization was detected immediately following SPPS or after piperidine exposure at any time point (FIGS. 47 and 48).

Next, the ability of the activated MeNbz linker to undergo nucleophilic displacement without inducing epimerization of the C-terminal cysteine was examined. Epimerization-prone Cys(Trt)-terminated peptides were first evaluated with N and O nucleophiles (5, FIGS. 42A and 42B). This began with displacement by ammonia because of its small size and the relatively low pKa of +NH$_4$. Formation of the target peptide (6, Nuc=NH$_2$) with complete conversion and no detectable epimerization in 54% isolated yield (entry 1) was observed. Benzylamine, which has a similar pKa, was evaluated next. Treatment of the activated linker with neat BnNH$_2$ led to 16% epimerization (entry 2). However, using only 5 equiv benzylamine in MeCN, the product was formed with no detectable epimerization (entry 3). With 1.1 equiv butylamine, complete conversion is observed with no epimerization. Because 5 equiv butylamine led to epimerization in the Trt case, these conditions were used in the remaining experiments.

It was expected that other commercially available Cys PGs would be less prone to epimerization than Trt. First, the Acm group in MeCN (entry 7) was evaluated, and <1% epimerization in the formation of the C-terminal Cys(Acm) butylamide was found. Next, Mob, Bn, StBu, and tBu were tested with BuNH$_2$ in MeCN. In all cases, no epimerization was detected (entries 8-11). Turning attention to alcohol nucleophiles, MeOH/KOtBu with Cys(Trt) as a benchmark[9] was tested and 42% epimerization (entry 12) was found. However, in the presence of 5 equiv Hünig's base (DIEA) in MeOH, no epimerization was observed (entry 13). Because of the lower conversion in this case, the use of a 1:1 MeOH/phosphate buffer solvent mixture (pH 8) was also investigated. In this case, complete conversion was observed while maintaining no detectable epimerization (entry 14). Even carboxylic acid derivatives with a C-terminal Cys(Trt) can be difficult to access without epimerization. Therefore, water was investigated as a nucleophile in the presence of Hünig's base. In this case, the reaction was slower, and the product acid was observed with <1% epimerization (entry 15). Thus, with only one exception, all nucleophiles tested react with the activated C terminus without any observed epimerization, regardless of the protecting group on cysteine.

Figure 43:
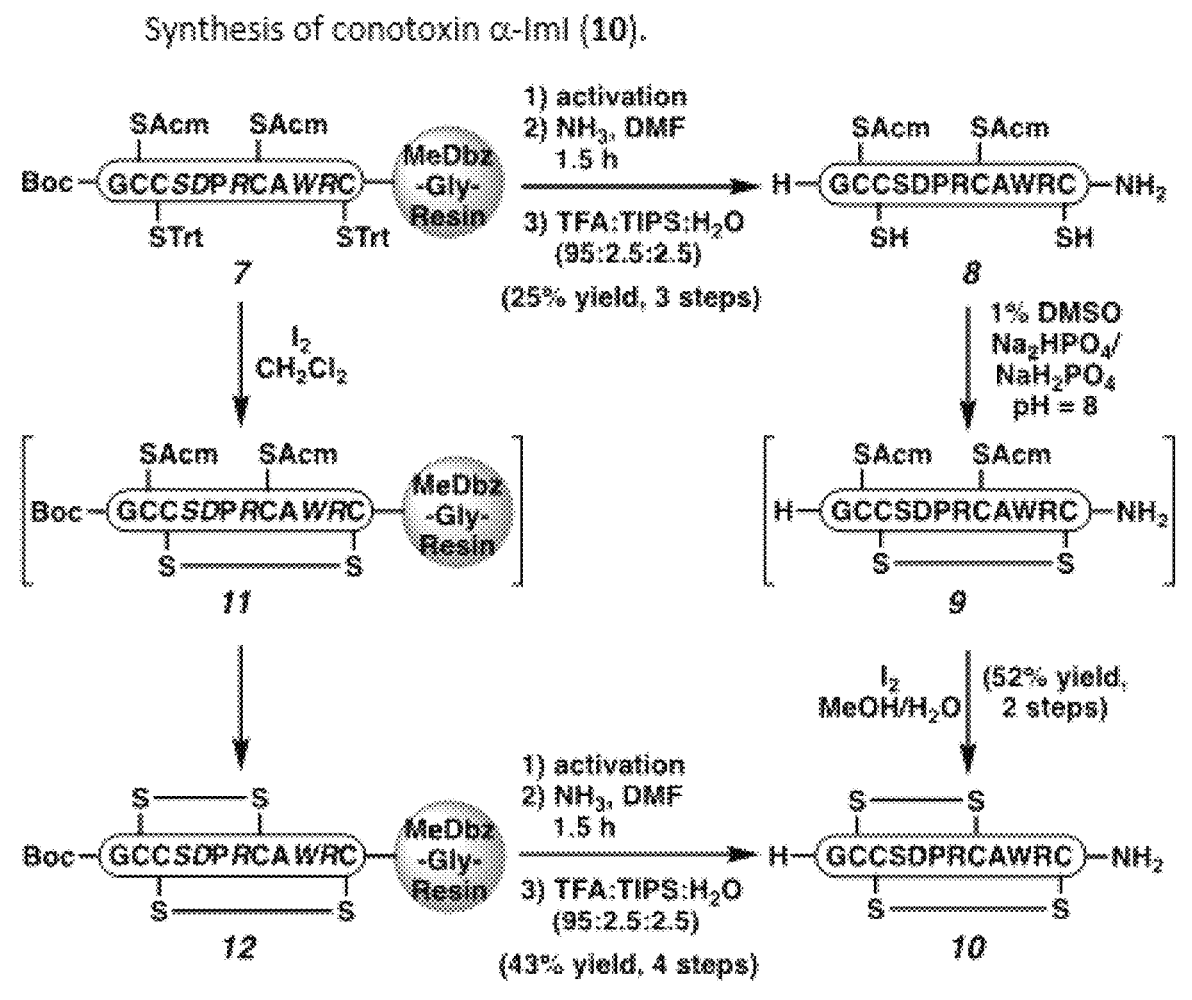

Next, the viability of this cleavage strategy in the context of more complex peptides was evaluated. Because of interest in disulfide-linked neuroactive peptides, the C-terminal carboxamide α-conotoxin Iml (10), a sub-type selective nicotinic acetylcholine receptor antagonist isolated from the venom of Conus *imperialis* marine snails (FIG. 43) was targeted. Both the C-terminal carboxamide and the correct disulfide bond connectivity are important to the bioactivity of α-Iml (10).[28] Thus, peptide 7 was activated and cleaved with ammonia to yield the fully protected peptide carboxamide. Acidic removal of protecting groups and HPLC purification gave the reduced peptide 8 in 25% isolated yield. The first disulfide was formed in the presence of air in 1% DMSO in phosphate buffer at pH 8 (peptide 9). Subsequent iodine treatment removed both Acm groups and induced oxidation to form the native conotoxin (10) in 52% isolated yield over both folding steps. Co-injection of with a commercially available standard confirmed the correct folding.[24] Alternatively, on-resin folding with iodine could be followed by MeDbz activation, cleavage with NH$_3$, and side-chain deprotection to afford conotoxin 10 in 43% isolated yield; however, this approach gives a mixture of folded products, as expected.

Although the direct cleavage of activated MeNbz led to no detectable epimerization for most Cys(PG) in FIG. 42, alkyl amide formation remained problematic for Cys(Trt) peptides. To address the special case of the butylamine/Cys (Trt) combination, an alternative strategy using cysteine itself as the nucleophile for cleavage of MeNbz from the resin was developed.[25] The resulting peptide bearing a free Cys side chain would serve as a synthetic equivalent to a C-terminal Cys(Trt) because Trt is generally removed during or immediately following resin cleavage. Recently, C-terminal cysteine peptide acids were synthesized using an N-(2-hydroxy-5-nitrobenzyl)-cysteine (N-Hnb-Cys) crypto-thioester approach.[25b] Although this method enabled access to a challenging Pro-Cys linkage at the C terminus, elevated temperatures and long reaction times were required to generate the C-terminal thioester, leading to undesired side products. That application of the NCL-based elongation tactic to MeNbz-based C-terminal modification would lead to a convenient method to access challenging targets at ambient temperature and with short reaction times was expected.

The NCL elongation approach was tested with H-AWA-MeNbz-Gly-Rink (SEQ ID NO: 32) peptides (13), which were treated with free cysteine, H-Cys-OEt, H-Cys-NH$_2$, or H-Cys-NHBu in the presence of Hünig's base (FIGS. 44A and 44B). Protected peptides Boc-AW(Boc)AC-OH (14a), Boc-AW(Boc)AC-OEt (14b), and Boc-AW(Boc)AC-NH$_2$ (14c) were formed with complete conversion (entries 1-3), while Boc-AW(Boc)AC-NHBu (14d) was formed with 38% conversion. The elongation was more efficient in solution,[21] and unprotected peptides 14e-h were accessed with quantitative conversion (entries 5-8). In some cases, the excess cysteine in the reaction resulted in cystine formation (entries 4, 8). This can be avoided by replacing water with NCL buffer, or a separate reduction step can be performed to access the reduced peptide product.[24] It was assumed that the mildly basic reaction conditions would result in rapid S to N acyl transfer upon cysteine thiol addition either on resin or in solution. In-situ generation of the backbone amide was confirmed by independent synthesis of H-AWAC-OH SEQ ID NO: 38) followed by co-injection with 14f.[24] The extent of product peptide epimerization was evaluated for the ethyl ester (14b), which is the most epimerization-prone derivative. Comparison to a co-injection of H-AWA(D-Cys)-OEt (SEQ ID NO: 30) confirmed that the product peptides are not epimerized under the reaction conditions (FIGS. 49A and 49B).

The NCL elongation of a series of peptides varying in length and hydrophobicity both on the resin and in solution (FIGS. 45A and 45B) was next executed. The unprotected peptide H-AKTWA-MeNbz-Gly (SEQ ID NO: 35) (15a) was functionalized in solution to afford H-AKTWAC-OH (15b) (SEQ ID NO: 36) with complete conversion. C-terminal proline-containing peptide 16a was cleaved from resin using H-Cys-OH to afford protected H-AKTWPC-OH (16b) (SEQ ID NO: 37) with 10% conversion over 4 h. Repeating this reaction in solution on unprotected peptide led to complete conversion after 1 h. Elongation of Boc-LYRAGL-RAY (SEQ ID NO: 11) (20a) proceeded with resin cleavage and complete conversion in the presence of DMF and NCL buffer. Hydrophobic peptide 18, a fragment of amyloid β(Aβ(36-42)), was elongated both on resin (entry 5) and in solution (entry 6). On-resin elongation proved challenging for this substrate (10% conversion), while complete conversion was observed in solution. Overall, for shorter or non-hydrophobic peptides, this chemistry can be executed on resin and in the absence of added thiol. In challenging cases, resin cleavage and standard native chemical ligation afford the target peptides.

Figure 46:
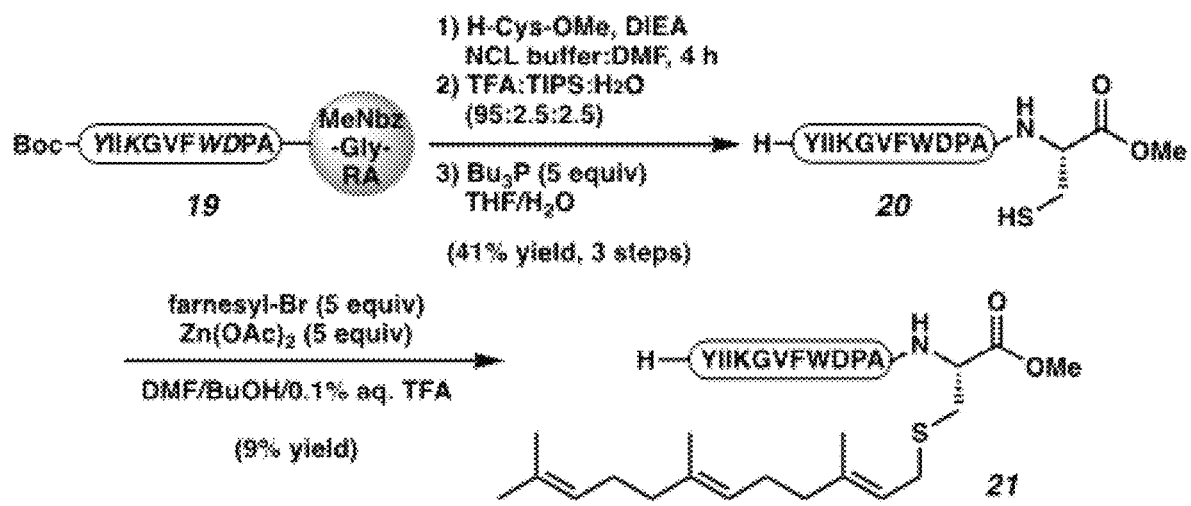
FIG. 46. Synthesis of α-factor by cysteine elongation.

To confirm the viability of this approach in the context of a complex natural product, the total synthesis of the insect pheromone α-factor (21, FIG. 46), which requires both the C-terminal ester and the prenyl group for bioactivity. 1 e-h was executed. Protected des-farnesyl α-factor was generated by displacement of peptide 19 with cysteine methyl ester. Although the elongation was conducted in NCL buffer, the cystine-functionalized α-factor was still observed. Side-chain deprotection, cystine reduction, and HPLC purification afforded peptide 20 in 41% A yield over 3 steps. Alkylation per the reported conditions afforded α-factor in 9% yield (21).[37]

In summary, a broadly applicable strategy for the direct diversification of C-terminal cysteine peptides with no detectable epimerization of the C-terminal cysteine residue is described. An alternative strategy was also presented for the special case of alkyl amide generation. No previous report has demonstrated the functionalization of a C-terminal cysteine peptide to access various carboxylic acid derivatives without epimerization of the α-stereocenter. Importantly, the target peptides are prepared without observation of either diketopiperazine or piperidinylalanine side products. The utility of these methods was demonstrated in the preparation of the disulfide-linked conotoxin α-Iml, bearing a C-terminal cysteine carboxamide and insect pheromone α-factor, which bears a C-terminal cysteine methyl ester.

Numerous references have been made to patents, printed publications, journal articles and other written text throughout this specification (referenced materials herein). Each of the referenced materials are individually incorporated herein by reference in their entirety for their referenced teaching.

The particulars shown herein are by way of example and for purposes of illustrative discussion of the preferred embodiments of the subject matter described herein only and are presented in the cause of providing what is believed to be the most useful and readily understood description of the principles and conceptual aspects of various embodiments of the subject matter. In this regard, no attempt is made to show structural details of the subject matter in more detail than is necessary for the fundamental understanding of the subject matter described herein, the description taken with the drawings and/or examples making apparent to those skilled in the art how the several forms of the subject matter described herein may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

REFERENCES FOR BACKGROUND, SUMMARY OF INVENTION, AND DETAILED DESCRIPTION

[1] Tsomaia, N. Peptide therapeutics: Targeting the undrugable space, Eur. J. Med. Chem. 2015, 94, 459-470.

[2] Wu, L. C.; Chen, F.; Lee, S. L.; Raw, A.; Yu, L. X. Building parity between brand and generic peptide products: Regulatory and scientific considerations for quality of synthetic peptides, Int. J. Pharm. 2017, 518, 320-334.

[3] (a) Thieriet, N.; Guibé, F.; Albericio, F. Solid-Phase Peptide Synthesis in the Reverse (NC) Direction, Org. Lett. 2000, 2, 1815-1817. (b) Sasubilli, R.; Gutheil, W. G. General Inverse Solid-Phase Synthesis Method for C-Terminally Modified Peptide Mimetics, J. Comb. Chem. 2004, 6, 911-915. (c) Rai, A.; Gutheil, W. G. A Dde resin based strategy for inverse solid-phase synthesis of amino terminated peptides, peptide mimetics and protected peptide intermediates, J. Pept. Sci. 2005, 11, 69-73. (d) Johansson, A.; Akerblom, E.; Ersmark, K.; Lindeberg, G.; Hallberg, A. An Improved Procedure for N- to C-Directed (Inverse) Solid-Phase Peptide Synthesis, J. Comb. Chem. 2000, 2, 469-507. (e) Bordusa, F.; Ullmann, D.; Jakubke, H.-D. Protease-Catalyzed Peptide Synthesis from N- to C-Terminus: An Advantagous Strategy, Angew. Chem. Int. Ed. 1997, 36, 1099-1101. (f) Henkel, B.; Zhang, L.; Bayer, E. Investigations on Solid-Phase Peptide Synthesis in N-to-C Direction (Inverse Synthesis), Eur. J. Org. Chem. 1997, 2161-2168. (g) Broadbridge, R. J.; Akhtar, M. First efficient synthesis of α-MAPI, Chem. Commun. 1998, 1449-1450. (h) Le'ger, R.; Yen, R.; She, M. W.; Lee, V. J.; Hecker, S. J. N-Linked solid phase peptide synthesis, Tetrahedron Lett. 1998, 38, 4171-4174. (i) Lipshutz, B. H.; Shin, Y.-J. A new silyl linker for reverse-direction solid-phase peptide synthesis, Tetrahedron Lett. 2001, 42, 5629-5633.

[4] (a) Arbour, C. A.; Saraha, H. Y.; McMillan, T. F.; Stockdill, J. L. Exploiting the MeDbz Linker To Generate Protected or Unprotected C-Terminally Modified Peptides, Chem. Eur. J. 2017, 23, 12484-12488. (b) Arbour, C. A.; Saraha, H. Y.; Kondasinghe, T. D.; Vorlicek, T. L.; Stockdill, J. L.* Epimerization-Free Access to C-Terminal Cysteine Peptide Acids, Carboxamides, Amides, and Esters. Submitted for publication on Aug. 14, 2017.

[5] Arbour, C. A.; Stamatin, R. E.; Stockdill, J. L. Sequence Diversification by Divergent C-Terminal Elongation of Peptides. Submitted for publication on 09/08/17.

[6] El-Faham, A.; Albericio, F. Peptide Coupling Reagents, More than a Letter Soup, Chem. Rev. 2011, 111, 6557-6602.

[7] Lukszo, J.; Patterson, D.; Albericio, F.; Kates, S. A. 3-(1-Piperidinyl)alanine formation during the preparation of C-terminal cysteine peptides with the Fmoc/t-Bu strategy, Lett. Pept. Sci. 1996, 3, 157-166.

[8] (a) Geiger, T.; Clarke, S. Deamidation, Isomerization, and Racemization at Asparaginyl and Aspartyl Residues in Peptides, J. Biol. Chem. 1987, 262, 785-794. PMID: 3805008 (b) Stephenson, R. C.; Clarke, S. Succinimide Formation from Aspartyl and Asparaginyl Peptides as a Model for the Spontaneous Degradation of Proteins, J. Biol. Chem. 1989, 264, 6164-

6170. PMID:2703484 (c) Mergler, M.; Dick, F.; Sax, B.; Weiler, P.; Vorherr, T. The Aspartimide Problem in Fmoc-based SPPS. Part I. J. Pept. Sci. 2003, 9, 36-46. (d) Behrendt, R.; Huber, S.; White, P. Preventing aspartimide formation in Fmoc SPPS of Asp-Gly containing peptides—practical aspects of new trialkylcarbinol based protecting groups, J. Pept. Sci. 2016, 22, 92-97.

[9] Ramos-Tomillero, I.; Rodriguez, H.; Albericio, F. Tetrahydropyranyl, a Nonaromatic Acid-Labile Cys Protecting Group for Fmoc Peptide Chemistry, Org. Lett. 2015, 17, 1680-1683.

[10] (a) Cherkupally, P.; Acosta, G. A.; Ramesh, S.; De la Torre, B. G.; Govender, T.; Kruger, H. G.; Albericio, F. Solid-phase peptide synthesis (SPPS), C-terminal vs. side-chain anchoring: a reality or a myth, Amino Acids 2014, 46, 1827-1838. (b) Juvekar, V.; Kim, K.-T.; Gong, Y.-D. Highly Efficient Synthetic Method on Pyroacm Resin Using the Boc SPPS Protocol for C-terminal Cysteine Peptide Synthesis, Bull. Korean Chem. Soc. 2017, 38, 54-62.

[11] Barany, G.; Han, Y.; Hargittai, B.; Liu, R.-Q.; Varkey, J. T. Side-Chain Anchoring Strategy for Solid-Phase Synthesis of Peptide Acids with C-Terminal Cysteine, Biopolymers (Pept. Sci.) 2003, 71, 652-666.

[12] (a) Cruz, L. J.; de Santos, V.; Zafaralla, G. C.; Ramilo, C. A.; Zeikus, R.; Gray, W. R.; Olivera, B. M. Invertebrate Vasopressin/Oxytocin Homologs, J. Biol. Chem. 1987, 262, 15821-15824. PMID:3680228 (b) Martínez-Padrón, M.; Edstrom, J.; Wickham, M.; Lukowiak, K. Modulation of Aplysia Californica Siphon Sensory Neurons by Conopressin G, J. Exp. Biol. 1992, 172, 79-105; (c) Salzet, M.; Bulet, P.; Van Dorsselaer, A.; Malecha, J. Isolation, structural characterization and biological function of a lysine-conopressin in the central nervous system, Eur. J. Biochem. 1994, 217, 897-903.

[13] Johnson, L. M.; Barrick, S.; Hager, M. V.; McFedries, A.; Homan, E. A.; Rabaglia, M. E.; Keller, M. P.; Attie, A. D.; Saghatelian, A.; Bisello, A.; Gellman, S. H. A Potent α/β-Peptide Analogue of GLP-1 with Prolonged Action in Vivo, J. Am. Chem. Soc. 2014, 136, 12848-12851.

[14] Fosgerau, K.; Hoffmann, T. Peptide therapeutics: current status and future directions, Drug Disc. Today 2015, 20, 122-128.

[15] Han, Y.; Albericio, F.; Barany, G. Occurrence and Minimization of Cysteine Racemization during Stepwise Solid-Phase Peptide Synthesis, J. Org. Chem. 1997, 62, 4307-4312.

[16] (a) Dawson, P. E.; Muir, T. W.; Clark-Lewis, I.; Kent, S. B. Synthesis of proteins by native chemical ligation, Science 1994, 266, 776-669. (b) Johnson, E. C. B.; Kent, S. B. H. Insights into the mechanism and catalysis of the native chemical ligation reaction, J. Am. Chem. Soc. 2006, 128, 6640-6646.

[17] Carpino, L. A.; El-Faham, A.; Albericio, F. Racemization Studies During Solid-Phase Peptide Synthesis Using Azabenzotriazole-Based Coupling Reagents, Tetrahedron Lett. 1994, 35, 2279-2282.

[18] (a) Yu, H.-M.; Chen, S.-T.; Wang, K.-T. Enhanced Coupling Efficiency in Solid-Phase Peptide Synthesis by Microwave Irradiation, J. Org. Chem. 1992, 57, 4781-4784. (b) Palasek, S. A.; Cox, Z. J.; Collins, J. M. Limiting racemization and aspartimide formation in microwave-enhanced Fmoc solid phase peptide synthesis, J. Pept. Sci. 2007, 13, 143-148. (c) Petersen, S. L.; Tofteng, A. P.; Malik, L.; Jensen, K. J. Microwave heating in solid-phase peptide synthesis, Chem. Soc. Rev. 2012, 41, 1826-1844.

[19] (a) Paradis-Bas, M.; Tulla-Puche, J.; Albericio, F. The road to the synthesis of "difficult peptides", Chem. Soc. Rev. 2016, 45, 631-654. (b) de L. Milton, R. C.; Milton, S. C. F.; Adams, P. A. Prediction of Difficult Sequences in Solid-Phase Peptide Synthesis, J. Am. Chem. Soc. 1990, 112, 6039-6046. (c) Johnson, T.; Quibell, M.; Owen, D.; Sheppard, R. C. A reversible protecting group for the amide bond in peptides. Use in the synthesis of 'difficult sequences', J. Chem. Soc., Chem. Commun. 1993, 369-372. (d) Zinieris, N.; Zikos, C.; Ferderigos, N. Improved solid-phase peptide synthesis of 'difficult peptides' by altering the microenvironment of the developing sequence, Tetrahedron Lett. 2006, 47, 6861-6864. (e) Zahariev, S.; Guarnaccai, C.; Pongor, C. I.; Quaroni, L.; Čemažar, M.; Pongor, S. Synthesis of 'difficult' peptides free of aspartimide and related products, using peptoid methodology, Tetrahedron Lett. 2006, 47, 4121-4124. (f) Rahman, S. A.; El-Kafrawy, A.; Hattaba, A.; Anwer, M. F. Optimization of solid-phase synthesis of difficult peptide sequences via comparison between different improved approaches, Amino Acids 2007, 33, 531-536. (g) Tickler, A. K.; Wade, J. D. Overview of Solid Phase Synthesis of "Difficult Peptide" Sequences, Curr. Protoc. Protein Sci. 2007, 50, 18.8.1-18.8.6. (h) Bacsa, B.; Horvati, K.; Bosze, S.; Andreae, F.; Kappe, C. O. Solid-Phase Synthesis of Difficult Peptide Sequences at Elevated Temperatures: A Critical Comparison of Microwave and Conventional Heating Technologies, J. Org. Chem. 2008, 73, 7532-7542. (i) Coin, I. The depsipeptide method for solid-phase synthesis of difficult peptides, J. Pept. Sci. 2010, 16, 223-230.

[20] (a) Kent, S. B. H. Chemical Synthesis of Peptides and Proteins, Ann. Rev. Biochem. 1988, 57, 957-989. (b) Miranda, L. P.; Alewood, P. F. Accelerated chemical synthesis of peptides and small proteins, Proc. Natl. Acad. Sci. USA 1999, 96, 1181-1186. PMCID: PMC15437

[21] (a) Hyde, C.; Johnson, T.; Sheppard, R. C. Internal Aggregation during Solid Phase Peptide Synthesis. Dimethyl Sulfoxide as a Powerful Dissociating Solvent, J. Chem. Soc., Chem. Common. 1992, 0, 1573-1575. (b) Krchnák, V.; Flegelová, Z.; Vágner, J. Aggregation of resin-bound peptides during solid-phase peptide synthesis, Int. J. Pept. Protein Res. 1993, 42, 450-454. (c) Warrass, R.; Wieruszeski, J.-M.; Boutillon, C.; Lippens, G. High-Resolution Magic Angle Spinning NMR Study of Resin-Bound Polyalanine Peptides, J. Am. Chem. Soc. 2000, 122, 1789-1795. (d) Fernandez-Escamilla, A.-M.; Rousseau, F.; Schymkowitz, J.; Serrano, L. Prediction of sequence-dependent and mutational effects on the aggregation of peptides and proteins, Nature Biotechnol. 2004, 22, 1302-1306.

[22] (a) Larsen, B. D.; Holm, A. Incomplete Fmoc deprotection in solid-phase synthesis of peptides, J. Pept. Protein Res. 1994, 43, 1-9. (b) Dettin, M.; Pegoraro, S.; Rovero, P.; Bicciato, S.; Bagno, A.; Bello, C. D. SPPS of difficult sequences, J. Pept. Res. 1997, 49, 103-111.

[23] (a) Wöhr, T.; Mutter, M. Pseudo-Prolines in Peptide Synthesis: Direct Insertion of Serine and Threonine Derived Oxazolidines in Dipeptides, Tetrahedron Lett. 1995, 36, 3847-3848. (b) Wöhr, T.; Wahl, F.; Nefzi, A.; Rohwedder, B.; Sato, T.; Sun, X.; Mutter, M. Pseudo-Prolines as Solubilizing, Structure-Disrupting Protection Technique in Peptide Synthesis, J. Am. Chem. Soc. 1996, 118, 9218-927. (c) White, P.; Keyte, J. W.; Bailey, K.; Bloomberg, G. Expediting the Fmoc Solid Phase Synthesis of Long Peptides Through the Application of Dimethyloxazolidine Dipeptides, J. Pept. Sci. 2004, 10, 18-26.

[24] (a) Sohma, Y.; Sasaki, M.; Hayashi, Y.; Kimura, T.; Kiso, Y. Novel and effieicent synthesis of difficult sequence-containing peptides through O—N intramolecular acyl migration reation of O-acyl isopeptides, Chem. Commun. 2004, 124-125. (b) Taniguchi, A.; Sohma, Y.; Kimura, M.; Okada, T.; Ikeda, K.; Hayashi, Y.; Kimura, T.; Hirota, S.; Matsuzaki, K.; Kiso, Y. "Click Peptide" Based on the "0-Acyl Isopeptide Method": Control of Aβ1-42 Production from a Photo-Triggered Aβ1-42 Analogue, J. Am. Chem. Soc. 2006, 128, 696-697. (c) Youhei, S.; Yoshiya, T.; Taniguchi, A.; Kimura, T.; Hayashi, Y.; Kiso, Y. Development of 0-Acyl Isopeptide Method, Biopolymers (Pept. Sci.), 2007, 88, 253-262. (d)Yoshiya, T.; Uemura, T.; Maruno, T.; Kubo, S.; Kiso, Y.; Sohma, Y.; Kobayashi, Y.; Yoshizawa-Kumagaye, K.; Nishiuchi, Y. O-Acyl isopeptide method: development of an O-acyl isodipeptide unit for Boc SPPS and its application to the synthesis of Aβ1-42 isopeptide, J. Pept. Sci. 2014, 20, 669-674.

[25] (a) Sarma, K. D.; Zhang, J.; Huang, Y.; Davidson, J. G. Amino Acid Esters and Amides for Reductive Amination of Mucochloric Acid: Synthesis of Novel γ-Lactams, Short Peptides, and Antiseizure Agent Levetiracetam (Keppra®), Eur. J. Org. Chem. 2006, 3730-3737. (b) Pels, K.; Kodadek, T. Solid-Phase Synthesis of Diverse Peptide Tertiary Amides By Reductive Amination, ACS Comb. Sci. 2015, 17, 152-155. (c) Chen, D.; Disotuar, M. M.; Xiong, X.; Wang, Y.; Chou, D. H.-C., Selective N-terminal functionalization of native peptides and proteins, Chem. Sci. 2017, 8, 2717-2722.

[26] (a) Quibell, M.; Turnell, W. G.; Johnson, T. Reversible Modification of the Acid Labile 2-Hydroxy-4-methoxybenzyl(Hmb) Amide Protecting Group: A simple scheme yielding Backbone Substituted Free Peptides, Tetrahedron Lett. 1994, 35, 2237-2238. (b) Simmonds, R. G. Use of the Hmb backbone-protecting group in the synthesis of difficult sequences, Int. J. Pept. Protein Res. 1996, 47, 36-41. (c) Zeng, W.; Ragamey, P.-O.; Rose, K.; Wang, Y.; Bayer, E. Use of Fmoc-N-(2-hydroxy-4-methyoxybenzyl) amino acids in peptide synthesis, J. Pept. Res. 1997, 49, 273-279.

[27] (a) Botti, P.; Carrasco, M. R.; Kent, S. B. H. Native chemical ligation using removable $N^{\alpha}$-(1-phenyl-2-mercaptoethyl) auxiliaries, Tetrahedron Lett. 2001, 42, 1831-1833. (b) Marinzi, C.; Offer, J.; Longhi, R.; Dawson, P E. An o-nitrobenzyl scaffold for peptide ligation: synthesis and applications, Bioorg. Med. Chem. 2004, 12, 2749-2757. (c) Loibl, S. F.; Harpaz, Z.; Seitz, 0. A Type of Auxiliary for Native Chemical Peptide Ligation beyond Cysteine and Glycine Junctions, Angew. Chem. Int. Ed. 2015, 54, 15055-15059.

[28] (a) Li, X.; Danishefsky, S. J. New Chemistry with Old Functional Groups: On the Reaction of Isonitriles with Carboxylic Acids—A Route to Various Amide Types, J. Am. Chem. Soc. 2008, 130, 5446-5448; (b) Wu, X.; Li, X.; Danishefsky, S. J. Thio-mediated two-component coupling reaction of carboxylic acids and isonitriles under mild conditions, Tetrahedron Lett. 2009, 50, 1523-1525. (c) Wilson, R. M.; Stockdill, J. L.; Wu, X.; Li, X.; Vadola, P. A.; Park, P. K.; Wang, P.; Danishefsky, S. J. Angew. Chem. Int. Ed. 2012, 51, 2834-2848.

[29] (a) Sieminski, A. L.; Semino, C. E.; Gong, H.; Kamm, R. D. Primary sequence of ionic self-assembling peptide gels affects endothelial cell adhesion and capillary morphogenesis, J. Biomed. Mater. Res. A. 2008, 87, 494-504. (b) Zhang S.; Altman, M. Peptide self-assembly in functional polymer science and engineering, React. Funct. Polym. 1999, 41, 91-102.

[39] (a) Clippingdale, A. B.; Wade, J. D.; Barrow, C. J. The amyloid-beta peptide and its role in Alzheimer's disease, J. Pept. Sci. 2001, 7, 227-249. (b) Jang, H.; Arce, T.; Ramachandran, S.; Kagan, B. L.; Lal, R.; Nussinov, R. Disordered amyloidogenic peptides may insert into the membrane and assemble into common cyclic structural motifs, Chem. Soc. Rev. 2014, 43, 6750-6764 (c) Glenner, G. G.; Wong, C. W. Alzheimer's disease: initial report of the purification and characterization of a novel cerebrovascular amyloid protein, Biochem. Biophys. Res. Commun. 1984, 120, 885-890. (d) Kang, J.; Lamaire, H.-G.; Unterbeck, A.; Salbaum, J. M.; Masters, C. L.; Grzeschik, K.-H.; Multhaup, G.; Beyreuther, K.; Müller-Hill, B. The precursor of Alzheimer's disease amyloid A4 protein resembles a cell-surface receptor, Nature 1987, 325, 733-736. (e) Butterfield, D. A.; Swomley, A. M.; Sultana, R. Amyloid □-Peptide (1-42)-Induced Oxidative Stress in Alzheimer Disease: Importance in Disease Pathogenesis and Progression, Antioxid. Redox Signal. 2013, 19, 823-835.

[31] (a) Bedford, J.; Hyde, C.; Johnson, T.; Jun, W.; Owen, D.; Quibell, M.; Sheppard, R. C. Amino acid structure and "difficult sequences" in solid phase peptide synthesis, Int. J. Pept. Protein Res. 1992, 40, 300-307. (b) Huang, Y.-C.; Guan, C.-J.; Tan, X.-L.; Chen, C.-C.; Guo, Q.-X.; Li, Y.-M. Accelerated Fmoc solid-phase synthesis of peptides with aggregation-disrupting backbones, Org. Biomol. Chem. 2015, 13, 1500-1506. (c) Zhang, S.; Lockshin, C.; Cook, R.; Rich, A. Unusually stable beta-sheet formation in an ionic self-complementary oligopeptide, Biopolymers 1994, 34, 663-672. (d) Zhang, S.; Holmest, T.; Lockshin, C.; Rich, A. Spontaneous assembly of a self-complementary oligopeptide to form a stable macroscopic membrane, Proc. Natl. Acad. Sci. USA 1993, 90, 3334-3338. PMCID: PMC46294 (e) Holmes, T. C.; Lacalle, S. d.; Su, X.; Liu, G.; Rich, A.; Zhang, S. Extensive neurite outgrowth and active synapse formation on self-assembling peptide scaffolds, Proc. Natl. Acad. Sci. USA 2000, 97, 6728-6733. (f) Zhang, S. Emerging biological materials through molecular self-assembly, Biotechnol. Adv. 2002, 20, 321-339.

[32] Salah, K. B. H.; Inguimbert, N. Efficient Microwave-Assisted One Shot Synthesis of Peptaibols Using Inexpensive Coupling Reagents, Org. Lett. 2014, 16, 1783-1785.

[33] Aussedat, B.; Fasching, B.; Johnston, E.; Sane, N.; Nagorny, P.; Danishefsky, S. J. Total Synthesis of the α-Subunit of Human Glycoprotein Hormones: Toward Fully Synthetic Homogeneous Human Follicle-Stimulating Hormone, J Am. Chem. Soc. 2012, 134, 3532-3541. (b) Stockdill, J. L.; Brailsford, J. A.; Aussedat, B. A.; Danishefsky, S. J. Unpublished work toward β-Thyroid Stimulating Hormone.

[34] (a) Ramos-Tomillero, I.; Paradis-Bas, M.; Moreira, I. d. P. R.; Bofill, J. M.; Nicolas, E.; Albericio, F. Formylation of Electron-Rich Aromatic Rings Mediated by Dichloromethyl Methyl Ether and TiCl4: Scope and Limitations, Molecules 2015, 20, 5409-5422. (b) García, O.; Nicolás, E.; Albericio, F. o-Formylation of electron-rich phenols with dichloromethyl methyl ether and TiCl4, Tetrahedron Lett. 2003, 44, 4961-4963.

[35] Shelton, P. T.; Jensen, K. J. Linkers, resins, and general procedures for solid-phase peptide synthesis. In Methods in Molecular Biology; Jensen, K.; Tofteng, S. P.; Pedersen, S., Ed.; Humana Press: Totowa, N.J., 2013; Vol. 1047; p 23-41.

[36] (a) Ollivier, N.; Desmet, R.; Drobecq, H.; Blanpain, A.; Boll, E.; Leclercq, B.; Mougel, A.; Vicogne, J.; Melnyk, 0. A simple and traceless solid phase method simplifies the assembly of large peptides and the access to challenging proteins, Chem. Sci. 2017, 8, 5362-5370. (b) Ollivier, N.; Desmet, R.; Drobecq, H.; Blanpain, A.; Boll, E.; Leclercq, B.; Mougel, A.; Vicogne, J.; Melnyk, O. Correction: A simple and traceless solid phase method simplifies the assembly of large peptides and the access to challenging proteins, Chem. Sci. 2017, 8, 5802-5802.

[37] Thomas, F. Fmoc-based peptide thioester synthesis with self-purifying effect: heading to native chemical ligation in parallel formats, J. Pept. Sci. 2013, 19, 141-147.

[38] (a) Qvortrup, K.; Komnatnyy, V. V.; Nielsen, T. E. A Photolabile Linker for the Solid-Phase Synthesis of Peptide hydrazides and Heterocycles, Org. Lett. 2014, 16, 4782-4785. (b) Åkerblom, E. B.; Nygren, A. S.; Agback, K. H. Six new photolabile linkers for solid-phase synthesis. 1. Methods of preparation, Molec. Divers. 1997, 3, 137-148.

[39] Shin, D.-S.; Lee, Y.-S. Synthesis of Pentafluorophenyl Esters of Nitroveratryloxycarbonyl-Protected Amino Acids, Synlett 2009, 20, 3307-3310.

[40] Tseng, S. Y.; Wang, C.-C.; Lin, C.-W.; Chen, C.-L.; Yu, W.-Y.; Chen, C.-H.; Wu, C.-Y.; Wong, C.-H. Glycan Arrays on Aluminum-Coated Glass Slides, Chem. Asian J. 2008, 3, 1395-1405.

[41] Choi, S. K.; Thomas, T.; Li, M.-H.; Kotlyar, A.; Desdai, A.; Baker, J. R. Light-controlled release of caged doxorubicin from folate receptor-targeting PAMAMdendrimer nanoconjugate, Chem. Commun. 2010, 46, 2632-2634.

[42] Lee, J.; Ryu, T.; Park, S.; Lee, P. H. Indium Tri(isopropoxide)-Catalyzed Selective Meerwein-Ponndorf-Verley Reduction of Aliphatic and Aromatic Aldehydes, J. Org. Chem. 2012, 77, 4821-4835.

[43] Amblard, M.; Fehrentz, J.-A.; Martinez, J.; Subra, G. Peptide Synthesis and Applications, Howl, J. Ed.; Springer Science & Business Media: Berlin, 2005; Vol. 298; p 16.

[44] (a) Kang, T. S.; Vivekanandan, S.; Jois S. D. S.; Kini, R. M. Peptide amidation: Production of peptide hormones in vivo and in vitro, Angew. Chem. Int. Ed. 2005, 44, 6333-6337. (b) Doh, H. J.; Cho, W. J.; Yong, C. S.; Choi, H. G.; Kim, J. S.; Lee, C. H.; Kim, D. D. Synthesis and evaluation of Ketorolac ester prodrugs for transdermal delivery, J. Pharm. Sci. 2003, 92, 1008-1017.

[45] (a) Meienhofer, J.; Waki, M.; Heimer, E. P.; Lambros, T. J.; Makofske, R. C.; Chang, C. D. Solid phase synthesis without repetitive acidolysis. Preparation of leucyl-alanyl-glycyl-valine using 9-fluoroenylmethyloxycarbonylamino acids, Int. J. Pept. Protein Res. 1979, 13, 35-42. (b) Eissler, S.; Kley, M.; Bachle, D.; Loidl, G.; Meier, T.; Samson, D. Substitution determination of Fmoc-substituted resins at different wavelengths, J. Pept. Sci. 2017, 23, 757-762.

[46] Kretschy, N.; Holik, A.-K.; Somoza, V.; Stengele, K.-P.; Somoza, M. M. Next-Generation o-Nitrobenzyl Photolabile Groups for Light-Directed Chemistry and Microarray Synthesis, Angew. Chem. Int. Ed. 2015, 54, 8555-8559.

References for Example 1

Kent SB. J Pept Sci. 2015 March; 21(3):136-8. doi: 10.1002/psc.2754;

C. A. Arbour, H. Y. Saraha, T. F. McMillan and J. L. Stockdill, Chem. Eur. J., 2017, doi:10.1002/chem.201703380;

(a) J. B. Blanco-Canosa and P. E. Dawson, Angew. Chem. Int. Ed., 2008, 47, 6851-6855;

(b) J. B. Blanco-Canosa, B. Nardone, F. Albericio and P. E. Dawson, J. Am. Chem. Soc., 2015, 137, 7197-7209.

S. K. Mahto, C. J. Howard, J. C. Shimko and J. J. Ottesen, ChemBioChem, 2011, 12, 2488-2494;

C. A. Arbour, T. D. Kondasinghe, H. Y. Saraha, T. L. Vorlicek and J. L. Stockdill, Submitted;

H. E. Elashal, Y. E. Sim and M. Raj, Chem. Sci., 2017, 8, 117-123; Nucleophilic Reactivity of Primary and Secondary Amines in Acetonitrile.pdf.

References for Example 2

[1] B. A. Eipper, D. A. Stoffers, R. E. Mains, Annu. Rev. Neurosci. 1992, 15, 57-85.

[2] (a) J. Alsina, F. Albericio, Biopolymers 2003, 71, 454-477; (b) M. F Songster, G. Barany, Methods Enzymol. 1997, 289, 126-174; (c) W.-J. Fang, T. Yakovleva, J. V. Aldrich, Biopolymers (Pept. Sci.) 2011, 96, 715-722.

[3] (a) J. A. Zablocki, F. S. Tjoeng, P. R. Bovy, M. Miyano, R. B. Garland, K. Williams, L. Schretzman, M. E. Zupec, J. G. Rico, R. J. Lindmark, M. V. Toth, D. E. McMackins, S. P. Adams, S. G. Panzer-Knodle, N. S. Nicholson, B. B. Taite, A. K. Salyers, L. W. King, J. G. Campion, L. P. Feigen, Bioorg. Med. Chem. 1995, 3, 539-551; (b) H.-J. Doh, W.-J. Cho, C.-S. Yong, H.-G. Choi, J. S. Kim, C.-H. Lee, D.-D. Kim, J. Pharm. Sci. 2003, 92, 1008-1017.

[4] (a) F. Thomas, J. Pept. Sci. 2013, 19, 141-147; (b) Z. P. Gates, B. Dhayalan, S. B. H. Kent, Chem. Commun. 2016, 52, 13979-13982; (c) H. Li, S. Dong, Sci. China Chem. 2017, 60, 201-213 and references therein.

[5] (a) J.-S. Zheng, S. Tang, Y.-K. Qi, Z.-P. Wang, L. Liu, Nat. Protoc. 2013, 8, 2483-2495; (b) J. Li, Y. Li, Q. He, Y. Li, H. Li, L. Liu, Org. Biomol. Chem. 2014, 12, 5435-5441; (c) S.-S. Wang, J. Org. Chem. 1975, 40, 1235-1239.

[6] (a) P. E. Dawson, T. W. Muir, I. Clark-Lewis, S. B. Kent, Science, 1994, 266, 776-779; (b) E. C. B. Johnson, S. B. H. Kent, J. Am. Chem. Soc. 2006, 128, 6640-6646.

[7] S. Shang, Z. Tan, S. J. Danishefsky, Proc. Natl. Acad. Sci. U.S.A. 2011, 108, 5986-5989.

[8] Enzymatic approaches have also been reported. See: (a) R. Kulathila, K. A. Merkler, D. J. Merkler, Nat. Prod. Rep. 1999, 16, 145-154; (b) T. Nuijens, C. Cusan, J. A. W. Kruijtzer, D. T. S. Rijkers, R. M. J. Liskamp, P. J. L. M. Quaedflieg, J. Org. Chem. 2009, 74, 5145-5150; (c) J. M. Antos, G.-L. Chew, C. P. Guimaraes, N. C. Yoder, G. M. Grotenbreg, M. W.-L. Popp, H. D. Ploegh, J. Am. Chem. Soc. 2009, 131, 10800-10801, (d) T. Nuijens, E. Piva, J. A. W. Kruijtzer, D. T. S. Rijkers, R. M. J. Liskamp, P. J. L. M. Quaedflieg, Tetrahedron Lett. 2012, 53, 3777-3779; (e) C. G. Boeriu, A. E. Frissen, E. Boer, K. Kekem, D.-J. van Zoelen, I. F. Eggen, J. Mol. Catal. B: Enzym. 2010, 66, 33-42; (f) B. Wu, H. J. Wijma, L. Song, H. J. Rozeboom, C. Poloni, Y. Tian, M. I. Arif, T. Nuijens, P. J. L. M. Quaedflieg, W. Szymanski, B. L. Feringa, D. B. Janssen, ACS Catal. 2016, 6, 5405-5414.

[9] E. Nicolás, J. Clemente, M. Perelló, F. Albericio, E. Pedroso, E. Giralt, Tetrahedron Lett. 1992, 33, 2183-2186.

10 M. Góngora-Benítez, J. Tulla-Puche, F. Albericio, ACS Comb. Sci. 2013, 15, 217-228; (b) Qvortrup, K.; V. V. Komnatnyy, T. E. Nielsen, Org. Lett. 2014, 16, 4782-4785, (c) H. T. Ten Brink, J. T. Meijer, R. V. Geel, M. Damen, D. W. P. M. LOwik, J. C. M. Van Hest, J. Pept. Sci. 2006, 12, 686-692.

[11] J. A. Camarero, A. Adeva, T. W. Muir Lett. Pept. Sci. 2000, 7, 17-21.

[12] B. Henkel, L. Zhang, E. Bayer, Liebigs Ann. Recl. 1997, 2161-2168.

[13] (a) Z. Huang, D. J. Derksen, J. C. Vederas, Org. Lett. 2010, 12, 2282-2285; (b) V. Diaz-Rodriguez, E. Ganusova, T. M. Rappe, J. M. Becker, M. D. Distefano, J. Org. Chem. 2015, 80, 11266-11274.

[14] J. Hansen, F. Diness, M. Meldal, Org. Biomol. Chem. 2016, 14, 3238-3245.

[15] (a) H. E. Elashal, Y. E. Sim, M. Raj, Chem. Sci. 2017, 8, 117-123; (b) H. E. Elashel, R. D. Cohen, M. Raj, Chem. Commun. 2016, 52, 9699-9702.

[16] (a) J. A. Camarero, B. J. Hackel, J. J. de Yoreo, A. R. Mitchell, J. Org. Chem. 2004, 69, 4145-4151; (b) Y. Kwon, K. Welsh, A. R. Mitchell, J. A. Camarero, Org. Lett. 2004, 6, 3801-3804; (c) R. A. Turner, R. J. Weber, R. S. Lokey, Org. Lett. 2010, 12, 1852-1855.

[17] (a) P. Wang, K. T. Shaw, B. Wingham, R. Ramage, Tetrahedron Lett. 1998, 39, 8719-8720, (b) A. A. Vinogradov, M. D. Simon, B. L. Pentelute, Org. Lett. 2016, 18, 1222-1225.

[18] (a) J. B. Blanco-Canosa, P. E. Dawson, Angew. Chem. Int. Ed. 2008, 47, 6851-6855; (b) S. K. Mahto, C. J. Howard, J. C. Shimko, J. J. Ottesen ChemBioChem, 2011, 12, 2488-2494; (c) J. B. Blanco-Canosa, B. Nardone, F. Albericio, P. E. Dawson, J. Am. Chem. Soc. 2015, 137, 7197-7209.

[19] (a) P. Siman, V. Karthikean, M. Nikolav, W. Fischle, A. Brik, Angew. Chem. Int. Ed. 2013, 52, 8059-8063; (b) H. P. Hemantha, S. D. Bavikar, Y. Herman-Bachinsky, N. Haj-Yahya, S. Bondalapati, A. Ciechanover, A. Brik J. Am. Chem. Soc. 2014, 136, 2665-2673; (c) S. Buhler, J. H. Akkerdaas, T. A. Pertinhez, R. Van Ree, A. Dossena, S. Sforza, T. Tedeschi, J. Pept. Sci. 2017, 23, 282-293.

[20] (a) R. Pascal, D. Chauvey, R. Sola, Tetrahedron Lett. 1994, 34, 6291-6294; (b) B. Zacharie, G. Sauve, C. Penney, Tetrahedron 1993, 49, 10489-10500.

[21] (a) A. M. Bray, N. J. Maeji, A. G. Jhingran, R. M. Valerio, Tetrahedron Lett. 1991, 32, 6163-6166, (b) A. M. Bray, R. M. Valerio, N. J. Maeji, Tetrahedron Lett. 1993, 34, 4411-4414, (c) R. Sola, P. Saguer, M.-L. David, R. Pascal, J. Chem. Soc., Chem. Commun. 1993, 1786-1788.

[22] In FIG. 35, non-gaseous nucleophiles were left overnight (19 h) to ensure complete conversion. However, complete conversion is observed after as little as 1.5 h (see SI).

[23] J.-P. Ebran, N. Dendane, O. Melnyk, Org. Lett. 2011, 13, 4336-4339.

[24] (a) R. Huisgen, Proc. Chem. Soc. Lond. 1961, 357-396; (b) V. V. Rost-ovtsev, L. G. Green, V. V. Fokin, K. B. Sharpless, Angew. Chem. Int. Ed. 2002, 41, 2596-2599; (c) C. W. Tornøe, C. Christensen, M. Meldal, J. Org. Chem. 2002, 67, 3057-3064; (d) A. A. H. A. Fuaad, F. Azmi, M. Skwarczynski, I. Toth, Molecules 2013, 18, 13148-13174; (e) W. Tang, M. L. Becker, Chem. Soc. Rev. 2014, 43, 7013-7039.

[25] See the supporting information for details.

[26] (a) L. J. Cruz, V. de Santos, G. C. Zafaralla, C. A. Ramilo, R. Zeikus, W. R. Gray, B. M. Olivera, J. Biol. Chem. 1987, 262, 15821-15824; (b) M. Martinez-Padron, J. Edstrom, M. Wickham, K. Lukowiak, J. Exp. Biol. 1992, 172, 79-105; (c) M. Salzet, P. Bulet, A. Van Dorsselaer, J. Malecha, Eur. J. Biochem. 1994, 217, 897-903.

[27] K. Fosgerau, T. Hoffmann, Drug Disc. Today 2015, 20, 122-128.

[28] Meldal and co-workers observed 1:1 D:L-Ala after exposure to C3H7-SH and 10 equiv KOt-Bu for 24 h.14

[29] Samples stored as a solid or a solution in MeCN at −20° C. remained free of any hydrolyzed peptides for at least 5 weeks.

[30] G. Klopman, Tetrahedron 1970, 26, 4549-4554.

[31] W. Zhang, L. Zhang, X. Li, J. A. Weigel, S. E. Hall, J. P. Mayer, J. Comb. Chem. 2001, 3, 151-153.

[32] C. Bello, F. Kikul, C. F. W. Becker J. Pept. Sci. 2015, 21, 201-207.

[33] (a) H. Kessler, B. Haase, Int. J. Pept. Protein Res. 1992, 39, 36-40; (b) T. Jeremic, A. Linden, H. Heimgartner, Helv. Chim. Acta 2004, 87, 3056-3079.

References for Example 3

[1] (a) S. Clarke, Annu. Rev. Biochem., 1992, 61, 355-386; (b) J. A. Glomset, M. H. Gelb and C. C. Farnsworth, Trends Biochem. Sci., 1990, 15, 139-142; (c) C. A. Hrycyna and S. Clarke, Mol. Cell. Biol., 1990, 10, 5071-5076; (d) F. L. Zhang and P. J. Casey, Annu. Rev. Biochem., 1992, 65, 241-269; (e) D. G. Mullen, K. Kyro, M. Hauser, M. Gustaysson, G. Veglia, J. M. Becker, F. Naider and M. D. Distefano, Bioorg. Med. Chem., 2011, 19, 490-497; (f) V. Diaz-Rodriguez, D. G. Mullen, E. Ganusova, J. M. Becker and M. D. Distefano, Org. Lett., 2012, 14, 5648-5651; (g) V. Diaz-Rodriguez, E. Ganusova, T. M. Rappe, J. M. Becker and M. D. Distefano, J. Org. Chem., 2015, 80, 11266-11274; (h) F. R. Naider and J. M. Becker, Pept. Sci., 1997, 3-14.

[2] (a) D. J. Craik and D. J. Adams, ACS Chem. Biol., 2007 2, 457-468; (b) M. C. Inserra, S. N. Kompella, S. N. Vetter, A. Brust, N. L. Daly, H. Cuny, D. J. Craik, P. F. Alewood, D. J. Adams and R. J. Lewis, Biochem. Pharmacol, 2013, 86, 791-799; (c) A. Gould and J. A. Camarero, ChemBioChem, 2017, 18, 1350-1363.

[3] W. Shang, X. Yang, X. Ju, Y. Xie, Y. Zhang and W.-H. Lee, J. Pept. Sci., 2017, doi:10.1002/psc.3017.

[4] J. M. Conlan, V. Musale, S. Attoub, M. Mangoni, J. Leprince, L. Coquet, T. Jouenne, Y. Abdel-Wahab, P. Flatt, A. Rinaldi, Journal of Peptide Science, October 2017, 23(10): 769-776.

[5] T. S. Kang, S. Vivekanandan, S. D. S. Jois and R. M. Kini, Angew. Chem. Int. Ed., 2005, 44, 6333-6337.

[6] (a) Merkler, D. J., Enzyme Microb. Technol., 1994, 16, 450-456; (b) H. Bultmann, J. Teuton, C. R. Brandt, Antimicrob. Agents Chemo., 2007, 51, 1596-1607.

[7] D. Goodwin, P. Simerska and I. Toth, Curr. Med. Chem., 2012, 19, 4451-4461.

[8] J. Alsina, F. Albericio, Biopolymers (Pept. Sci.), 2003, 71, 454-477.

[9] J. Hansen, F. Diness and M. Meldal, Org. Biomol. Chem., 2016, 14, 3238-3245.

[10] (a) H. E. Elashal, Y. E. Sim and M. Raj, Chem. Sci., 2017, 8, 117-123; (b) H. E. Elashel, R. D. Cohen and M. Raj, Chem. Commun., 2016, 52, 9699-9702.

[11] (a) J. A. Camarero, B. J. Hackel, J. J. de Yoreo and A. R. Mitchell, J. Org. Chem., 2004, 69, 4145-4151; (b) Y. Kwon, K. Welsh, A. R. Mitchell and J. A. Camarero, Org. Lett., 2004, 6, 3801-3804; (c) R. A. Turner, R. J. Weber and R. S. Lokey, Org. Lett., 2010, 12, 1852-1855; (d) E. Nicolas, J. Clemente, M. Perelló, F. Albericio, E. Pederoso and E. Giralt, Tetrahedron Lett., 1992, 33, 2183-2186; (e) A. A. Vinogradov, M. D. Simon, B. L. Pentelute, Org. Lett., 2016, 18, 1222-1225.

[12] Oxazolone formation: B. Henkel, L. Zhang and E. Bayer, Liebigs Ann. Recl., 1997, 10, 2161-2186.

[13] (a) Y. Fujiwara, K. Akaji and Y. Kiso, Chem. Pharm. Bull., 1994, 42, 724-726; (b) Y. M. Angell, J. Alsina, F. Albericio and G. Barany, J. Peptide Res., 2002, 60, 292-299; (c) H. Hibino, Y. Miki and Y. Nishiuchi, J. Pept. Sci., 2014, 20, 30-35.

[14] (a) Y. Han, F. Albericio and G. Barany, J. Org. Chem., 1997, 62, 4307-4312; (b) I. Ramos-Tomillero, H. Rodríguez and F. Albericio, Org. Lett., 2015, 17, 1680-1683; (c) A. Isidro-Llobet, M. Álvarez and F. Albericio, Chem. Rev., 2009, 109, 2455-2504; (d) H. Hibino and Y. Nishiuchi, Org. Lett., 2012, 14, 1926-1929; (e) H. Hibino, Y. Miki and Y. Nishiuchi, J. Pept. Sci., 2014, 20, 30-35; (f) J. Lukszo, D. Patterson, F. Albericio and S. Kates, Lett. Pept. Sci., 1996, 3, 157-166.

[15] (a) U. Boas, J. Brask, K. J. Jensen, Chem. Rev. 2009, 109, 2092-2118 and references therein; (b) G. Barany, Y. Han, B. Hargittai, R.-Q. Liu, J. T. Varkey, Biopolymers (Pept. Sci.), 2003, 71, 652-666; (c) V. Juvekar and Y. D. Gong, Org. Lett., 2016, 18, 836-839; (d) Z. Huang, D. J. Derksen and J. C. Vederas, Org. Lett., 2010, 12, 2282-2285.

[16] (a) P. Cherkupally, G. A. Acosta, S. Ramesh, B. G. de la Torre, T. Govender, H. G. Kruger, F. Albericio, Amino Acids, 2014, 46, 1827-1838; (b) J. Lukszo, D. Patterson, F. Albericio, S. A. Kates, Lett. Pept. Sci., 1996, 3, 157-166; (c) V. Juvekar, K.-T. Kim, Y.-D. Gong, Bull. Korean Chem. Soc., 2017, 38, 54-62.

[17] (a) D. S. Johnson, J. Martinez, A. B. Elgoyhen, S. F. Heinemann and J. M. McIntosh, Mol. Pharmacol., 1995, 48, 194-199; (b) E. F. R. Pereira, M. Alkondon, J. M. McIntosh and E. X. Albuquerque, J. Pharmacol. Exp. Ther., 1996, 3, 1472-148; (c) S. Luo, T. A. Nguyen, G. E. Cartier, B. M. Olivera, D. Yoshikami and J. M. McIntosh, Biochemistry, 1999, 38, 14548-14548; (d) M. Ellison, J. M. McIntosh and B. M. Olivera, J. Biol. Chem., 2003, 278, 757-764; (e) M. Ellison, F. Gao, H.-L. Wang, S. M. Sine, J. M. McIntosh and B. M. Olivera, Biochemistry, 2004, 43, 16019-16026.

[18] (a) B. M. Olivera, Mol. Biol. Cell 1997, 8, 2101-2109; (b) H. Terlau and B. M. Olivera, Physiol. Rev. 2004, 84, 4-68; (c) B. M. Olivera, J. S. Imperial, G. Bulaj, In Perspectives in Molecular Toxinology. 2002, 143-158; (d) O. Buczek, G. Bulaj and B. M. Olivera, Cell. Mol. Life Sci., 2005, 62, 3067-3079; (e) M. C. Inserra, S. N. Kompella, I. Vetter, A. Brust, N. L. Daly, H. Cuny, D. J. Craik, P. F. Alewood, D. J. Adams and R. J. Lewis, Biochem. Pharmacol., 2013, 86, 791-799.

[19] (a) K. B. Akondi, M. Muttenthaler, S. Dutertre, Q. Kaas, D. J. Craik, R. J. Lewis, P. F. Alewood, Chem. Rev., 2014, 114, 5815-5847; (b) M. Gorigora-Benitez, J. Tulla-Puche and F. Albericio, Chem. Rev., 2013, 114, 901-926.

[20] C. A. Arbour, H. Y. Saraha, T. F. McMillan and J. L. Stockdill, Chem. Eur. J., 2017, doi:10.1002/chem.201703380.

[21] (a) J. B. Blanco-Canosa and P. E. Dawson, Angew. Chem. Int. Ed., 2008, 47, 6851-6855. (b) J. B. Blanco-Canosa, B. Nardone, F. Albericio and P. E. Dawson, J. Am. Chem. Soc., 2015, 137, 7197-7209; (c) S. K. Mahto, C. J. Howard, J. C. Shimko and J. J. Ottesen, ChemBioChem, 2011, 12, 2488-2494.

[22] G. A. Acosta, M. Royo, B. G. de la Torre and F. Albericio, Tetrahedron Lett., 2017, 58, 2788-2791.

[23] Y. M. Angell, J. Alsina, F. Albericio and G. Barany, J. Pept. Res., 2002, 60, 292-299.

[24] See the Supporting Information for details.

[25] D. Lelièvre, V. P. Terrier, A. F. Delmas and V. Aucagne, Org. Lett., 2016, 18, 920-923.

26 T. D. Kondasinghe, H. Y. Saraha, S. B. Odeesho and J. L. Stockdill, Org. Biomol. Chem., 2017, 15, 2914-2918.

[27] (a) McIntosh, J. M., Yoshikami, D., Mahe, E., Nielsen, D. B., Rivier, J. E., Gray, W. R., and Olivera, B. M., J. Biol. Chem., 1994, 269, 16733-16739; (b) D. S. Johnson, J. Martinez, A. B. Elgoyhen, S. F. Heinemann, J. M. McIntosh, Mol. Pharm., 1995, 48, 194-199; (c) M. Ellison, F. Gao, H.-L. Wang, S. M. Sine, J. M. McIntosh, B. M. Olivera, Biochemistry, 2004, 43, 16019-16026.

[28] (a) I. V. Maslennikov, Z. O. Shenkarev, M. N. Zhmak, V. T. Ivanov, C. Methfessel and A. S. Arseniev, FEBS Lett., 1999, 444, 275-280; (b) J. Gehrmann, N. L. Daly, P. F. Alewood and D. J. Craik, J. Med. Chem., 1999, 42, 2364-2372; (c) J. S. Nielsen, P. Buczek and G. Bulaj, J. Pept. Sci., 2004, 10, 249-256.

[29] (a) J. M. McIntosh, D. Yoshikami, E. Mahe, D. B. Nielsen, J. E. Rivier, W. R. Gray and B. M. Olivera, J. Biol. Chem., 1994, 269, 16733-16739; (b) K. B. Akondi, M. Muttenthaler, S. Dutertre, Q. Kaas, D. J. Craik, R. J. Lewis and P. F. Alewood, Chem. Rev., 2014, 114, 5815-5847.

[30] C. J. Armishaw, N. L. Daly, S. T. Nevin, D. J. Adams, D. J. Craik, P. F. Alewood, J. Biol. Chem., 2006, 281, 14136-14143.

[31] 70% crude yield, 86% HPLC purity

[32] R. Söll and A. G. Beck-Sickinger, J. Pept. Sci., 2000, 6, 387-397.

[33] (a) B. Dang, T. Kubota, A. M. Correa, F. Bezanilla and S. B. H. Kent, Angew. Chem. Int. Ed., 2014, 53, 8970-8974; (b) C. Sun, G. Luo, S. Neravelta, S. S. Ghosh, B. Forood, Bioorg. Med. Chem. Lett., 2013, 23, 5203-5208; (c) J. Tulla-Puche, G. Barany, J. Org. Chem., 2004, 69, 4101-4107; (d) J. A. Camarero, G. J. Cotton, A. Adeva, T. W. Muir, J. Pept. Res., 1998, 51, 303-316; (e) G. A. Acosta, M. Royo, B. G. de la Torre and F. Albericio, Tetrahedron Lett., 2017, 58, 2788-2791.

[34] (a) L. Raibaut, P. Seeberger and O. Melnyk, Org. Lett., 2013, 15, 5516-5519; (b) L. Raibaut, M. Cargoet, N. Ollivier, Y. M. Chang, H. Drobecq, E. Boll, R. Desmet, J.-C. M. Monbaliu and O. Melnyk, Chem. Sci., 2016, 7, 2657-2665.

[35] (a) B. Bacsa, S. BOsze and C. Oliver Kappe, J. Org. Chem., 2010, 75, 2103-2106; (b) M. Quibell, W. G. Turnell and T. Johnson, J. Org. Chem., 1994, 59, 1745-1750; (c) M. M. Condron, B. H. Monien and G. Bitan, Open Biotechnol. J., 2008, 2, 87-93.

[36] (a) P. E. Dawson, T. W. Muir, I. Clark-Lewis and S. B. Kent, Science, 1994, 266, 776-779; (b) E. C. B. Johnson and S. B. H. Kent, J. Am. Chem. Soc., 2006, 128, 6640-6646.

[37] D. G. Mullen, K. Kyro, M. Hauser, M. Gustaysson, G. Veglia, J. M. Becker, F. Naider and M. D. Distefano, Bioorg. Med. Chem., 2007, 15, 931-938.

The invention claimed is:

1. A method of synthesizing a peptide, wherein the method comprises preparing a first amino acid for synthesis, coupling an amino group of a second amino acid to the carboxyl group of the first amino acid to obtain a peptide, and optionally elongating the peptide by coupling one or more amino acids sequentially to a C-terminus of the peptide, wherein the amino acids used in the method are derivatized amino acids comprising a diamino-aryl group, and wherein the method proceeds without detectable epimerization of the second or sequentially coupled amino acid at the carboxyl terminus of the peptide.

2. The method of claim 1, wherein the method comprises solid-phase peptide synthesis, solution phase peptide synthesis, or fluorous phase peptide synthesis.

3. The method of claim 1, wherein the method comprises derivatizing amino acids by synthesizing amino acid diaminobenzoyl derivatives.

4. The method of claim 3, wherein synthesis of amino acid diaminobenzoyl derivatives comprises obtaining Fmoc protected amino acid (Fmoc-AA-OH), reacting diaminobenzoylOMe (DbzOMe) with Fmoc-AA-OH to obtain Fmoc-AA-DbzOMe, and reacting with piperidine to remove Fmoc to yield H-AA-DbzOMe derivative.

5. The method of claim 1, wherein synthesis of amino acid diamino-aryl derivatives comprises obtaining Fmoc protected amino acid (Fmoc-AA-OH), reacting diamino-aryl molecule with Fmoc-AA-OH to obtain Fmoc-AA-diamino-aryl molecule, and reacting with piperidine to remove Fmoc to yield H-AA-diamino aryl derivative.

6. The method of claim 1, wherein preparing the first amino acid comprises attaching the first amino acid to a resin prior to coupling the amino group of the second amino acid to the carboxyl group of the first amino acid.

7. The method of claim 6, wherein attaching the first amino acid to the resin comprises anchoring the α-amino group or a side-chain of the first amino acid to the resin.

8. The method of claim 7, wherein the method further comprises activating the first amino acid to form a first amino acid comprising an N-acyl urea group.

9. The method of claim 8, wherein activating the first amino acid comprises treating with 4-nitrophenyl chloroformate or other phosgene equivalent and followed by treating with Hünig's base.

10. The method of claim 9, wherein coupling comprises adding a derivatized second amino acid to displace the N-acyl urea group on the first amino acid at its C terminus to yield a peptide.

11. The method of claim 10, wherein the method further comprises elongation of the peptide comprising repetition of activation of the peptide and coupling of the peptide with another derivatized amino acid to obtain an N-acyl urea group terminated peptide.

12. The method of claim 11, wherein the method further comprises after elongating the peptide to a desired length, cleaving the N-acyl urea group from the C-terminus of the peptide to obtain a C-terminally functionalized unprotected peptide or a C-terminally functionalized protected peptide.

13. The method of claim 12, wherein cleaving the peptide comprises acidic resin cleavage to obtain a C-terminally functionalized unprotected peptide.

14. The method of claim 13, wherein the acidic resin cleavage comprises treatment with trifluoroacetic acid (TFA) to cleave the peptide from the resin.

15. The method of claim 12, wherein cleaving the peptide comprises nucleophilic resin cleavage to obtain a C-terminally functionalized protected peptide.

16. The method of claim 15, wherein nucleophilic resin cleavage comprises treatment with one of the following nucleophiles: $NH_3$, $BuNH_2$, $H_2N(CH_2)_3N_3$, propargylamine, aniline, $H_2NNH_2$, MeHNOMe, MeOH, EtOH, i-PrOH, BnOH, PhOH, $H_2O$, or $NaBH_4$.

17. The method of claim 11, wherein unreacted derivatized amino acids are recovered and reused.

18. The method of claim 10, wherein the method further comprises elongation of the peptide in the C to N direction.

19. The method of claim 18, wherein elongation to the desired length is completed in the N to C direction.

20. The method of claim 1, wherein the method proceeds without detectable epimerization of the second and sequentially coupled amino acid at the carboxyl terminus of the peptide.

* * * * *